(12) United States Patent
Games et al.

(10) Patent No.: US 6,717,031 B2
(45) Date of Patent: *Apr. 6, 2004

(54) METHOD FOR SELECTING A TRANSGENIC MOUSE MODEL OF ALZHEIMER'S DISEASE

(76) Inventors: Kate Dora Games, 411 Central Ave., San Francisco, CA (US) 94117; Dale Bernard Schenk, 605 Sharp Park Rd., Pacifica, CA (US) 94044; Lisa Claire McConlogue, 283 Juanita Way, San Francisco, CA (US) 94127; Peter Andrew Seubert, 222 Northwood Dr., S. San Francisco, CA (US) 94080; Russell E. Rydel, 2211 Village Ct., #6, Belmont, CA (US) 94002

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/149,718

(22) Filed: Sep. 8, 1998

(65) Prior Publication Data

US 2002/0104104 A1 Aug. 1, 2002

Related U.S. Application Data

(63) Continuation-in-part of application No. 08/660,487, filed on Jun. 7, 1996, which is a continuation-in-part of application No. 08/480,653, filed on Jun. 7, 1995, now abandoned, application No. 09/149,748, which is a continuation-in-part of application No. 08/659,797, filed on Jun. 7, 1996, and a continuation-in-part of application No. 08/486,538, filed on Jun. 7, 1995.

(51) Int. Cl.[7] .................... A01K 67/00; G01N 33/00
(52) U.S. Cl. .................... 800/12; 800/3; 800/18; 435/6; 435/7.1
(58) Field of Search ................... 800/3, 12, 18; 435/354, 29, 6, 7.1

(56) References Cited

U.S. PATENT DOCUMENTS

| | | |
|---|---|---|
| 4,666,829 A | 5/1987 | Glenner et al. |
| 4,736,866 A | 4/1988 | Leder et al. |
| 4,873,191 A | 10/1989 | Wagner et al. |
| 5,134,062 A | 7/1992 | Blass |
| 5,200,339 A | 4/1993 | Abraham |
| 5,220,013 A | 6/1993 | Ponte et al. |
| 5,221,607 A | 6/1993 | Cordell et al. |
| 5,234,814 A | 8/1993 | Card et al. |
| 5,387,742 A | 2/1995 | Cordell |
| 5,441,870 A | 8/1995 | Seubert et al. |
| 5,455,169 A | 10/1995 | Mullan |
| 5,547,841 A | 8/1996 | Marotta et al. |
| 5,604,102 A * | 2/1997 | McConlogue et al. ....... 435/7.1 |
| 5,612,486 A | 3/1997 | McConlogue et al. |
| 5,720,936 A * | 2/1998 | Wadsworth et al. ......... 424/9.1 |
| 5,811,633 A * | 9/1998 | Wadsworth et al. ........... 800/2 |
| 5,877,399 A | 3/1999 | Hsiao et al. |

FOREIGN PATENT DOCUMENTS

| | | |
|---|---|---|
| EP | 0 173 494 A2 | 3/1986 |
| EP | 0 184 187 A2 | 6/1986 |
| EP | 0 267 678 A1 | 5/1988 |
| EP | 0 279 582 A2 | 8/1988 |
| EP | 0 123 527 B1 | 1/1990 |
| EP | 0 451 700 AT | 10/1991 |
| EP | 0 171 496 B1 | 5/1993 |
| EP | 0 561 087 A1 | 9/1993 |
| EP | 0 653 154 A2 | 5/1995 |
| GB | 2 199 845 A | 7/1988 |
| WO | WO 86/01533 | 3/1986 |
| WO | WO 87/02671 | 5/1987 |
| WO | WO 87/05325 | 9/1987 |
| WO | WO 88/01648 | 3/1988 |
| WO | WO 88/03951 | 6/1988 |
| WO | WO 89/06689 | 7/1989 |
| WO | WO 91/04447 | 4/1991 |
| WO | WO 91/16628 | 10/1991 |
| WO | WO 91/19810 | 12/1991 |
| WO | WO 92/00521 | 1/1992 |
| WO | WO 92/06187 | 4/1992 |
| WO | WO 92/09699 | 6/1992 |
| WO | WO 92/13069 | 8/1992 |
| WO | WO 93/02189 | 2/1993 |
| WO | WO 93/07296 | 4/1993 |

(List continued on next page.)

OTHER PUBLICATIONS

Sirinathsinghji, Transgenic Models for Alzheimer'Disease, Current Research in Alzheimer's Disease, 1998, vol. 3, No. 2, 47–56.*

(List continued on next page.)

Primary Examiner—Deborah Crouch
(74) Attorney, Agent, or Firm—Townsend and Townsend and Crew LLP

(57) ABSTRACT

The construction of transgenic animal models of human Alzheimer's disease, and methods of using the models to screen potential Alzheimer's disease therapeutics, are described. The models are characterized by pathologies similar to pathologies observed in Alzheimer's disease, based on expression of all three forms of the β-amyloid precursor protein (APP), APP695, APP751, and APP770, as well as various point mutations based on naturally occurring mutations, such as the London and Indiana familial Alzheimer's disease (FAD) mutations at amino acid 717, predicted mutations in the APP gene, and truncated forms of APP that contain the Aβ region. Animal cells can be isolated from the transgenic animals or prepared using the same constructs with standard techniques such as lipofection or electroporation. The transgenic animals, or animal cells, are used to screen for compounds altering the pathological course of Alzheimer's disease as measured by their effect on the amount of APP, β-amyloid peptide, and numerous other Alzheimer's disease markers in the animals, the neuropathology of the animals, as well as by behavioral alterations in the animals.

56 Claims, 11 Drawing Sheets

FOREIGN PATENT DOCUMENTS

| | | |
|---|---|---|
| WO | WO 93/14200 | 7/1993 |
| WO | WO 94/00569 | 1/1994 |
| WO | WO 94/10569 | 5/1994 |
| WO | WO 94/23049 | 10/1994 |
| WO | WO 95/11968 | 5/1995 |
| WO | WO 95/11994 | 5/1995 |
| WO | WO 95/14769 | 6/1995 |
| WO | WO 95/20666 | 8/1995 |
| WO | WO 96/13513 | 6/1996 |
| WO | WO 96/17926 | 6/1996 |
| WO | WO 96/18900 | 6/1996 |

OTHER PUBLICATIONS

Aguzzi, et al., "Transgenic and Knock–out Mice: Models of Neurological Disease,," Brain Pathol. 4:3–20 (1994).

Akiyama, et al., "Immunohistochemical localization of vitronectin, its receptor and beta–3 integrin in Alzheimer's brain tissue," J. of Neuroimmunol. 32:19–28 (1991).

Akiyama and McGeer, "Brain microglia constitutively express –2 integrins," J. of Neuroimmunol. 30:81–93 (1990).

Akiyama, et al., "Morphological diversities of CD44 positive astrocytes in the cerebral cortex of normal subjects and patients with Alzheimer's disease," Brain Res. 632:249–259 (1993).

Akiyama, et al., "Expression of the receptor for macrophage colony stimulating factor by brain microglia and its upregulation in brains of patients with Alzheimer's disease and amyotrophic lateral sclerosis," Brain Res. 639:171–174 (1994).

Akiyama, et al., "Expression of intercellular adhesion molecule (ICAM)–1 by a subset of astrocytes in Alzheimer's disease and some other degernative neurological disorders," Acta Neuropathol. 85:628–634 (1993).

Akiyama, et al., "Expression of MRP14, 27E10, interferon– and leukocyte common antigen by reactive microglia in postmortem human brain tissue," J. of Neuroimmunol. 50:195–201 (1994).

Akiyama, et al., "Microglia express the type2 plasminogen activator inhibitor iini the brain of control subjects and patients with Alzheimer's disease," Neurscience Letters 164:233–235 (1993).

Alberts, A., et al., "Mevinolin: A highly potent competitive inhibitor of hydroxymethylglutaryl–coenzyme A reductase and a cholesterol–lowering agent" Proc. Natl. Acad. Sci. USA 77:3957–3961 (1980).

Anderson, et al., "Differential brain expression of the Alzheimer's amyloid precursor protein," EMBO J. 8:3627–3632 (1989).

Arai et al., "Defined neorofilament, r, and –amyloid precursor protein epitopes distinguish Alzheimer from non–Alzheimer senile plaques," Proc. Natl. Acad. Sci. USA 87:2249–2253 (1990).

Argyle, et al., "Psychogeriatric Patients: Their Supporters' Problems," Age and Ageing 14:355–360 (1985).

Araujo and Cotman, "Beta–amyloid stimulates glial cells in vitro to produce growth factors that accumulate in senile plaques in Alzheimer's disease," Brain Research 569:141–145 (1992).

Aschoff, "Circadian rhyths: influences of internal and external factors on the period measured in constant conditions," Zeitschrift fur Tierpsychologie 49:225–249 (1979).

Bachmann, S., et al., "Transgenic rats carrying the mouse renin gene—morphological characterization of a low–renin hypertension model" Kidney Int. 41(1):24–36 (1992) (abstract only).

Berglund, L., et al., "Effects of lovastatin therapy on guinea pig low density lipoprotein composition and metabolism" J. Lipid Res. 30:1591–1600 (1989).

Bick, et al., (Editors) "The early story of Alzheimer's Disease," (Raven Press, New York 1987).

Borchelt, D., et al., "Familial Alzheimer's Disease–Linked Presenilin 1 Variants Elevate A 1–42/1–40 Ratio In Vitro and In Vivo" Neuron 17:1005–1013 (1996).

Bothwell, et al., "Heavy Chain Variable Region contribution to the NPb Family of Antibodies: Somatic Mutation Evident in a y2a Variable Region," Cell 24:625–637 (1981).

Brandan and Inestrosa, "Extracellualr matrix components and amyloid in neuritic plaques of Alzheimer's disease," General Pharmacology 24:1063–1068 (1993).

Brewer, et al., "Optimized Survival of Hippocampal Neurons in B27–Supplemented NeurobasalTM, a New Serum–free Medium Combination," J. Neuroscience Res. 35(5):567–577 (1993).

Brown, et al., "Axonal Polypeptides Cross–Reactive with Antibodies to Neurofilament Proteins," Journal of Neurochemistry 40(2): 299–308 (1983).

Burke, et al., "Cloning of Large Segments of Exogenous DNA into Yeast by Means of Artificial Chromosome Vectors," Science 236:806 (1987).

Busciglio, J., et al., "Generation of –amyloid in the secretory pathway in neuronal and nonneuronal cells" Proc. Natl. Acad. Sci. USA 90:2092–2096 (1993).

Buxbaum, et al. "Calcium Regulates Processing of the Alzheimer Amyloid Protein Precursor in a Protein Kinase C–independent Manner," Proc. Natl. Acad. Sci. USA, 91: 4489–4493 (1994).

Buxbaum, et al., "Expression of APP in Brains of Transgenic Mice Containing the Entire Human APP Gene," Biochem. Biophys. Res. Comm. 197:639–645 (1993).

Bymaster, et al., "Neurochemical Effects of the M1 Muscarinic Agonist Xanomeline (LY246708/NNC11–0232)," J. Pharm. Exp. Ther. 269:282–289 (1994).

Cai, et al., "Release of Excess Amyloid Protein from a Mutant Amyloid Protein Precursor," Science 259:514–516 (1993).

Capecchi, "Altering the Genome by Homologous Recombination," Science 244:1288–1292 (1989).

Ceballos–Picot, et al., "Neuronal–specific expression of human copper–zinc superoxide dismutase gene in transgenic mice: animal model of gene dosage effects in Down's syndrome," Brain Res. 552:198–214 (1991).

Chartier–Harlin, et al., "Early–Onset Alzheimer's Disease Caused by Mutations at Codon 717 of the –Amyloid Precursor Protein Gene," Nature 353: 844–846 (1991).

Chomazynski and Sacchi, "Single–Step Method of RNA Isolation by Acid Guanidinium Thiocyanate–Phenol–chloroform Extraction," Analyt. Biochem. 162:156–159 (1987).

Chou, et al., "Alzheimer Cortical Neurons Containing Abundant Amyloid mRNA. Relationship to Amyloid Deposition and Senile Plaques," Journal Psychiatric Research 24(1): 37–50 (1990).

Chou, et al., "Alzheimer Cortical Neurons Containing Abundant Amyloid mRNA. Relationship to Amyloid Deposition and Senile Plaques," J. Psych. Res. 24:37–50 (1990).

Citron, et al., "Mutation of the –amyloid precursor protein in familial Alzheimer's disease increases –protein production," Nature 360:672–674 (1992).

Citron, et al., "Generation of Amyloid Protein from Its Precursor Is Sequence Specific," Neuron 14:661–670 (1995).

Connor, "Firms to fight ban on animal patents," New Scientist p. 21 (Feb. 11, 1988).

Corder, "Gene Dose of Apolipoprotein E TYpe 4 Allele and the Risk of Alzheimer's Disease in Late Onset Families," Science 261:921–923 (1993).

Cork, et al., "Neurofibrillary Tangles and Senile Plaques in Aged Bears," J. Neuropath, Exp. Neurol. 47:629–641 (1988).

Cowen, "Regulating Biotech: How Much Is Enough?" The Christian Science Monitor p. 16 (Jun. 3, 1988).

Cowen, "New Wave Crops Heading for the Farm," The Christian Science Monitor p. 16 (Jun. 1, 1988).

Cowen, "'Value Added' Animals: What is On the Horizon?" The Christian Science Monitor p. 16 (Jun. 2, 1988).

Coyle, et al., "Alzheimer's Disease: A Disorder of Cortical Cholinergic Innervation," Science 219:1184–1190 (1983).

David, et al., "Absence of a Close Linkage Between Alzheimer's Disease Susceptibility Gene and a Polymorphic DNA Probe Coding for –Amyloid," Biomedicine & Pharmacotherapy 42:575–578 (1988).

Davies, "Alz–50, A68, and the Paired Helical Filaments of Alzheimer's Disease," The Journal of NIH Research 3:53–56 (1991).

Davies and Maloney, "Selective Loss of Central Cholinergic Neurons in Alzheimer's Disease," Lancet 2:1403 (1976).

Davies, et al., "Creation of Mice Expressing Human Antibody Light Chains by Introduction of a Yeast Artificial Chromosome Containing the Core Region of the Human Immunoglobulin K Locus," Bio/Technology 11:911–914 (1993).

de Boer, J., "Software package for the management of sequencing projects using lacl transgenic animals" Environ. Mol. Mutagenesis 25(3):256–262 (1995) (abstract only).

DeFeudis, "Beta–Amyloid Protein in Transgenic Mice," Drug News & Perspective 4(10):617–619 (1991).

Delabar, et al., " Amyloid Gene Duplication in Alzheimer's Disease and Karyotypically Normal Down Syndrome," Science 235:1390–1392 (1987).

DeWitt, et al., "Chondroitin Sulfate Proteoglycans Are Associated with the Lesions of Alzheimer's Disease," Exp. Neurol. 121:149–152 (1993).

Dickson, et al., "Ubiquitin immunoelectron microscopy of dystrophic neurites in cerebellar senile plaques of Alzheimer's disease," Acta Neuropath. 79:486–493 (1990).

Doetschman, et al., "The in vitro development of blastocyst–derived embryonic stem cell lines: formationof visceral yolk sac, blood island and myocardium," J. Embryol. Exp. Morphol. 87:27 (1985).

Dresse, et al. "Towards a Pharmacological Approach of Alzheimer's Disease Based on the molecular Biology of the Amyloid Precursor Protein (APP)," Life Sciences, 55:2179–2187 (1994).

Duff, et al., "Mouse model made," Nature 373:476–477 (1993).

Dugan, et al., "The Ras–related GTP–binding Protein, Rab1B, Regulates Early Steps in Exocytic Transport and Processing of Amyloid Precursor Protein," J. Biological Chem. 270(18):10982–10989 (1995).

Dunnett, "Operant delayed matching and non–matching position in rats" in Behavioral Neuroscience, vol. I: A Practical Approach (Sagal, ed., IRL Press, N.Y., 1993) pp. 123–136.

Ebert, K., et al., "A Moloney MLV–rat somatotropin fusion gene produces biologically active somatotropin in a transgenic pig" Mol. Endocrinol. 2(3):277–283 (1988) (abstract only).

Ennaceur and Delacour, "A new one–trial for neurobiological studies of memory in rats. 1. Behavioral data," Behav. Brain Res. 31:47–59 (1988).

Epstein, et al., "Transgenic mice with increased Cu/Zn–superoxide dismutase activity: Animal model of dosage effects in Down syndrome," Proc. Natl. Acad. Sci. USA 84:8044–8048 (1987).

Esch, et al., "Cleavage of amyloid peptide during constitutive processing of its precursor," Science 248:1122–1124 (1991).

Estus, et al., "Potentially amyloidogenic, carboxyl–terminal derivatives of the amyloid protein precursor," Science 255:726–728 (1992).

Estus, et al., "Altered Gene Expressoin in Neurons during Programmed Cell Death: Identificationof c–jun as Necessary for Neuronal Apoptosis," J. Cell Biol. 127:1717–1727 (1994).

Felsenstein et al., "Transgenic Rat and In–Vitro Studies of beta–amyloid Precursor Protein Processing" in Alzheimer's and Parkinson's Diseases (Hanin, ed., Plenum Press, New York, 1995), pp. 401–409.

First, N., "New animal breeding techniques and their application" J. Reprod. Fertil. Suppl. 41:3–14 (1990) (abstract only).

Fisher, "Start–Ups Join Alzheimer Race," New York Times, Aug. 23, 1989 D1.

Flood et al., "Amnestic effects in mice of four synthetic peptides homologous to amyloid protein from patients with Alzheimer disease," Proc. Natl. Acad. Sci. 88:3363–3366 (1986).

Frederickson and Brunden, "New Opportunities in AD Research—Roles of Immunoinflammatory Responses and Glia," Alzheimer Disease and Associated Disorders 8:159–165 (1994).

Freeman and Bumstead, "Transgenic poultry: theory and practice," World's Poultry Science Journal 43:180–189 (1987).

Fukuchi, et al., "Transgenic Animal Models for Alzheimer's Disease," Ann. N.Y. Acad. Sci. 695:217–223 (1993).

Fukuchi, et al., "Overexpression of amyloid precursor protein alters its normal processing and is associated with neurotoxicity," Biophys. Res. Commun. 182:165–173 (1992).

Fukuchi, et al., "Expression of a carboxy–terminal region of the B–amyloid precursor protein in a heterogenous culture of neuroblastoma cells: evidence for altered processing and selective neurotoxicity," Mol. Brain Res. 16:37–46 (1992).

Furuya, et al., "Amyloid –Protein Gene Duplication is not Common in Alzheimer's Disease: Analysis by Polymorphic Restriction Fragments," Biochemical and Biophysical Research Communications 150(1):75–81 (1988).

Gabuzda, et al. "Inhibiton of B–Amyloid Production by Activation of Protein Kinase C," J. Neurochemistry, 61: 2326–2329 (1993).

Games, et al., "Lack of Alzheimer Pathology After –Amyloid Protein Injections in Rat Brain," Neurobiol. Aging 13:569–576 (1992).

Games, et al., "Alzheimer–type neuropathology in transgenic mice overexpressing V717F –amyloid precursor protein," Nature 373:523–527 (1995).

Ganten, D., et al., "Species specificity of renin kinetics in transgenic rats harboring the human renin and angiotensinogen genes" Proc. Natl. Acad. Sci. USA 89(16):7806–7810 (1992) (abstract only).

Garfield, et al., "Differential Effects of Ketamine Stereoisomers on Maze Performance in the Mouse," Anesthesiology 63:681–683 (1985).

Glanville, et al., "Structure of Mouse Metallothionein–I Gene and its mRNA," Nature 292:267–269 (1981).

Glenner, et al., "Alzheimer's Disease: Initial Report of the Purification and Characterization of a Novel Cerebrovascular Amyloid Protein," Biochemical and Biophysical Research Communication 120(3)885–890 (1984).

Goate, et al., "Segregation of a Missense Mutation in the Amyloid Precursor Protein Gene with Familial Alzheimer's Disease," Nature 349:704–706 (1991).

Golde, et al., "Expression of Amyloid Protein Precursor mRNAs: Recognition of a Novel Alternatively Spliced Form and Quantitation in Alzheimer's Disease Using PCR," Neuron 4:253–267 (1990).

Golde, et al., "Processing of the amyloid protein precursor to potentially amyloidogenic derivatives," Science 255:728–730 (1992).

Goldgaber, et al., "Characterization and Chromosomal Localization of a cDNA Encoding Brain Amyloid of Alzheimer's Disease," Science 235:877–880 (1987).

Gravina, et al., "Amyloid Protein (A) in Alzheimer's Disease Brain," J. Biol. Chem. 270:7013–7016 (1995).

Greenamyre and Maragos, "Neurotransmitter Receptors in Alzheimer Disease," Cerebrovascular and Brain Metabolism Reviews 5;61–94 (1993).

Greenberg, et al., "APP Transgenesis: Approaches Toward the Development of Animal Models for Alzheimer Disease Neuropathology", *Neurobiology of Aging*, 17(2):153–171 (1996).

Griffith and Griffith (Editors) "Mutagenesis by PCR" in PCR Technology: Current Inovations (CRC Press, 1994) pp. 69–83.

Haass, et al. "Polarized Secretion of B–Amyloid Precursor Protein and Amyloid β– Peptide in MDCK Cells," Proc. Natl. Acad. Sci. USA, 91: 1564–1568 (1995).

Haass and Selkoe, "Cellular Processing of –Amyloid Precursor Protein and the Genesis of Amyloid –Peptide," Cell 75:1039–1042 (1993).

Hammer, R., et al., "Production of transgenic rabbits, sheep and pigs by microinjection" Nature 315(6021):680–683 (1985) (abstract only).

Hammer, R., et al., "Genetic engineering of mammalian embryos" J. Anim. Sci 63(1):269–278 (1986) (abstract only).

Hammer, et al., "Spontaneous Inflammatory Disease in Transgenic Rats Expressing HLA–B27 and Human 2m: An Animal Model of HLA–B27–Associated Human Disorders," Cell 63:1099–1112 (1990).

Hansen, et al., "Re–examination and further development of a precise and rapid dye method for measuring cell growth/cell kill," J. Immun. Method. 119:203–210 (1989).

Hardy, J., "Amyloid, the presenilins and Alzheimer's disease" Trends in Neuroscience 20(4):154–159 (1997).

Hardy, "Framing –amyloid," Nature Genetics 1:233–234 (1992).

Hardy and Allsop, "Amyloid deposition as the central event in the aetiology of Alzheimer's disease," Trends in Pharm. Sci. 12:383–388 (1991).

Harlow et al., Antibodies: A Laboratory Manual (Cold Spring Harbor, NY 1988).

He, et al., "Expression of a large family of POU–domain regulatory genes in mammalian brain development," Nature 340:35–42 (1989).

Hendriks, et al., "Presenile dementia and cerebral haemorrhage linked to a mutation at codon 692 of the –amyloid precursor protein gene," Nature Genetics 1:218–221 (1992).

Higgins, et al. "Transgenic Mice Expressing Human –APP751, But Not Mice Expressing –APP695, Display Early Alzheimers Disease–like Histopathology" Ann. N.Y. Acad. Sci. 695: 224–227 (1993).

Higgins, et al., "Transgenic Mouse Brain Histopathology Resembles Early Alzheimer Disease," Ann Neurol. 35:598–607 (1995).

Higgins, et al. "Genetically Engineered Animal Models of Human Neurodegenerative Diseases," Neurodegeneration, 4: 117–129 (1995).

Higgins, L., et al., "Genetically Engineered Animal Models of Alzheimer's Disease" Methods: A Companion to Methods in Enzymology 10:384–391 (1996).

Higgins, et al., "Early Alzheimer disease–like histopathology increases in frequency with age in mice transgenic for –APP751," Proc. Natl. Acad. Sci. USA 92:4402–4406 (1995).

Himber, J., et al., "Effects of stigmastanyl–phosphocholine (Ro 16–6532) and lovastatin on lipid and lipoprotein levels and lipoprotein metabolism in the hamster on different diets" J. Lipid Res. 36:1567–1585 (1995).

Hogan, et al., Manipulating the Mouse Embryo (Cold Spring Harbor Laboratory, Cold Spring Harbor, NY, 1986).

Howland, et al., "Mutant and Native Human –Amyloid Precursor Proteins in Transgenic Mouse Brain" Neurobiol. of Aging 16:685–699 (1995).

Hsaio, "Age related CNS Disorder and Early Death in Transgenic FVB/N Mice Overexpressing Alzheimer Amyloid Precursor Proteins" Neuron, 15: 1203–1218 (1995).

Hsiao, K., et al., "Correlative Memory Deficits, A Elevation, and Amyloid Plaques in Transgenic Mice" Science 274:99–102 (1996).

Huang, et al., "Intervening sequences increase efficiency of RNA 3' processing and accumulation of cytoplasmic RNA," Nucleic Acids Res. 18:937–947 (1990).

Huff, M., et al., "Regulation of Low Density Lipoprotein Apoprotein B Metabolism by Lovastatin and Cholestyramine in Miniature Pigs: Effects on LDL Composition and Synthesis of LDL Subfractions" Metabolism 38(3):256–264 (1989).

Hung, et al., "Activation of Protein Kinase C Inhibits Cellular Production of the Amyloid –Protein," J. Biol. Chem. 268:22959–22962 (1993).

Hyman, et al., "Amyloid, dementia, and Alzheimer's disease," Current Opinion in Neurology and Neurosurgery, 5:88–93 (1992).

Jenkins, et al., "Fine Mapping of an Alzheimer Disease–Associated Gene Encoding Beta–Amyloid Protein," Biochemical and Biophysical Research Communications 151(1):1–8 (1988).

Joachim, et al. "The Seminal Role of β–Amyloid in the Pathogenesis of Alzheimer Disease," *Alzheimer's Disease and Associated Disorders*, 6:7–34 (1992).

Joachim, et al., "Amyloid –Protein Deposition in Tissues Other than Brain in Alzheimer's Disease," Nature 341:226–230 (1989).

Jorm (Editors) A Guide to the Understanding of Alzheimer's Disease and Related Disorders, (New York University Press, New York 1987).

Joyner, et al., "Production of a mutation in mouse En–2 gene by homologous recombination in embryonic stem cells," Nature 338:153–156 (1989).

Jucker, et al., "Age–associated inclusions in normal and transgenic mouse brain," Science 255:1443–1445 (1992).

Kalaria and Perry, "Amyloid P component and other acute–phase protein associated with cerebellar A –deposits in Alzheimer's disease," Brain Research 631:151–155 (1993).

Kammesheidt, et al., "Deposition of /A4 immunoreactivity and neuronal pathology in transgenic mice expressing the carboxy–terminal fragment of the Alzheimer amyloid precursor in the brain," Proc. Natl. Acad. Sci. USA 89:10857–10861 (1992).

Kang, et al., "The Precursor of Alzheimer's Disease Amyloid A4 Protein Resembles a Cell–Surface Receptor," Nature 325:733–736 (1987).

Kasof, G., et al., "Development expression of Fos–lacZ in the brains of postnatal transgenic rats" Brain Research. Developmental Brain Rsearch 93(1–2):191–197 (1996) (abstract only).

Katzman, "Alzheimer'S Disease," The New England Journal of Medicine 314(15): 964–973 (1986).

Kawabata, et al., "Amyloid plaques, neurofibrillary tangles and neuronal loss in brains of transgenic mice overexpressing a C–terminal fragment of human amyloid precursor protein," Nature 356:265 (1992).

Kawabata, et al., "Alzheimer's Retraction," Nature 356:23 (1992).

Kawabata, et al., "Amyloid Plaques, Neurofibrillary Tangles and Neuronal Loss in Brains of Transgenic Mice Overexpressing a C–Terminal Fragment of Human Amyloid Precursor Protein," Nature 354: 476–478 (1991).

Kawamata, et al., "Lactotransferrin Immunocytochemistry in Alzheimer and Normal Human Brain," Am. J. of Pathol. 142:1574–1585 (1993).

Kelly (Editors) Alzheimer's Disease and Related Disorders, Research and Development (Charles C. Thomas, Springfield, IL. 1984).

Kidd, "Paired Helical Filaments in Electron Microscopy of Alzheimer's Disease," Nature 197:192–193 (1963).

Kesner, et al., "Medial Septal and Nucleus Basalis Magnocellularis Lesions Produce Order Memory Deficits in Rats Which Mimic Symptomatology of Alzheimer's Disease," Neurobiol. Aging 7:287–292 (1986).

Kitaguchi, et al., "Novel Precursor of Alzheimer's Disease Amyloid Protein Shows Protease Inhibitory Activity," Nature 331:530–532 (1988).

Knops, et al., "Isolation of Baculovirus–derived Secreted and Full–length –Amyloid Precursor Protein," J. of Biol. Chem. 266:7285–7290 (1991).

Kosik, et al., "Alzheimer's Disease: A Cell Biological Perspective," Science 256:780–783 (1992).

Kowall, et al., "An In Vivo Model for the Neurodegenerative Effects of Amyloid and Protection by Substance P," Proceedings of the National Academy of Science (U.S.A.) 88:7247–7251 (1991).

Kovanen, P., et al., "Regulatory role for hepatic low density lipoprotein receptors in vivo in the dog" Proc. Natl. Acad. Sci. USA 78:1194–1198 (1981).

Lamb, et al. "Introduction and Expression of the 400 Kilobase Precursor Amyloid Protein Gene in Transgenic Mice," *Nature Genetics*, 5:22–30 (1993).

Lannfelt, et al.,"Alzheimer's disease: molecular genetics and transgenic animal models," Behavioural Brain Res. 57:207–213 (1993).

La Ville, A., et al., "Ihibition of cholesterol synthesis reduces low–density–lipoprotein apoprotein β production without decreasing very–low–density–lipoprotein apoprotein β synthesis in rabbits" Biochem. J. 219:321–323 (1984).

Lee, "Unraveling the Mystery of the Paired Helical Filaments of Alzheimer's Disease," The Journal of NIH Research 3:52–55 (1991).

Lees–Miller, et al., "Three Novel Brain Tropomyosin Isoforms Are Expressed from the Rat –Tropomyosin Gene through the Use of Alternative Promoters and Alternative RNA Processing," Mol. Cell. Biol. 10(4)::1729–1742 (1990).

Lemaire, et al., "The PreA4695 Precursor Protein of Alzheimer's Disease A4 Amyloid is Encoded by 16 Exons," Nucleic Acids Research 17(2):517–522 (1989).

Leveugle and Fillif, "Proteoglycans and the Acute–Phase Response in Alzheimer's Disease Brain," Molecular Neurobiol. 9:25–32 (1994).

Levy, et al., "Mutation of the Alzheimer's Disease Amyloid Gene in Hereditary Cerebral Hemorrhage, Dutch Type," Science 248:1124–1126 (1990).

List of Presentations of APP and A , Cambridge Healthtech Institute's Second Conference on Alzheimer's Disease (1997).

List of Presentations on APP and A , IBC's 6th Annual Conference on Alzheimer's Disease (1997).

Lo, D., et al., "Expression of mouse IgA by transgenic mice, pigs and sheep" Eur. J. Immunol. 21(4):1001–1006 (1991) (abstract only).

Lo, et al. "Metabolism of the "Swedish" Amyloid Precursor Protein Variant in Madin–Darby Canine Kidney Cells," J. Biol. Chem. 269:30966–30973 (1994).

Lovell–Badge, Teratocarcinomas and Embryonic Stem Cells, A Pratical Approach, (Robertson, E.J., Editors, IRL Press 1987).

Lovestone and Anderton, "Cytoskeletal abnormalities in Alzheimer's disease," Current Opinion in Neurology and Neurosurgery 5:883–888 (1992).

Maggio, J., et al., "Reversible in vitro growth of Alzheimer disease –amyloid plaques by deposition of labeled amyloid peptide" Proc. Natl. Acad. Sci. U.S.A. 89:5462–5466 (1992).

Majocha, et al., "Monoclonal Antibody to Embryonic CNS Antigen A2B5 Provides Evidence for the Involvement of Membrane Components at Sites of Alzheimer Degeneration and Detects Sulfatides as Well as Gangliosides," Journal of Neurochemistry 53(3):953–961 (1989).

Majocha, et al., "Immunostaining of Neurofilament Protein in Human Postmortem Cortex: A Sensitive an Specific Approach to the Pattern Analysis of Human Cortical Cytoarchitecture," Canadian Journal of Biochemistry and Cell Biology 63:577–584 (1985).

Mann, et al., "Cerebral Amyloidosis, Ageing and Alzheimer's Disease; A contribution From Studies on Down's Syndrome," Neurobiol. Aging 10:397–399 (1989).

Manning, et al., "Identification in Rodents and other Species of an mRNA Homologous to the Human –Amyloid Precursor," Molecular Brain Research 3:293–298 (1988).

Mansour, et al., "Disruption of the proto–oncogene int–2 in mouse embryo–derived stem cells: a general strategy for targeting mutations to non–selectable genes," Nature 336:348–352 (1988).

Marotta, et al., "Overexpression of Amyloid Precursor Protein A4 (–Amyloid) Immunoreactivity in Genetically Tansformed Cells: Implications for a Cellular Model of Alzheimer Amyloidosis," Proceedings of the National Academy of Science (U.S.A.) 86:337–341 (1989).

Martin, et al. "Intracellular Accumulation of β–Amyloid in Cells expressing the swedish Mutant amyloid Precursor Protein," J. Biol. Chem. 270:26727–26730 (1994).

Martin, et al., "Amyloid Precursor Protein in Aged Nonhuman Primates," Proceedings of the National Academy of Science (U.S.A.) 88:1461–1465 (1991).

Maruyama, et al., "Formation of Amyloid–Like Fibrils in COS Cells Overexpressing Part of the Alzheimer Amyloid Protein Precursor," Nature 347:566–569 (1990).

Marx, "Alzheimer's Research Moves to Mice," Science 253:266–267 (1991).

Marx, "Mutation Identified as a Possible Cause of Alzheimer's Disease" Science 251:876–877 (1991).

Marx, "Major Setback for Alzheimer's Models," Science 255:1200–1202 (1992).

Masliah, et al., "An Antibody Against Phosphorylated Neurofilaments Identifies a Subset of Damaged Association Axons in Alzheimer's Disease," American Journal of Pathology 142:871–882 (1993).

Masliah, et al., "Cortical and Subcortical Patterns of Synaptophysinlike Immunoreactivity in Alzheimer's Disease" Am. J. Path. 138:235–246 (1991).

Masliah, et al., "Localization of amyloid precursor protein in GAP43–immunoreactive aberrant sprouting neurites in Alzheimer's disease," Brain Research 574:312–316 (1992).

Masliah, et al., "Immunoelectron microscopic study of synaptic pathology in Alzheimer's disease," Acta Neuropath. 81:428–433 (1991).

Masliah and Terry, "Role of Synaptic Pathology in the Mechanisms of Dementia in Alzheimer's Disease," Clinical Neuroscience 1:192–198 (1993).

Masliah, et al., "Re–Evaluation of the Structural Organization of Neuritic Plaques in Alzheimer's Disease," J. Neuropath. Exp Neurol. 52:619–632 (1993).

Masters, et al., "Amyloid Plaque Core Protein in Alzheimer Disease and Down Syndrome," Proceedings of the National Academy of Science (U.S.A.) 82:4245–4249 (1985).

Matsunaga, A., et al., "Effect of simvastatin on receptor mediated metabolism of low density lipoprotein in guinea pigs" Atherosclerosis 90:31–37 (1991).

Maue, et al., "Neuron–Specific Expression of the Rat Brain Type II Sodium Channel Gene Is Directed by Upstream Regulatory Elements," Neuron 4:223–231 (1990).

McConlogue, et al., "Transgenic Mice Expressing Human Alzheimer's –Amyloid Precursors Protein Produce High Amounts of –Peptide," Neurobiol. Aging 15:S1 Abstract 49 (1994).

McDonald and Nemeroff, "Neurotransmitters and Neuropeptides in Alzheimer's Disease," Psychiatric Clinics of North America 14:421–422 (1991).

McDuff and Sumi, "Subsortical degeneration in Alzheimer's disease," Neurobiol. 35:123–126 (1985).

McGeer, et al., "Reactions of the Immune System in Chronic Degenerative Neurological Diseases," Canadian Journal of Neurological Sciences 18:376–379 (1991).

McGeer, et al., "Distribution of clusterin in Alzheimer brain tissue," Brain Res. 579:337–341 (1992).

McGeer, et al., "Immune System Response in Alzheimer's Disease," Canadian Journal of Neurological Sciences 16:516–527 (1989).

McGeer, et al., "Detection of the membrane inhibitor of reactive lysis (CD59) in diseased neurons of Alzheimer brain," Brain Res. 544:315–319 (1991).

McLean, I., et al., "Periodate–Lysine–Paraformaldehyde Fixative A New Fixative for Immunoelectron Microscopy" J. Histochem. Cytochem. 22(12):1077–1083 (1974).

Meena–Leist and Parker, "Amyloid Deposition in Alzheimer's Disease," Ann. cli. Lab. Sci., 23:173–177 (1993).

Miller, et al., "Peptide Compositions of the Cerebrovascular and Senile Plaque Core Amyloid Deposits of Alzheimer's Disease," Archives Biochem. Biophys. 301(1):41–52 (1993).

Mistry, et al., "Neurochemistry of Aging. 1. Toxins for an Animal Model of Alzheimer's Disease," J Med Chem 29:376–380 (1986).

Mohr, et al., "Neurotransmitter Replacement Therapy in Alzheimer's Disease," Journal of Psychiatry & Neuroscience 19:17–23 (1994).

Moran, et al. "Age–Related Learning Deficits in Transgenic Mice Expressing the 751–Amino Acid Isoform of Human β–Amyloid Precursor Protein," Proc. Natl. Acad. Sci. USA, 92: 5341–5345 (1995).

Morris, "Spatial Localization Does Not Require the Presence of Local Cues," Learn Motivat. 12:239–260 (1981).

Mucke, et al., "Synaptotrophic effects of human amyloid B protein precursors in the cortex of transgenic mice," Brain Res. 666:151–167 (1994).

Mullan, et al., "A pathogenic mutation for probable Alzheimer's disease in the APP gene at the N–terminus of –amyloid," Nature Genet. 1:345–347 (1992).

Muller, et al. "Behavioral and Anatomical Deficits in Mice Homozygous for a Modified β–Amyloid Precursor Protein Gene," Cell 79: 755–765 (1994).

Mullins, J., et al., "Transgenesis in Nonmurine Species" Hypertension 22:630–633 (1993).

Mullis and Faloona, "Specific Synthesis of DNA in Vitro via a Polymerase–Catalyzed Chain Reaction," Methods Enzymol. 155:335–350 (1987).

Murray, J., et al., "Production of transgenic merino sheep by microinjection of ovine metallothionein–ovine growth hormone fusion genes" Reprod. Fertil. Dev. 1(2):147–155 (1989) (abstract only).

Murrell, et al., "A Mutation in the Amyloid Precursor Protein Associated with Hereditary Alzheimer's Disease," Science 254:97–99 (1991).

Nitsch, et al., "Release of Alzheimer Amyloid Precursor Derivatives Stimulated by Activation of Muscarinic Acetylcholine Receptors," Science 258:304–307 (1992).

Nitsch, et al., Proceedings of the Eighth Meeting of the International Study Group on the Pharmacology of Memory Disorders Associated with Aging, Zurich, Switzerland 204–212 (1995).

Oltersdorf, et al., "The Alzheimer Amyloid Precursor Protein," J. Biol. Chem. 265:4492–4497 (1990).

Olton and Samuelson, "Animal Behavior Processes," J. Exp. Psychol. 2:97–116 (1976).

Palmiter, et al., "Dramatic growth of mice that develop from eggs microinjected with metallothionein–growth hormone fusion genes," Nature 300:611 (1982).

Palmiter, "Germ–Like Transformation of Mice," Annual Review of Genetics 20:465–499 (1986).

Patterson et al., "Mapping of the Gene Encoding the –Amyloid Precursor Protein and its Relationship to the Down Syndrome Region of Chromosome 21," Proceedings of the National Academy of Science (U.S.A.) 85: 8266–8270 (1988).

Pearson and Choi, "Expression of the human –amyloid precursor protein gene from a yeast artificial chromosome in transgenic mice," Proc. Natl. Acad. Sci. USA 90:10578–10582 (1993).

Pericak–Vance, et al., "Genetic Linkage Studies in Alzheimer's Disease Families," Experimental Neurology 102:271–279 (1989).

Perry, et al., "Necropsy Evidence of Central Cholinergic Deficits in Senile Dementia," Lancet 1:189 (1977).

Perry, "The cholinergic hypothesis—ten years on," British Medical Bulletin 42:63–69 (1986).

Pittendrigh, et al., "A functional analysis of circadian pacemaker in nocturnal rodents," J. of Comparative Physiol. 106:291–331 (1976).

Podlisny, et al., "Gene Dosage of the Amyoid Precursor Protein in Alzheimer's Disease," Science 238:669–671 (1987).

Podlisny, et al., "Syntheic Amyloid –Protein Fails to Produce Specific Neurotoxicity in Monkey cerebral Cortex" Neurobiology of Aging 13: 561–567 (1992).

Ponte, et al., "A New A4 Amyloid mRNA Contains a Domain Homologous to Serine Proteinase Inhibitors," Nature 331:525–527 (1988).

Popko, et al., "Myelin Deficient Mice: Expression of Myelin Basic Protein and Generation of Mice with Varying Levels of Myelin," Cell 48:713–721 (1987).

Potempska, et al., "Purification and Tissue Level of the –Amyloid Peptide Precursor of Rat Brain," J. of Biol. Chem. 266:8464–8469 (1991).

Potter, et al., "Enhancer–dependent expressionof human K immunoglobulin genes introduced into mouse pre–B lymphocytes by electroporation," Proc. Natl. Acad. Sci. USA 81:7161 (1984).

Price, et al., "Alzheimer's Disease and Down's Syndrome," Annals of the New York Academy of Sciences 145–164 (1982).

Price, et al., "Alzheimer disease and the prion disorders amyloid –protein and prion protein amyloidoses," Proc. Natl. Acad. Sci. USA 90:6381–6384 (1993).

Price, et al., "Cellular and Molecular Biology of Alzheimer's Disease," BioAssays 10(2&3):69–74 (1989).

Price, et al., "Amyloidosis in aging and Alzheimer's disease," Am. J. Pathol. 141:767–772 (1992).

Prinz, et al., "Sleep, EEG and Mental Function Changes in Senile Dementia of the Alzheimer's Type," Neurobiol. Aging 3:361–370 (1982).

Pursel, V., et al., "Integration, expression and germ–line transmission of growth–related genes in pigs" J. Reprod. Fertil. Suppl. 41:77–87 (1990) (abstract only).

Pursel, V., et al., "Expression and performance in transgenic pigs" J. Reprod. Fertil. Suppl. 40:235–245 (1990) (abstract only).

Pursel, V., et al., "Progress on gene transfer in farm animals" Vet. Immunol. Immunopathol. 17(1–4):303–312 (1987) (abstract only).

Pursel, V., et al., "Genetic engineering of livestock" Science 244(4910):1281–1288 (1989) (abstract only).

Qiagen, Inc., (Publishers) The Qiagenologist, Application Protocols, 3rd edition, Chatsworth, CA.

Quon, et al., "Formation of –Amyloid Protein Deposits in Brains of Transgenic Mice," Nature 352:239–241 (1991).

Ray, et al., "Ectopic expression of a c–kitw42 minigene in transgenic mice: recapitulation of W phenotypes and evidence for c–kit function in melanoblast progenitors," Genes and Development 5:2265–2273 (1991).

Readhead, et al., "Expression of a Myelin Basic Protein Gene in Transgenic Shiverer Mice: Correction of the Dysmyelinating Phenotype," Cell 48:703–712 (1987).

Reddy, et al., "The Genome of Simian Virus 40," Science 200:494–502 (1978).

Reisberg, "Alzheimer's Disease," (Editors, The Free Press, New York & London) (1993).

Rexroad, C., et al., "Insertion, expression and physiology of growth–regulating genes in ruminants" J. Reprod. Fertil. Suppl. 41:119–124 (1990) (abstract only).

Rexroad, C., et al., "Production of transgenic sheep with growth–regulating genes" Mol. Reprod. Dev. 1(3):164–169 (1989).

Rexroad, C., et al., "Transferrin–and albumin–directed expression of growth–related peptides in transgenic sheep" J. Anim. Sci. 69(7):2995–3004 (1991) (abstract only).

Robakis, et al., "Molecular Cloning and Characterization of a cDNA Encoding the Cerebrovascular and the Neuritic Plaque Amyloid Peptides," Proceedings of the National Academy of Science (U.S.A.) 84:4190–4194 (1987).

Rockenstein, et al. "Levels and Alternate Splicing of Amyloid β Protein Precursor (APP) Transcripts in Brains of APP Transgenic Mice and Humans with Alzheimer's Disease," J. Bio. Chemistry 270(47):28257–28267 (1994).

Rodriguez–Echenique, C., et al., "Effects of Policosanol Chronically Administered in Male Monkeys (MACACA Arctoides)" Fd. Chem. Toxic. 32(6):565–575 (1994).

Rumble, et al., "Amyloid A4 Protein and Its Precursor in Down'Syndrome and Alzheimer'Disease," New England J. Med. 320:1446–1452 (1989).

Rylett, et al., "Evidence for High Affinity Choline Transport in Synaptosomes Prepared from Hippocampus and Neocortex of Patients with Alzheimer's Disease," Brain Res 289:169–175 (1983).

Saido, et al., "Spatial Resolution of the Primary –Amyloidogenic ProcessInduced in Postischemic Hippocampus," J. Biol. Chem. 289:15253–15257 (1994).

Saitoh, et al., "Secreted Form of Amyloid Protein Precursor is Involved in the Growth Regulation of Fibroblasts," Cell 58:615–622 (1989).

Sajdel–Sulkowska, "RNA Synthesis in the Nondemented and Alzheimer's Disease Portmortem Brain," J.Neuropathol. Exp. Neurol. 48:327 (1989).

Sakimura, et al., "Partial Purification and Characterization of Messenger RNA Coding 14–3–2 Protein from Rat Brain," Journal of Neurochemistry 39(2):366–370 (1982).

Sakimura, et al., "The structure and expression of neuron-–specific enolase gene," Gene 60:103–113 (1987).

Salbaum, et al., "The promoter of Alzheimer's disease amyloid A4 precursor gene," EMBO J. 7:2807–2813 (1988).

Sambrook et al., Molecular Cloning: A Laboratory Manual (Cold Spring Harbor Laboratory, Cold Spring Harbor, NY 1989).

Sander, M., et al., "The role of the adrenal gland in hypertensive transgenic rat TGR(mREN2)27" Endocrinology 131(2):807–814 (1992) (abstract only).

Sandhu, et al., "Expression of the Human –Amyloid Protein of Alzheimer's Disease Specifically in the Brains of Transgenic Mice," The Journal of Biological Chemistry 266(32): 21331–21334 (1991).

Saper and German, "Hypothalamic pathology in Alzheimer's disease," Neuro. Letters 74:364–370 (1987).

Sasahara, et al., "PDGF B–Chain in Neurons of the Central Nervous System, Posterior Pituitary, and in a Transgenic Model," Cell 64:217–227 (1991).

Satlin, et al., "Circadian Temperature and Locomoter Activity Rhythms in Alzheimer's Disease," Neurobiol. Aging 11:337 (1990).

Scangos, et al., "Gene Transfer into Mice," Adv. in Genet. 24:285–322 (1987).

Schellengberg, et al., "Genetic Linkage Evidence for a Familial Alzheimer's Disease Locus on Chromosome 14," Science 258:668–670 (1992).

Schneider, "Biotechnology's Cash Cow," The New York Times Magazine 44 (Jun. 12, 1988).

Schilling, et al., "Synthesis and characterization of the Kunitz protease–inhibitor domain of the –amyloid precursor protein," Gene 98:225–230 (1991).

Schwagerl, et al., "Elevated Levels of the Endosomal–Lysosomal Proteinase Cathepsin D in Cerevrospinal Fluid in Alzheimer Disease," Journal of Neurochemistry 64:443–446 (1995).

Sedlak, "Athena Neuroscience/Eli Lily & Academic Team Develop Alzheimer's Lab Mouse Model," Genetic Engineering News p. 1 (Mar. 1, 1995).

Selkoe, "Normal and Abnormal Biology of the –Amyloid Precursor Protein," Ann. Rev. Neurosi. 17:489–517 (1994).

Selkoe, "In the Beginning . . . ", Nature 354:432–433 (1991).

Selkoe, "Amyloid Protein and Alzheimer's Disease," Scientific American 265(5):68–76 (1991).

Selkoe, "Biochemistry of Altered Brain Proteins in Alzheimer's Disease," Ann. Rev. Neurosci. 12:463–490 (1989).

Selkoe D., "Normal and Abnormal Biology of the –Amyloid Precursor Protein" Annu. Rev. Neurosi. 17:489–517 (1994).

Selkoe, "Physiological Production of the β –Amyloid Protein and the Mechanism of Alzheimer'Disease," Trends in Neuroscience 16:403–409 (1993).

Seubert, et al., "Secretion of –amyloid precursor protein cleaved at the amino terminus of the –amyloid peptide," Nature 361:260–263 (1993).

Seubert, et al., "Isolation and quantification of soluble Alzheimer's –peptide from biological fluids," Nature 359:325–327 (1992).

Shoji, et al., "Production of the Alzheimer Amyloid Protein by Normal Proteolytic Processing," Science 258:126–129 (1992).

Shananhan, C., et al., "Regulation of expression of a sheep metallothionein 1 a–sheep growth hormone fusion gene in transgenic mice" Mol. Cell. Biol. 9(12):5473–5479 (1989) (abstract only).

Sims, et al., "Presynaptic Cholinergic Dysfunctionin Patients with Dementia," J. Neurochem. 40: 503–509 (1983).

Sims, et al., "Glucose Metabolism and Acetylocholine Synthesis in Relation to Neuronal Activityin Alzheimer's Disease," Lancet 1:333–336 (1980).

Sirinathsinghji, "Transgenic Models of Alzheimer's Disease" Current Research In Alzheimer's Disease 3(2): 47–56.

Sisodia, et al., "Evidence That –Amyloid Protein in Alzheimer's Disease Is Not Derived by Normal Processing," Science 48:492–495 (1990).

Smith, et al., "Excess brain protein oxidation and enzyme dysfunction in normal aging and in Alzheimer disease," Proc. Natl. Acad. Sci. USA 88:10540–10543 (1991).

Smith, et al., "Carbonyl–Related Posttranslational Modification of Neurofilament Protein in the Neurofibrillary Pathology of Alzheimer's Disease," J. Neurochemistry 64:2660–2666 (1995).

Southern and Berg, "Transformation of Mammalian Cells to Antibiotic Resistance with a Bacterial Gene Under Control of the SV40 Early Region Promoter," J. Mol. Appl. Gen. 1:327–341 (1982).

Sparks, D., et al., "Temporal Sequence of Plaque Formation in the Cerebral Cortex of Non–Demented Individuals" J. Neuropathol Exp Neurol 52(2):135–142 (1993).

Spencer, et al., "Behavioral Impairments Related to Cognitive Dysfunction in the Autoimmune New Zealand Black Mouse," Behavioral Neuroscience 100(3):353–358 (1986).

Spetch, et al., "A program that stimulates random choices in radial arm mazes and similar choice situations" Behavior Research Methods & Instrumentation 12(3):377–378 (1980).

St. George–Hyslop, et al., "The Genetic Defect Causing Familial Alzheimer's Disease Maps on Chromosome 21," Science 235:885–890 (1987).

St. George–Hyslop, et al., "Absence of Duplication of Chromosome 21 Genes in Familial and Sporadic Alzheimer's Disease," Science 238:664–666 (1987).

St. George–Hyslop, et al., "Genetic evidence for a novel familial Alzheimer's disease locus on chromosome 14," Nature Genetics 2:330–334 (1992).

Stanley, et al., "The structure and expression of the murine gene encoding granulocyte–macrophage colony stimulating factor: evidence for utilisation of alternative promoters," EMBO J. 4:2569–2573 (1985).

Stopa, et al., "Human suprachiasmatic nuclei in Alzheimer's disease," J. Neuropathol. Exp. Neurol. 48:327 (1989).

Su, J., et al., "Early phosphorylation of tau in Alzheimer's disease occurs at Ser–202 and is preferentailly located within neurites" Neuroreport 5(17):2358–2362 (1994).

Suzuki, et al., "An Increased Percentage of Long Amyloid Protein Secreted by Familial Amyloid Protein Precursor ( APP717) Mutants," Science 264:1336–1340 (1994).

Swaab, et al., "The Suprachiasmatic Nucleus of the Human Brain in Relation to Sex, Age and Senile Dementia," Brain Res. 342:37–44 (1985).

Swanson, M., et al., "High level expression of human apolipoprotein A–I in transgenic rats raises total serum high density lipoprotein cholesterol and lowers rat apolipoprotein A–I" Transgenic Res. 1(3):142–147 (1992) (abstract only).

Swanson, et al., "Novel developmental specificity in the nervous system of transgenic animals expressing growth hormone fusion genes," Nature 317:363–366 (1985).

Tamaoka, et al., "Identification of a stable fragment of the Alzheimer amyloid precursor containing the –protein in brain microvessels," Proc. Natl. Acad. Sci. U.S.A. 89:1345–1349 (1992).

Tanzi, "Clinical Implications of Basic Research: A Promising Animal Model of Alzheimer's Disease," New England J. Med. 332:1512–1513 (1995).

Tanzi, et al., "The Amyloid Protein Gene is not Duplicated in Brains from Patients with Alzheimer's Disease," Science 238:666–669 (1987).

Tanzi, et al., "The Genetic Defect in Familial Alzheimer's Disease is not Tightly Linked to the Amyloid –Protein Gene," Nature 329:156–157 (1987).

Tanzi, et al., "Molecular Genetic Approaches to Alzheimer's Disease," Trends in Neuroscience 12(4):152–158 (1989).

Tanzi, et al., "Amyloid Protein Gene: cDNA, mRNA Distribution and Genetic Linkage Near the Alzheimer Locus," Science 235:881–884 (1987).

Tanzi, et al., "Protease Inhibitor Domain Encoded by an Amyloid Protein Precursor mRNA Associated wtih Alzheimer's Disease," Nature 331:528–530 (1988).

Tate–Ostroff et al., "Identification of Cellular and Extracellular Sites of Amyloid Precursor Protein Extracytoplasmic Domain in Normal and Alzheimer Disease Brains," Proceedings of the National Academy of Science (U.S.A.) 86:745–749 (1989).

Thybo, N., et al., "Morphology and function of mesenteric resistance arteries in transgenic rats with low–renin hypertension" J. Hypertens. 10(10):1191–1196 (1992) (abstract only).

Tooyama, et al., "Acidic fibroblast growth factor–like immunoreactivity in brain of Alzheimer patients," Neuroscience Letters 121:155–158 (1991).

Tooyama, et al., "Immunohistochemical Study of 2 Macroglobulin Receptor in Alzheimer and Control Postmortem Human Brain," Molecular and Chem. Neuropathol. 18:153–160 (1993).

Trojanowski, et al., "Altered Tau and Neurofilament Proteins in Neuro–Degenerative Diseases: Diagnostic Implications for Alzheimer's Disease and Leqy Body Dementias," Brain Pathology 3:45–54 (1993).

Tsujita, Y., et al., "Hypolipidemic Effects in Dogs of ML–236B, A Competitive Inhibitor of 3–Hydroxy–3–Methylglutaryl Coenzyme A Reductase" Atherosclerosis 32:307–313 (1979).

Tsujita, Y., et al., "CS–514, a competitive inhibitor of 3–hydroxy–3–methylglutaryl coenzyme A reductase: tissue–selective inhibition of sterol synthesis and hypolipidemic effect on various animal species" Biochim. Biophys. Acta 877:50–60 (1986).

Ueda, et al., "Molecular cloning of cDNA encoding an unrecognized component of amyloid in Alzheimer disease," Proc. Natl. Aca. Sci. USA 90:11282–11286 (1993).

Van Broeckhaven et al., "Mapping of a gene predisposing to early–onset Alzheimer's disease to chromosome 14q24.3," Nature Genetics 2:335–339 (1992).

Van Broeckhoven, et al., "Amyloid Protein Precursor Gene and Hereditary Cerebral Hemorrhage with Amyloidosis (Dutch)," Science 248:1120–1122 (1990).

Van Hoesan, et al., Hippocampus 1:1–8 (1991).

Velander, W., et al., "High–level expression of a heterologous protein in the milk of transgenic swine using the cDNA encoding human protein C" Proc. Natl. Acad. Sci. USA 89(24):12003–12007 (1992) (abstract only).

Vickers, J., et al., "Alterations in Neurofiliment Protein Immunoreactivity in Human Hippocampal Neurons Related to Normal Aging and Alzheimer's Disease" Neuroscience 61(1):1–13 (1994).

Vincent, et al., "Embryonic expression of a Drosophila src gene: alternate forms of the protein are expressed in segmental stripes and in the nervous system," Genes & Devel. 3:334–347 (1989).

Vize, P., et al., "Introduction of a porcine growth hormone fusion gene into transgenic pigs promotes growth" J. Cell. Sci. 90(Pt 2):295–300 (1988) (abstract only).

Wall, R., et al., "High–level synthesis of a heterologous milk protein in the mammary glands of transgenic swine" Proc. Natl. Acad. Sci. USA 88(5):1696–1700 (1991) (abstract only).

Wang, et al., "Quantitation of mRNA by the polymerase chain reaction," Proc. Natl. Acad. Sci. U.S.A. 86:9717–9721 (1989).

Weidemann, et al., "Identification, Biogenesis, and Localization of Precursors of Alzheimer's Disease A4 Amyloid Protein," Cell 57:115–126 (1989).

Weidle, U., et al., "Genes encoding a mouse monoclonal antibody are expressed in transgenic mice, rabbits and pigs" Gene 98(2):185–191 (1991) (abstract only).

Wieghart, M., et al., "Production of transgenic pigs harbouring a rat phosphoenolpyruvate carboxykinase–bovine growth hormone fusion gene" J. Reprod. Fertil. Suppl. 41:89–96 (1990) (abstract only).

Whitehouse, et al., "Alzheimer's Disease and Senile Dementia: Loss of Neurons in the Basal Forebrain," Science 215:1237–1239 (1982).

Wirak, et al., "Deposits of Amyloid Protein in the Central Nervous System of Transgenic Mice," Science 253:323–325 (1991).

Wirak, et al., "Age–Associated Inclusions in Normal and Transgenic Mouse Brain," Science 255:1443–1445 (1992).

Wirak, et al., "Regulatory Region of Human Amyloid Precursor Protein (APP) Gene Promotes Neuron–Specific Gene Expresson in the CNS of Transgenic Mice," The EMBO J. 10:289–296 (1991).

Wirak, et al., "Regulatory region of human amyloid precursor protein (APP) gene promotes neuron–specific gene expression in the CNS of transgenic mice," The EMBO-Journal 10(2):289–296 (1991).

Wisniewski, et al. "Alzheimer's Disease and Soluble Aβ," Neurobiology of Aging 15: 143–152 (1994).

Witting, et al., "Alterations in the Circadian Rest–Activity Rhythm in Aging and Alzheimer's Disease," Biol. Psychiatry 27:563–572 (1990).

Wolozin, et al., "A Neuronal Antigen in the Brains of Alzheimer Patients," Science 232:648 (1986).

Wood, et al., "Cytokine indices in Alzheimer's temporaral cortex: no charges in mature IL–1 or IL–1RA but increases in the associated acute phase proteins IL–6, 2–macroglobulin and C–reactive protein," Brain Research 629:245–252 (1993).

Yamaguchi, T., et al., "Zonal distribution and regulation of adrenal renin in a transgenic model of hypertension in the rat" Endocrinology 131(4):1955–1962 (1992) (abstract only).

Yamaguchi, et al., "Transgenic mice for the amyloid precursor protein 695 isoform have impaired spatial memory," NeuroReport 2:781–784 (1991).

Yamamoto, et al., "Effects of Indeloxazine Hydrochloride on Cognitive Disturbance in Cycloheximide–Treated Mice," Journal of Pharmacy and Pharmacology 41:284–286 (1989).

Yankner, et al., "Neurotoxicity of a fragment of the amyloid precursor associated with Alzheimer's disease," Science 245:417–420 (1989).

Yasuhara, et al., "Midkine, A Novel Neurotrophic Factor, Is Present in Senile Plaques of Alzheimer Disease," Biochem. and Biophys. Res. Comm. 192:246–251 (1993).

Yoshikai, et al., "Genomic Organization of the Human Amyloid Beta–Protein Precursor Gene," Gene 102:257–263 (1990).

Yoshikai, et al., "Genomic Organization of the Human Amyloid Beta–Protein Precursor Gene," Gene 102:291–292 (1991).

Yoshikawa, et al., "Degeneration in vitro of post–mitotic neurons overexpressing the Alzheimer's amyloid protein precursor," Nature 359:64–67 (1992).

Zhao, J., et al., "–Secretase Processing of the –Amyloid Precursor Protein in Transgenic Mice is Efficienct in Neurons but Inefficient in Astrocytes" The Journal of Biological Chemistry 271(49):31407–31411 (1996).

Zimmer and Gruss, "Production of chimaeric mice containing embryonic stem (ES) cells carrying a homoeobox Hox 1.1 allele mutated by homologous recombination," Nature 338:150–153 (1989).

Zornetzer, "Rapid Forgetting in Aged Rats," Behav. Neur. Biol. 36:49–60 (1982)Chemical Industry Institute of Toxicology, 1987 Annual Report.

"Alzheimer's assault," Science 255(5048):1059 (1992).

Abraham, et al., "A calcium–activated protease from Alzheimer's disease brain cleaves at the N–terminus of the amyloid—protein," Biochem. Biophys. Res. Comm. 174:790–96 (1991).

Ali, et al., "More transgenic mouse studies of Alzheimer amyloid precursor (AAP) proteins and derivatives," Society for Neuroscience Abstracts, 18:1445 (presentation 616.9) (1992).

Allison, et al., "Diabetes in transgenic mice resulting from over–expression of class I histocompatibility molecules in pancreatic B cells," Nature (333)6173:529–33 (1988).

Antal, et al., "Animal models of Alzheimer's, Parkinson's and Huntington's disease, A minireview," Neurobiology (Bp) 1(2):101–22 (1993).

Barton, "Alteration in brain presenilin 1 mRNA expression in early onset familial Alzheimer's disease," Neurodegeneration 5:213–18 (1996).

Blass, "Immunologic treatment of Alzheimer's disease," The New England Journal of Medicine 341(22):1694–95 (1999).

Brewer, "A G to C transversion in codon 258 of the –subunit of –hexosaminidase A in an infant Tay–Sachs disease patient," Human Mutation 2:496–97 (1993).

Brice, et al., "Absence of the amyloid precursor protein gene mutation (APP717: Val–>lle) in 85 cases of early onset Alzheimer's disease," J Neurol, Neurosurg, Psychiatry 56(1):112–3 (1993).

Cairns, et al., " A4 protein deposition in familial Alzheimer's disease with the mutation in codon 717 Of the beta A4 amyloid precursor protein gene and sporadic Alzheimer's disease," Neurosci Lett. 149(2):137–40 (1993).

Carlson, et al., "Genetic modification of the phenotypes produced by amyloid precursor protein overexpression in transgenic mice," Human Molecular Genetics 6(11):1951–59 (1997).

Chapman, et al., "Impaired synaptic plasticity and learning in aged amyloid precursor protein trasgenic mice," Nature Neuroscience 2(3):271–76 (1999).

Crawford, et al., "Alzheimer's disease untangled," BioEssays (14)11:729 (1992).

Davis, et al., An Alzheimer's disease–linked PS1 variant rescus the development abnormalities of PS1–deficient embryos, Neuron 20:603–09 (1998).

De Strooper, et al., "Study of the synthesis and secretion of normal and artificial mutants of murine amyloid precursor protein (APP): cleavage of APP occurs in a late compartment of the default secretion pathway," J Cell Biol. 121(2):295–304 (1993).

Dovey, et al., "Cells with a familial Alzheimer's disease mutation produce authentic Beta–peptide," Neuroreport;4(8):1039–42 (Aug. 1993).

Duff, "Alzheimer transgenic mouse models come of age," TINS 20(7):279–80 (1997).

Duff, "Modeling Alzheimer's disease in transgenic mice," J Florida M.A. 91(9):625–28 (1994).

Duff, "Recent work on Alzheimer's disease transgenic," Curr Opin Biotech 9:561–64 (1998).

Duff, "Transgenic models for Alzheimer's disease," Neuropathology and Applied Neurobiology 24:101–03 (1998).

Duff, et al., "Increased amyloid–42(43) in brains of mice expressing mutant presenilin 1," Nature 383:710–13 (1996).

Erickson, "Model mice. Transgenic animals and Alzheimer's research," Sci Am 265(3):34 (1991).

Felsenstein, et al, "Processing of the –amyloid precursor protein carrying the familial, Dutch–type, and a novel recombinant C–terminal mutation," Neurosci Lett. 152:185–89 (1993).

Fidani, et al., "Screening for mutations in the open reading frame and promoter of the –amyloid precursor protein gene in familial Alzheimer's disease: Identification of a further family with APP717 Val—>lle," Hum Mol Genet. 1(3):165–68 (1992).

Fisher, et al., "Expression of the amyloid precursor protein gene in mouse oocytes and embryos," Proc Natl Acad Sci USA 88(5):1779–82 (1991).

Forss–Petter, et al., "Transgenic mice expressing –galactosidase in mature neurons under neuron–specific enolase promoter control," Neuron 5(2):187–97 (1990).

Francis, et al., "Animal and drug modeling for Alzheimer synaptic pathology," Progress in Neurobiology 39:517–45 (1992).

Fraser, et al., "Biochemistry and Alzheimer's disease amyloid plaques," Clin Biochem 46:339–49 (1993).

Frautschy, et al., "Microglial response to amyloid plaques in APPsw transgenic mice," American Journal of Pathology 152(1):307–17 (1998).

Fukuchi, et al., "High levels of circulating –amyloid peptide do not cause cerebral –amyloidosis in transgenic mice," American Journal of Pathology 149(1):219–27 (1996).

Fukuchi, et al., "Intestinal –amyloidosis; transgenic mice" Society for Neuroscience Abstracts 19:1035 (1993).

Gallagher, et al., "Animal models of normal aging: Relationship between cognitive decline and markers in hippocampal circuitry," *Behav Brain Res.* 57(2):155–62 (1993).

Gandy, et al., "Amyloidogenesis in Alzheimer's disease: some possible therapeutic opportunities," *Trends Pharmacol Sci.* 13(3):108–13(1992).

Glenner, et al., "Alzheimer's disease and Down's Syndrome: Sharing of unique cerebrovascular amyloid fibril protein," *Biochem. Biophys. Res. Commun.* 122:1131–35 (1984).

Goding, "Production and application of monoclonal antibodies in cell biology, biochemistry and immunology," in *Monoclonal Antibodies: Principles and Practice*, Ch. 3, pp. 56–74, (Academic Press, London 1984).

Golde, et al., "Production of amyloid protein from normal amyloid –protein precursor ( APP) and the mutated APPS linked to familial Alzheimer's disease," *Ann. N Y Acad. Sci.*, 695:103–08 (1993).

Goverman, et al., "Transgenic mice that express a myelin basic protein–specific T cell receptor develop spontaneous autoimmunity," *Cell* 72:551–560 (1993).

Greaves, et al., "A transgenic mouse model of sickle cell disorder," *Nature* (343):183–85 (1990).

Greenberg, "Yet more transgenic mouse studies of Alzheimer amyloid precursor (APP)," *Society for Neuroscience Abstracts* 19:1035 (1993).

Greenberg, et al., "Transgenic mouse studies for Alzheimer amyloid precursor (AAP) proteins and derivatives," *Society for Neuroscience Abstracts*, vol. 18:1445 (presentation 616.7) (1992).

Haass, et al., "The Swedish mutation causes early–onset Alzheimer's disease by –secretase cleavage within the secretory pathway," *Nature Medicine* 1(12):1291–96 (1995).

Haass, et al., "Amyloid –peptide is produced by cultured cells during normal metabolism," *Nature* 359:322–325 (1992).

Hammer, et al., "Partial correction of murine hereditary growth disorder by germ–line incorporation of a new gene," *Nature* 311:65–67 (1984).

Hardy, "New insights into the genetics of Alzheimer's disease," *Ann Med* 28(3):255–58 (1996).

Hardy, "The Alzheimer family of disease: many etiologies, one pathogenesis?," *Proc Natl Acad Sci USA* 94(6):2095–97 (1997).

Hoewsche, et al., "The 5'–flanking region of the rat synapsin I gene directs neuron–specific and developmentally regulated reporter gene expression in transgenic mice," *J Biol Chem.* 268(35):26494–02 (1993).

Holcomb, et al, "Accelerated Alzheimer–type phenotype in transgenic mice carrying both mutant *amyloid precursor protein* and *presenilin 1* transgenes," *Nature Medicine* 4(1):97–100 (1998).

Holtzman, et al., "Molecular studies in Alzheimer's disease," *Trends Biochem. Sci.*, 16(4):140–4 (1991).

Howland, et al., "Modulation of secreted –amyloid precursor protein and amyloid –peptide in brain cholesterol," *J Biol Chem.* 273(26):16576–82 (1998).

Howland, et al., "Neuron–specific expression of human amyloid precursor protein (APP) in transgenic mice," *Society for Neuroscience Abstracts* 19:1035 (1993).

Hsiao, "A proposed strategic research program for Alzheimer's disease," *Neuorobiology of Aging* 15(2):S112–S115 (1994).

Hsiao, "From prion diseases to Alzheimer's disease," *J. Transm Supple* 49:135–44 (1997).

Hsiao, "Strain dependent and invariant features of transgenic mice expressing Alzheimer amyloid precursor proteins," *Progress in Brain Research* 117:335–41 (1998).

Hsiao, "Transgenic mice expressing Alzheimer amyloid precursor proteins," *Experimental Gerontology* 33(718):883–89 (1998).

Hsiao, "Understanding the biology of –amyloid precursor proteins in transgenic mice," *Neurobiology of Aging* 16(4):705–06 (1995).

Hsiao, et al., "Molecular genetics and transgenic model of Gertsmann–Straussler–Scheinker disease," *Alzheimer Dis Assoc Disord* 5(3):155–62 (1991).

Hsiao, et al., "Spontaneous neurodegeneration in transgenic mice with mutant prior protein," *Science* 250:1587–90 (1990).

Hyman, et al., "Kunitz protease inhibitor–containing amyloid protein precursor immunoreactivity in Alzheimer's disease," *J. Neuropath. Exp. Neurol.* 51:76–83 (1992).

Iadecola, et al., "SOD1 rescues cerebral endothelial dysfunction in mice overexpressing amyloid precursor protein," *Nature Neuroscience* 2(2):157–161 (1999).

Irizarry, et al., "$APP_{sw}$ Transgenic mice develop age–related A deposits and neuropil abnormalities, but no neuronal loss in CA1," *J Neuropathol Exp Neurol.* 56(9):965–73 (1997).

Iwamoto, et al., "Neuroblastoma in a transgenic mouse carrying a metallothionein/ret fusion gene," *Br J Cancer.* 67(3):504–47 (1993).

Jan & Jan, "Receptor–regulated ion channels," *Curr Opin Cell Biol* 9(2):155–60 (1997).

Johnston–Wood, et al., "Amyloid precursor protein processing and A 42 deposition in a transgenic mouse model of Alzheimer disease," *Proc Natl Acad Sci USA* 94(4):1550–55 (1997).

Jones, et al., "Mutation in codon 713 of the amyloid precursor protein gene presenting with Schizophrenia," *Genetics*, 1:306–309 (1992).

Joyner, et al., "Gene targeting: A practical approach," Oxford Press (1993).

Keffer, et al., "Transgenic mice expressing human tumour necrosis factor: A predictive genetic model of arthritis," *EMBO* 10(3):4025–31 (1991).

Kennedy, et al., "Familial Alzheimer's disease. A pedigree with a mis–sense mutation in the amyloid precursor protein gene (amyloid precursor protein 717 Valine—>Glycine)," *Brain* 116 (pt 2):309–24 (1993).

Kennedy, et al., "Only kunitz–inhibitor–containing isoforms of secreted Alzheimer amyloid precursor protein show amyloid immunoreactivity in normal cerebrospinal fluid," *Neurodegeneration* 1:59–64 (1992).

Koliatsos, et al., "Neurotrophic strategies for treating Alzheimer's disease: Lessons from basic neurobiology and animal models," *Ann. N Y Acad. Sci.*, 695:292–99 (1993).

Konig, et al., "Identification and differential expression of a novel alternative splice isoform of the BA4 amyloid precursor protein (App) mRNA in leukocytes and brain microglial cells," *JBC* 267:10804–09 (1992).

Korf, et al., "S–antigen and rodopsin immunoreactions in midline brain neoplasms of transgenic mice: Similarities to pineal cell tumors and certain medulloblastomas in man," *J Neuropathol Exp Neurol.* 49(4):424–37 (1990).

Kozak, "The scanning model for translation: An update," *J. Cell Biology* 108:229–41 (1989).

Kozlowski et al., "The neurotoxic carboxy–terminal fragment of the Alzheimer amyloid precursor binds specifically to a neuronal cell surface molecule: Ph dependence of the neurotoxicity and the binding," *J. Neurosci.*, 12(5):1679–87 (1992).

Kuljis, et al., "Alzheimer–like diffuse amyloid plaques can be induced in transgenic mice expressing human 1–antichymotrypsin," *Soc. Neurosci. Abstr.* 9(2):1035 (1993).

Kumar, "Mutations at codon 717 of the beta–amyloid precursor protein gene are a cause of Alzheimer's disease," *Indian J Exp Biol.* 30(2):156 (1992).

Lamb, et al., "Altered metabolism of familial Alzheimer's disease–linked amyloid precursor protein variants in yeast artificial chromosome transgenic mice," *Human Molecular Genetics* 6(9):1535–41 (1997).

Lamb, et al., "Amyloid production and deposition in mutant *amyloid precursor protein* and *presenilin–1* yeast artificial chromosome transgenic mice," *Nature Neuroscience* 2(8):695–97 (1999).

Lannfelt, et al., "Low frequency of the APP 670/671 mutation in familial Alzheimer's disease in Sweden," *Neurosci Lett.* 153(1):85–7 (1993).

Lavigueur, et al., "High incidence of lung, bone, and lymphoid tumors in transgenic mice overexpressing mutant alleles of the P53 oncogene," *Molecular and Cellular Biology* 9(9):3982–91 (1989).

Lendon, et al., "Exploring the etiology of Alzheimer disease using molecular genetics," *Jama* 277(10):825–31 (1997).

Lieberburg, Abstract 421.15, "Expression of human Alzheimer's amyloid precursor protein in transgenic mice," *Society for Neuroscience Abstracts* 19:1035 (1993).

Luo, et al., "Human amyloid precursor protein ameliorates behavioral deficit of flies deleted for Appl Gene," *Neuron* 9(4):595–605 (1992).

Marx, "New lead to an Alzheimer's mouse?," *Science* 261(5128):1520 (1993).

McPhei, et al., "Neuronal expression of –amyloid precursor protein Alzheimer mutations causes intracellular accumulation of a C–terminal fragment containing both the amyloid and cytoplasmic domains," *J. Biol. Chem.* 272:24743–46 (1997).

Miller, et al., "Alzheimer's disease: Transgenic models to test new chemicals and pharmaceuticals," *Carr Opin Biotechnol* 6:683–686 (1992).

Mucke, et al., High–level neuronal expression of A in wild–type human amyloid protein precursor transgenic mice: Synaptotoxicity without plaque formation, *J. Neuroscience* 20(11):4050–58 (2000).

Mullan, "Familial Alzheimer's disease: Second gene locus located," *BMJ* 305(6862):1108–9 (1992).

Mullan, et al., "Genetic and molecular advances in Alzheimer's disease," *Trends Neurosci.* 16(10):398–403 (1993).

Mullins, et al., "Fulminant hypertension in transgenic rats harbouring the mouse Ren–2 gene," *Nature* 344:541–44 (1990).

Murai, et al., "Twofold overexpression of humn –amyloid precursor proteins in transgenic mice does not affect the neuromotor, cognitive, or neurodegenerative sequelae following experimental brain surgery," *The Journal of Comparative Neurology* 392:428–38 (1998).

Neve, et al., "Brain transplants of cells expressing the carboxyl–terminal fragment of the Alzheimer amyloid protein precursor cause specific neuropathology in vivo," *Proc. Natl. Acad. Sci. USA* 89(8):3448–52 (1992).

Nguyen, et al., "The pathophysiological significance of nondesmoglein targets of pemphigus autoimmunity," *Arch Dermatol.* 134:971–80 (1998).

Nussbaum, et al., "Alzheimer's disease and amyloid protein—In (transgenic) mice and man," *Harefuah* (Hebrew) 123(9):362–64 (1992).

Oltersdorf, et al., "The secreted form of the Alzheimer's amyloid precursor protein with the kunitz domain is protease nexin–oII," *Nature* 341:144–47 (1989).

Palmert, et al., "Soluable derivatives of the B amyloid protein precursor of Alzheimer's disease are labeled by antisera to the B amyloid protein," *Biochem. Biophys. Res. Comm.* 165:182–88 (1989).

Palmert, et al., "The –amyloid protein precursor of Alzheimer disease has soluable derivatives found in human brain and cerebrospinal fluid," *Proc. Natl. Acad. Sci USA* 86:6338–42 (1989).

Pappolla, et al., "Evidence of oxidative stress and in vivo neurotoxicity of –amyloid in transgenic mouse model of Alzheimer's disease," *Amer. J. Path.* 152(4):871–77 (1998).

Pavlin, "Brain amyloid in Alzheimer's disease—A new experimental model," *Neurol Croat* 41(4):227–34 (1992).

Pearson, et al., "Nicotine intake and Alzheimer's disease," *BMJ* 303:361 (1991).

Perraud, et al., "The promoter of the human Cystic Fibrosis transmembrane conductance regulator gene directing SV40 T antigen expression induces malignant proliferation of ependymal cells in transgenic mice," *Oncogene* 5:993–97 (1992).

Price, et al., "Alzheimer's disease–type brain abnormalities in animal models," *Prog Clin Biol Res.* 379:271–87 (1992).

Pulliam, et al., "Use of aggregating brain cultures to study the replication of herpes simplex virus types 1 and 2 in central nervous system tissue," *J. Virol. Met.* 9:301–16 (1984).

Reaume, "Enhanced amyloidogenic processing of the –amyloid precursor protein in gene–targeted mice bearing the Swedish familial Alzheimer's disease mutations and 'humanized' A sequence," *J. Biol. Chem.* 271(38):23380–88 (1996).

Robakis, et al., "An alternative secretase cleavage produces soluable Alzheimer amyloid precursor protein containing a potentially amyloidogenic sequence," *Soc. Neurosci.*, Abstract No. 15.5, (1993).

Roch, et al., "Biologically active domain of the secreted form of the amyloid beta/A4 protein precursor," *Ann N Y Acad. Sci.* 695:194–57 (1993).

Rossor, et al., "Alzheimer's Disease families with amyloid precursor protein mutations," *Ann N Y Acad Sci.* 695:198–202 (1993).

Ryan, et al., "Human sickle hemoglobin in transgenic mice," *Science* 247:566–68 (1990).

Sahasrabudhe, et al., "Release of amino–terminal fragments from amyloid precursor protein reporter and mutated derivatives in cultured cells," *J. Biol. Chem.*, 267(35):25602–8 (1992).

Sarvetnick, et al., "Insulin–dependent diabetes mellitus induced in transgenic mice by ectopic expression of class II MHC and interferon–gamma," *Cell* (52):773–82 (1988).

Savage, et al., "Human amyloid precursor protein expression in trangenic mice as a model of Alzheimer's disease: A search for pathology," *Society for Neuroscience Abstracts* 19:1035 (1993).

Savage, et al., "Turnover of amyloid –protein in mouse brain and acute reduction of its by phorbol ester," Journal of Neuroscience 18(5):1743–52 (1998).

Schenk, et al., "The potential utility of transgenic mice harboring –amyloid precursor protein," Neurobiology of Aging 16(4):711–13 (1995).

Scheuner, et al., "Secreted amyloid –protein similar to that in the senile plaques of Alzheimer's disease is increased in vivo by the presenilin 1 and 2 and APP mutations linked to familial Alzheimer's disease," Nature Medicine 2(8):864–90 (1996).

Scott, et al., "Chimeric prion protein expression in cultured cells and transgenic mice," Protein Science 1:986–97 (1992).

Scott, et al., "Inability to detect beta–amyloid protein precursor mRNA in Alzheimer plaque–associated Microglia," Exp. Neurol., 121(1):113–8 (1993).

Scott, et al., "The processing of native and mutant APP751 in human 293 cells," Neurobiology of Aging Third International Conference on Alzheimer's Disease and Related Disorders 13 (Suppl. 1):310 (1992).

Scott, et al., "Transgenic mice expressing hamster prion protein produce species–specific scrapie infectivity and amyloid plaques," Cell 59:847–857 (1989).

Selkoe, "Alzheimer's disease: Genotypes, phenotype, and treatments," Science 275(5300):630–31 (1997).

Selkoe, "The molecule pathology of Alzheimer's disease," Neurom. 6(4):487–98 (1991).

Selkoe, et al., "–Amyloid precursor protein of Alzheimer disease occurs as 110–to 135–kilodalton membrane–associated proteins in neural and nonneural tissues," Proc. Nat. Acad. Sci. USA 85:7341–45 (1988).

Shiosaka, "Attempts to make models for Alzheimer's disease," Neurosci Res 13(4):237–55 (1992).

Siman, et al., "Processing of the beta–amyloid precursor. Multiple proteases generate and degrade potentially amyloidogenic fragments," J. Biol. Chem., 268(22):16602–9 (1993).

Sisodia, "–amyloid precursor protein cleavage by a membrane–bound protease," Proc Natl Acad Sci USA 89(13):6075–79 (1992).

Sisodia, et al., "Amyloidogenesis in Alzheimer's disease: Basic biology and animal models," Curr Opin Neurobiol 2(5):648–52 (1992).

Smith, et al., "Amyloid–deposition in Alzheimer transgenic mice is associated with oxidative stress," Journal of Neurochemistry 70(5):2212–15 (1998).

Sofroniew, et al., "Transgenic modeling of neurodegenerative events gathers momentum," Trends Neurosci. 14(12):513–14 (1991).

Stacey, et al., "Perinatal lethal osteogenesis imperfecta in transgenic mice bearing an engineered mutant Pro–X1(I) collagen gene," Nature 332:131–36 (1988).

Stout, et al., "Expression of human HPRT in the central nervous system of transgenic mice," Nature 317:250–52 (1985).

Sturchler–Pierrat, et al., "Two amyloid presursor protein transgenic mouse models with Alzheimer disease–like pathology," Proc. Natl. Acad. Sci. 94:13287–92 (1997).

Thinakaran, et al., "Endoproteolysis of presenilin 1 and accumulation of processed derivatives in vivo," Neuron 17:181–90 (1996).

Tomita, et al., "The presenilin in 2 mutation (N141I) linked to familial Alzheimer disease (Volga German families) increases the secretion of amyloid beta protein ending at the 42nd (or 43rd) residue," Proc Natl Acad Sci USA 94(5):2025–30 (1997).

Travis, "New piece in Alzheimer's puzzle," Science 261(5123):828–9 (1993).

Trudel, et al., "c–myc as an inducer of polycystic kidney disease in transgenic mice," Kidney International 39:665–71 (1991).

Usami, et al., "The triplet of lysine residues (Lys724–Lys725–Lys726) of Alzheimer's amyloid precursor protein plays an important role in membrane anchorage and processing," J Neurochem. 61(1):239–46 (1993).

Van Duijn, et al., "Genetic transmission of Alzheimer's disease among families in a dutch population based study," J Med Genet. 30(8):640–46 (1993).

Vidal, et al., "Sequencing of the Alzheimer's APP gene dutch variant (APP–D)," Hum Mutat. 2(6):496–67 (1993).

Wang, et al., "Tissue and development–specific expression of the human phenylalanine hydroxylase/chloramphenicol acetyltransferase fusion gene in transgenic mice," The Journal of Biological Chemistry 267:15105–10 (1992).

Wells, et al., "Human dystrophin expression corrects the myopathic phenotype in transgenic Mdx mice," Human Molecular Genetics 1(1):35–40 (1992).

Westphal, "Mouse models of human diseases," Curr Opin Biotechnol. 2(6):830–3 (1991).

Zhang, et al., "Increased susceptibility to ischemic brain damage in transgenic mice overexpressing the amyloid precursor protein," Journal of Neuroscience 17(20):7655–61 (1997).

* cited by examiner

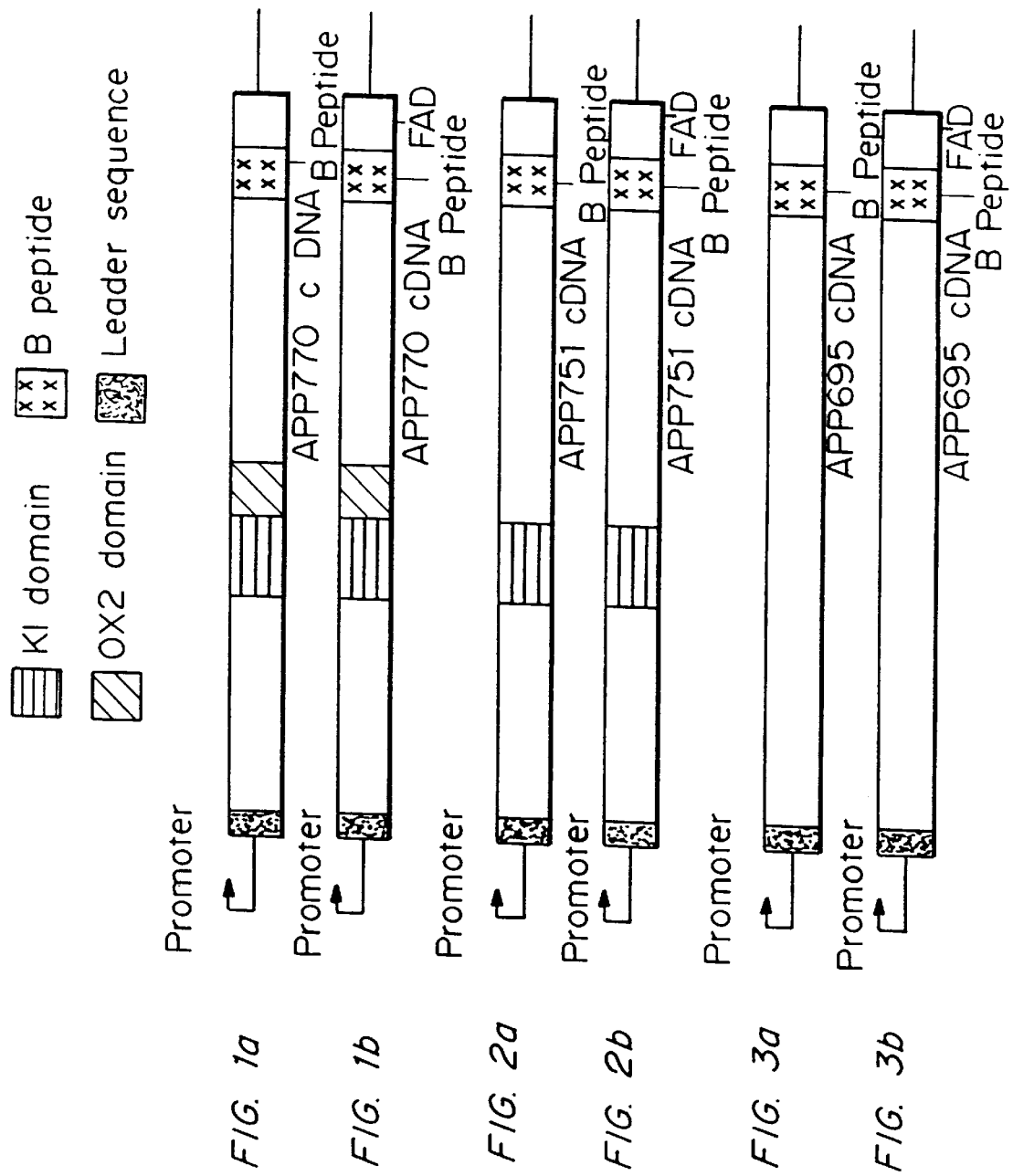

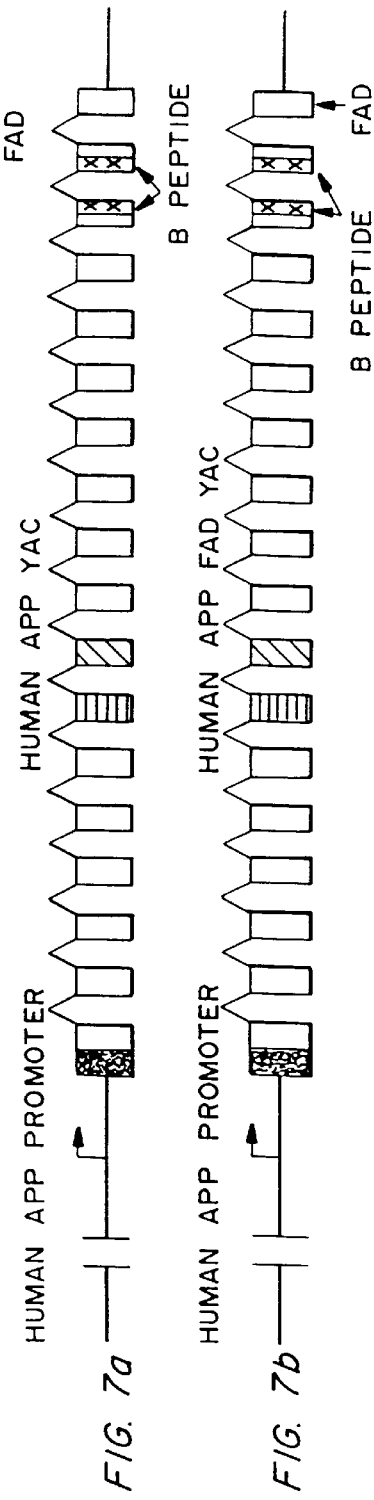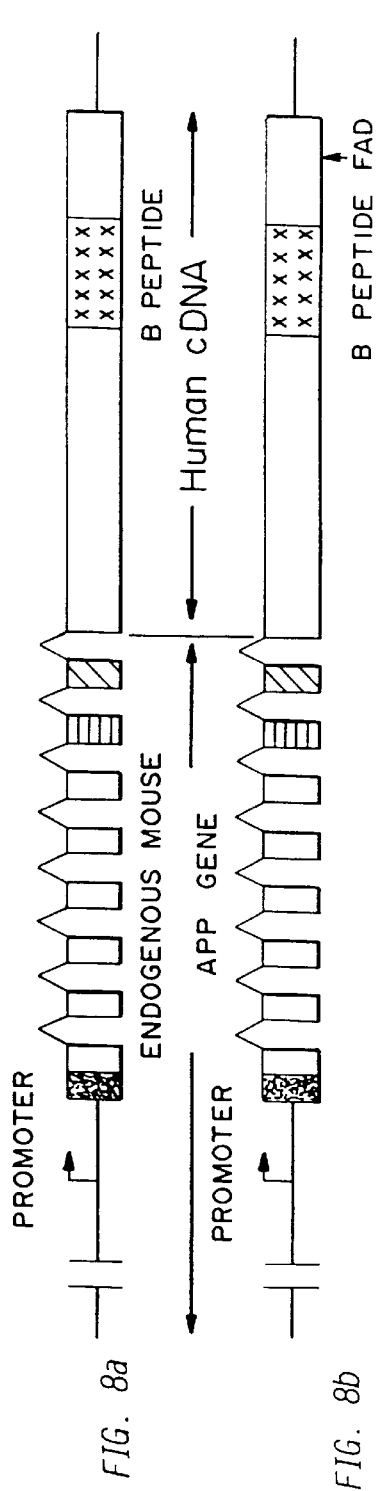
FIG. 6a
FIG. 6b
FIG. 7a
FIG. 7b
FIG. 8a
FIG. 8b

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 2085 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1-2085
        (D) OTHER INFORMATION: /function= "coding region for APP695."

(xi) SEQUENCE DESCRIPTION: SEQ ID NO:1:

```
ATG CTG CCC GGT TTG GCA CTG CTC CTG CTG GCC GCC TGG ACG GCT CGG        48
Met Leu Pro Gly Leu Ala Leu Leu Leu Leu Ala Ala Trp Thr Ala Arg
 1               5                  10                  15

GCG CTG GAG GTA CCC ACT GAT GGT AAT GCT GGC CTG CTG GCT GAA CCC        96
Ala Leu Glu Val Pro Thr Asp Gly Asn Ala Gly Leu Leu Ala Glu Pro
                20                  25                  30

CAG ATT GCC ATG TTC TGT GGC AGA CTG AAC ATG CAC ATG AAT GTC CAG       144
Gln Ile Ala Met Phe Cys Gly Arg Leu Asn Met His Met Asn Val Gln
            35                  40                  45

AAT GGG AAG TGG GAT TCA GAT CCA TCA GGG ACC AAA ACC TGC ATT GAT       192
Asn Gly Lys Trp Asp Ser Asp Pro Ser Gly Thr Lys Thr Cys Ile Asp
        50                  55                  60

ACC AAG GAA GGC ATC CTG CAG TAT TGC CAA GAA GTC TAC CCT GAA CTG       240
Thr Lys Glu Gly Ile Leu Gln Tyr Cys Gln Glu Val Tyr Pro Glu Leu
 65                  70                  75                  80

CAG ATC ACC AAT GTG GTA GAA GCC AAC CAA CCA GTG ACC ATC CAG AAC       288
Gln Ile Thr Asn Val Val Glu Ala Asn Gln Pro Val Thr Ile Gln Asn
                85                  90                  95
```

```
TGG TGC AAG CGG GGC CGC AAG CAG TGC AAG ACC CAT CCC CAC TTT GTG        336
Trp Cys Lys Arg Gly Arg Lys Gln Cys Lys Thr His Pro His Phe Val
            100                 105                 110

ATT CCC TAC CGC TGC TTA GTT GGT GAG TTT GTA AGT GAT GCC CTT CTC        384
Ile Pro Tyr Arg Cys Leu Val Gly Glu Phe Val Ser Asp Ala Leu Leu
            115                 120                 125

GTT CCT GAC AAG TGC AAA TTC TTA CAC CAG GAG AGG ATG GAT GTT TGC        432
Val Pro Asp Lys Cys Lys Phe Leu His Gln Glu Arg Met Asp Val Cys
130                 135                 140

GAA ACT CAT CTT CAC TGG CAC ACC GTC GCC AAA GAG ACA TGC AGT GAG        480
Glu Thr His Leu His Trp His Thr Val Ala Lys Glu Thr Cys Ser Glu
145                 150                 155                 160

AAG AGT ACC AAC TTG CAT GAC TAC GGC ATG TTG CTG CCC TGC GGA ATT        528
Lys Ser Thr Asn Leu His Asp Tyr Gly Met Leu Leu Pro Cys Gly Ile
                165                 170                 175

GAC AAG TTC CGA GGG GTA GAG TTT GTG TGT TGC CCA CTG GCT GAA GAA        576
Asp Lys Phe Arg Gly Val Glu Phe Val Cys Cys Pro Leu Ala Glu Glu
            180                 185                 190

AGT GAC AAT GTG GAT TCT GCT GAT GCG GAG GAG GAT GAC TCG GAT GTC        624
Ser Asp Asn Val Asp Ser Ala Asp Ala Glu Glu Asp Asp Ser Asp Val
            195                 200                 205

TGG TGG GGC GGA GCA GAC ACA GAC TAT GCA GAT GGG AGT GAA GAC AAA        672
Trp Trp Gly Gly Ala Asp Thr Asp Tyr Ala Asp Gly Ser Glu Asp Lys
210                 215                 220

GTA GTA GAA GTA GCA GAG GAG GAA GAA GTG GCT GAG GTG GAA GAA GAA        720
Val Val Glu Val Ala Glu Glu Glu Glu Val Ala Glu Val Glu Glu Glu
225                 230                 235                 240

GAA GCC GAT GAT GAC GAG GAC GAT GAG GAT GGT GAT GAG GTA GAG GAA        768
Glu Ala Asp Asp Asp Glu Asp Asp Glu Asp Gly Asp Glu Val Glu Glu
                245                 250                 255

GAG GCT GAG GAA CCC TAC GAA GAA GCC ACA GAG AGA ACC ACC AGC ATT        816
Glu Ala Glu Glu Pro Tyr Glu Glu Ala Thr Glu Arg Thr Thr Ser Ile
            260                 265                 270

GCC ACC ACC ACC ACC ACC ACA GAG TCT GTG GAA GAG GTG GTT CGA            864
Ala Thr Thr Thr Thr Thr Thr Glu Ser Val Glu Glu Val Val Arg
            275                 280                 285

GTT CCT ACA ACA GCA GCC AGT ACC CCT GAT GCC GTT GAC AAG TAT CTC        912
Val Pro Thr Thr Ala Ala Ser Thr Pro Asp Ala Val Asp Lys Tyr Leu
            290                 295                 300

GAG ACA CCT GGG GAT GAG AAT GAA CAT GCC CAT TTC CAG AAA GCC AAA        960
Glu Thr Pro Gly Asp Glu Asn Glu His Ala His Phe Gln Lys Ala Lys
305                 310                 315                 320

GAG AGG CTT GAG GCC AAG CAC CGA GAG AGA ATG TCC CAG GTC ATG AGA       1008
Glu Arg Leu Glu Ala Lys His Arg Glu Arg Met Ser Gln Val Met Arg
            325                 330                 335

GAA TGG GAA GAG GCA GAA CGT CAA GCA AAG AAC TTG CCT AAA GCT GAT       1056
Glu Trp Glu Glu Ala Glu Arg Gln Ala Lys Asn Leu Pro Lys Ala Asp
            340                 345                 350

AAG AAG GCA GTT ATC CAG CAT TTC CAG GAG AAA GTG GAA TCT TTG GAA       1104
Lys Lys Ala Val Ile Gln His Phe Gln Glu Lys Val Glu Ser Leu Glu
            355                 360                 365

CAG GAA GCA GCC AAC GAG AGA CAG CAG CTG GTG GAG ACA CAC ATG GCC       1152
Gln Glu Ala Ala Asn Glu Arg Gln Gln Leu Val Glu Thr His Met Ala
370                 375                 380

AGA GTG GAA GCC ATG CTC AAT GAC CGC CGC CGC CTG GCC CTG GAG AAC       1200
Arg Val Glu Ala Met Leu Asn Asp Arg Arg Arg Leu Ala Leu Glu Asn
385                 390                 395                 400

TAC ATC ACC GCT CTG CAG GCT GTT CCT CCT CGG CCT CGT CAC GTG TTC       1248
Tyr Ile Thr Ala Leu Gln Ala Val Pro Pro Arg Pro Arg His Val Phe
                405                 410                 415
```

```
AAT ATG CTA AAG AAG TAT GTC CGC GCA GAA CAG AAG GAC AGA CAG CAC         1296
Asn Met Leu Lys Lys Tyr Val Arg Ala Glu Gln Lys Asp Arg Gln His
            420                 425                 430

ACC CTA AAG CAT TTC GAG CAT GTG CGC ATG GTG GAT CCC AAG AAA GCC         1344
Thr Leu Lys His Phe Glu His Val Arg Met Val Asp Pro Lys Lys Ala
                435                 440                 445

GCT CAG ATC CGG TCC CAG GTT ATG ACA CAC CTC CGT GTG ATT TAT GAG         1392
Ala Gln Ile Arg Ser Gln Val Met Thr His Leu Arg Val Ile Tyr Glu
        450                 455                 460

CGC ATG AAT CAG TCT CTC TCC CTG CTC TAC AAC GTG CCT GCA GTG GCC         1440
Arg Met Asn Gln Ser Leu Ser Leu Leu Tyr Asn Val Pro Ala Val Ala
465                 470                 475                 480

GAG GAG ATT CAG GAT GAA GTT GAT GAG CTG CTT CAG AAA GAG CAA AAC         1488
Glu Glu Ile Gln Asp Glu Val Asp Glu Leu Leu Gln Lys Glu Gln Asn
                485                 490                 495

TAT TCA GAT GAC GTC TTG GCC AAC ATG ATT AGT GAA CCA AGG ATC AGT         1536
Tyr Ser Asp Asp Val Leu Ala Asn Met Ile Ser Glu Pro Arg Ile Ser
            500                 505                 510

TAC GGA AAC GAT GCT CTC ATG CCA TCT TTG ACC GAA ACG AAA ACC ACC         1584
Tyr Gly Asn Asp Ala Leu Met Pro Ser Leu Thr Glu Thr Lys Thr Thr
        515                 520                 525

GTG GAG CTC CTT CCC AGC CTG GAC GAT CTC CAG CCG TGG CAT TCT TTT         1632
Val Glu Leu Leu Pro Val Asn Gly Glu Phe Ser Leu Asp Asp Leu Gln
    530                 535                 540

GTG AAT GGA GAG TTC GGG GCT GAC TCT GTG CCA GCC AAC ACA GAA AAC         1680
Pro Trp His Ser Phe Gly Ala Asp Ser Val Pro Ala Asn Thr Glu Asn
545                 550                 555                 560

GAA GTT GAG CCT GTT GAT GCC CGC CCT GCT GCC GAC CGA GGA CTG ACC         1728
Glu Val Glu Pro Val Asp Ala Arg Pro Ala Ala Asp Arg Gly Leu Thr
                565                 570                 575

ACT CGA CCA GGT TCT GGG TTG ACA AAT ATC AAG ACG GAG GAG ATC TCT         1776
Thr Arg Pro Gly Ser Gly Leu Thr Asn Ile Lys Thr Glu Glu Ile Ser
            580                 585                 590

GAA GTG AAG ATG GAT GCA GAA TTC CGA CAT GAC TCA GGA TAT GAA GTT         1824
Glu Val Lys Met Asp Ala Glu Phe Arg His Asp Ser Gly Tyr Glu Val
        595                 600                 605

CAT CAT CAA AAA TTG GTG TTC TTT GCA GAA GAT GTG GGT TCA AAC AAA         1872
His His Gln Lys Leu Val Phe Phe Ala Glu Asp Val Gly Ser Asn Lys
    610                 615                 620

GGT GCA ATC ATT GGA CTC ATG GTG GGC GGT GTT GTC ATA GCG ACA GTG         1920
Gly Ala Ile Ile Gly Leu Met Val Gly Gly Val Val Ile Ala Thr Val
625                 630                 635                 640

ATC GTC ATC ACC TTG GTG ATG CTG AAG AAG AAA CAG TAC ACA TCC ATT         1968
Ile Val Ile Thr Leu Val Met Leu Lys Lys Lys Gln Tyr Thr Ser Ile
                645                 650                 655

CAT CAT GGT GTG GTG GAG GTT GAC GCC GCT GTC ACC CCA GAG GAG CGC         2016
His His Gly Val Val Glu Val Asp Ala Ala Val Thr Pro Glu Glu Arg
            660                 665                 670

CAC CTG TCC AAG ATG CAG CAG AAC GGC TAC GAA AAT CCA ACC TAC AAG         2064
His Leu Ser Lys Met Gln Gln Asn Gly Tyr Glu Asn Pro Thr Tyr Lys
        675                 680                 685

TTC TTT GAG CAG ATG CAG AAC                                             2085
Phe Phe Glu Gln Met Gln Asn
    690                 695

(2) INFORMATION FOR SEQ ID NO:2:

(i) SEQUENCE CHARACTERISTICS:
        (A) LENGTH: 695 amino acids
        (B) TYPE: amino acid
```

(D) TOPOLOGY: linear (ii) MOLECULE TYPE: protein (xi) SEQUENCE DESCRIPTION: SEQ ID NO:2:

```
Met Leu Pro Gly Leu Ala Leu Leu Leu Ala Ala Trp Thr Ala Arg
  1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
             85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
            290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
            325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
            370                 375                 380

Arg Val Glu Ala Met Leu Asn Asp Arg Arg Arg Leu Ala Leu Glu Asn
```

-continued

```
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
                435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
                515                 520                 525

Val Glu Leu Leu Pro Val Asn Gly Glu Phe Ser Leu Asp Asp Leu Gln
                530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Lys Met Asp Ala Glu Phe Arg His Asp Ser Gly Tyr Glu Val
                595                 600                 605

His His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
                660                 665                 670

His Leu Ser Lys Met Gln Gln Asn Gly Tyr Glu Asn Pro Thr Tyr Lys
                675                 680                 685

Phe Phe Glu Gln Met Gln Asn
                690                 695

(2) INFORMATION FOR SEQ ID NO:3:

(i) SEQUENCE CHARACTERISTICS:
        (A) LENGTH: 2253 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1-2253
        (D) OTHER INFORMATION: /function= "coding region for APP751."
```

(xi) SEQUENCE DESCRIPTION: SEQ ID NO:3:

```
ATG CTG CCC GGT TTG GCA CTG CTC CTG CTG GCC GCC TGG ACG GCT CGG         48
Met Leu Pro Gly Leu Ala Leu Leu Leu Leu Ala Ala Trp Thr Ala Arg
 1               5                  10                  15

GCG CTG GAG GTA CCC ACT GAT GGT AAT GCT GGC CTG CTG GCT GAA CCC         96
Ala Leu Glu Val Pro Thr Asp Gly Asn Ala Gly Leu Leu Ala Glu Pro
                 20                  25                  30

CAG ATT GCC ATG TTC TGT GGC AGA CTG AAC ATG CAC ATG AAT GTC CAG        144
Gln Ile Ala Met Phe Cys Gly Arg Leu Asn Met His Met Asn Val Gln
             35                  40                  45

AAT GGG AAG TGG GAT TCA GAT CCA TCA GGG ACC AAA ACC TGC ATT GAT        192
Asn Gly Lys Trp Asp Ser Asp Pro Ser Gly Thr Lys Thr Cys Ile Asp
         50                  55                  60

ACC AAG GAA GGC ATC CTG CAG TAT TGC CAA GAA GTC TAC CCT GAA CTG        240
Thr Lys Glu Gly Ile Leu Gln Tyr Cys Gln Glu Val Tyr Pro Glu Leu
 65                  70                  75                  80

CAG ATC ACC AAT GTG GTA GAA GCC AAC CAA CCA GTG ACC ATC CAG AAC        288
Gln Ile Thr Asn Val Val Glu Ala Asn Gln Pro Val Thr Ile Gln Asn
                 85                  90                  95

TGG TGC AAG CGG GGC CGC AAG CAG TGC AAG ACC CAT CCC CAC TTT GTG        336
Trp Cys Lys Arg Gly Arg Lys Gln Cys Lys Thr His Pro His Phe Val
            100                 105                 110

ATT CCC TAC CGC TGC TTA GTT GGT GAG TTT GTA AGT GAT GCC CTT CTC        384
Ile Pro Tyr Arg Cys Leu Val Gly Glu Phe Val Ser Asp Ala Leu Leu
            115                 120                 125

GTT CCT GAC AAG TGC AAA TTC TTA CAC CAG GAG AGG ATG GAT GTT TGC        432
Val Pro Asp Lys Cys Lys Phe Leu His Gln Glu Arg Met Asp Val Cys
130                 135                 140

GAA ACT CAT CTT CAC TGG CAC ACC GTC GCC AAA GAG ACA TGC AGT GAG        480
Glu Thr His Leu His Trp His Thr Val Ala Lys Glu Thr Cys Ser Glu
145                 150                 155                 160

AAG AGT ACC AAC TTG CAT GAC TAC GGC ATG TTG CTG CCC TGC GGA ATT        528
Lys Ser Thr Asn Leu His Asp Tyr Gly Met Leu Leu Pro Cys Gly Ile
                165                 170                 175

GAC AAG TTC CGA GGG GTA GAG TTT GTG TGT TGC CCA CTG GCT GAA GAA        576
Asp Lys Phe Arg Gly Val Glu Phe Val Cys Cys Pro Leu Ala Glu Glu
            180                 185                 190

AGT GAC AAT GTG GAT TCT GCT GAT GCG GAG GAG GAT GAC TCG GAT GTC        624
Ser Asp Asn Val Asp Ser Ala Asp Ala Glu Glu Asp Asp Ser Asp Val
            195                 200                 205

TGG TGG GGC GGA GCA GAC ACA GAC TAT GCA GAT GGG AGT GAA GAC AAA        672
Trp Trp Gly Gly Ala Asp Thr Asp Tyr Ala Asp Gly Ser Glu Asp Lys
210                 215                 220

GTA GTA GAA GTA GCA GAG GAG GAA GTG GCT GAG GTG GAA GAA GAA            720
Val Val Glu Val Ala Glu Glu Glu Val Ala Glu Val Glu Glu Glu
225                 230                 235                 240

GAA GCC GAT GAT GAC GAG GAC GAT GAG GAT GGT GAT GAG GTA GAG GAA        768
Glu Ala Asp Asp Asp Glu Asp Asp Glu Asp Gly Asp Glu Val Glu Glu
                245                 250                 255

GAG GCT GAG GAA CCC TAC GAA GAA GCC ACA GAG AGA ACC ACC AGC ATT        816
Glu Ala Glu Glu Pro Tyr Glu Glu Ala Thr Glu Arg Thr Thr Ser Ile
                260                 265                 270

GCC ACC ACC ACC ACC ACC ACA GAG TCT GTG GAA GAG GTG GTT CGA            864
Ala Thr Thr Thr Thr Thr Thr Glu Ser Val Glu Glu Val Val Arg
            275                 280                 285

GAG GTG TGC TCT GAA CAA GCC GAG ACG GGG CCG TGC CGA GCA ATG ATC        912
Glu Val Cys Ser Glu Gln Ala Glu Thr Gly Pro Cys Arg Ala Met Ile
            290                 295                 300

TCC CGC TGG TAC TTT GAT GTG ACT GAA GGG AAG TGT GCC CCA TTC TTT        960
```

-continued

```
Ser Arg Trp Tyr Phe Asp Val Thr Glu Gly Lys Cys Ala Pro Phe Phe
305                 310                 315                 320

TAC GGC GGA TGT GGC GGC AAC CGG AAC AAC TTT GAC ACA GAA GAG TAC       1008
Tyr Gly Gly Cys Gly Gly Asn Arg Asn Asn Phe Asp Thr Glu Glu Tyr
                325                 330                 335

TGC ATG GCC GTG TGT GGC AGC GCC ATT CCT ACA ACA GCA GCC AGT ACC       1056
Cys Met Ala Val Cys Gly Ser Ala Ile Pro Thr Thr Ala Ala Ser Thr
            340                 345                 350

CCT GAT GCC GTT GAC AAG TAT CTC GAG ACA CCT GGG GAT GAG AAT GAA       1104
Pro Asp Ala Val Asp Lys Tyr Leu Glu Thr Pro Gly Asp Glu Asn Glu
        355                 360                 365

CAT GCC CAT TTC CAG AAA GCC AAA GAG AGG CTT GAG GCC AAG CAC CGA       1152
His Ala His Phe Gln Lys Ala Lys Glu Arg Leu Glu Ala Lys His Arg
    370                 375                 380

GAG AGA ATG TCC CAG GTC ATG AGA GAA TGG GAA GAG GCA GAA CGT CAA       1200
Glu Arg Met Ser Gln Val Met Arg Glu Trp Glu Glu Ala Glu Arg Gln
385                 390                 395                 400

GCA AAG AAC TTG CCT AAA GCT GAT AAG AAG GCA GTT ATC CAG CAT TTC       1248
Ala Lys Asn Leu Pro Lys Ala Asp Lys Lys Ala Val Ile Gln His Phe
                405                 410                 415

CAG GAG AAA GTG GAA TCT TTG GAA CAG GAA GCA GCC AAC GAG AGA CAG       1296
Gln Glu Lys Val Glu Ser Leu Glu Gln Glu Ala Ala Asn Glu Arg Gln
            420                 425                 430

CAG CTG GTG GAG ACA CAC ATG GCC AGA GTG GAA GCC ATG CTC AAT GAC       1344
Gln Leu Val Glu Thr His Met Ala Arg Val Glu Ala Met Leu Asn Asp
        435                 440                 445

CGC CGC CGC CTG GCC CTG GAG AAC TAC ATC ACC GCT CTG CAG GCT GTT       1392
Arg Arg Arg Leu Ala Leu Glu Asn Tyr Ile Thr Ala Leu Gln Ala Val
    450                 455                 460

CCT CCT CGG CCT CGT CAC GTG TTC AAT ATG CTA AAG AAG TAT GTC CGC       1440
Pro Pro Arg Pro Arg His Val Phe Asn Met Leu Lys Lys Tyr Val Arg
465                 470                 475                 480

GCA GAA CAG AAG GAC AGA CAG CAC ACC CTA AAG CAT TTC GAG CAT GTG       1488
Ala Glu Gln Lys Asp Arg Gln His Thr Leu Lys His Phe Glu His Val
                485                 490                 495

CGC ATG GTG GAT CCC AAG AAA GCC GCT CAG ATC CGG TCC CAG GTT ATG       1536
Arg Met Val Asp Pro Lys Lys Ala Ala Gln Ile Arg Ser Gln Val Met
            500                 505                 510

ACA CAC CTC CGT GTG ATT TAT GAG CGC ATG AAT CAG TCT CTC TCC CTG       1584
Thr His Leu Arg Val Ile Tyr Glu Arg Met Asn Gln Ser Leu Ser Leu
        515                 520                 525

CTC TAC AAC GTG CCT GCA GTG GCC GAG GAG ATT CAG GAT GAA GTT GAT       1632
Leu Tyr Asn Val Pro Ala Val Ala Glu Glu Ile Gln Asp Glu Val Asp
    530                 535                 540

GAG CTG CTT CAG AAA GAG CAA AAC TAT TCA GAT GAC GTC TTG GCC AAC       1680
Glu Leu Leu Gln Lys Glu Gln Asn Tyr Ser Asp Asp Val Leu Ala Asn
545                 550                 555                 560

ATG ATT AGT GAA CCA AGG ATC AGT TAC GGA AAC GAT GCT CTC ATG CCA       1728
Met Ile Ser Glu Pro Arg Ile Ser Tyr Gly Asn Asp Ala Leu Met Pro
                565                 570                 575

TCT TTG ACC GAA ACG AAA ACC ACC GTG GAG CTC CTT CCC GTG AAT GGA       1776
Ser Leu Thr Glu Thr Lys Thr Thr Val Glu Leu Leu Pro Val Asn Gly
            580                 585                 590

GAG TTC AGC CTG GAC GAT CTC CAG CCG TGG CAT TCT TTT GGG GCT GAC       1824
Glu Phe Ser Leu Asp Asp Leu Gln Pro Trp His Ser Phe Gly Ala Asp
        595                 600                 605

TCT GTG CCA GCC AAC ACA GAA AAC GAA GTT GAG CCT GTT GAT GCC CGC       1872
Ser Val Pro Ala Asn Thr Glu Asn Glu Val Glu Pro Val Asp Ala Arg
    610                 615                 620
```

```
CCT GCT GCC GAC CGA GGA CTG ACC ACT CGA CCA GGT TCT GGG TTG ACA    1920
Pro Ala Ala Asp Arg Gly Leu Thr Thr Arg Pro Gly Ser Gly Leu Thr
625                 630                 635                 640

AAT ATC AAG ACG GAG GAG ATC TCT GAA GTG AAG ATG GAT GCA GAA TTC    1968
Asn Ile Lys Thr Glu Glu Ile Ser Glu Val Lys Met Asp Ala Glu Phe
                645                 650                 655

CGA CAT GAC TCA GGA TAT GAA GTT CAT CAT CAA AAA TTG GTG TTC TTT    2016
Arg His Asp Ser Gly Tyr Glu Val His His Gln Lys Leu Val Phe Phe
            660                 665                 670

GCA GAA GAT GTG GGT TCA AAC AAA GGT GCA ATC ATT GGA CTC ATG GTG    2064
Ala Glu Asp Val Gly Ser Asn Lys Gly Ala Ile Ile Gly Leu Met Val
        675                 680                 685

GGC GGT GTT GTC ATA GCG ACA GTG ATC GTC ATC ACC TTG GTG ATG CTG    2112
Gly Gly Val Val Ile Ala Thr Val Ile Val Ile Thr Leu Val Met Leu
690                 695                 700

AAG AAG AAA CAG TAC ACA TCC ATT CAT CAT GGT GTG GTG GAG GTT GAC    2160
Lys Lys Lys Gln Tyr Thr Ser Ile His His Gly Val Val Glu Val Asp
705                 710                 715                 720

GCC GCT GTC ACC CCA GAG GAG CGC CAC CTG TCC AAG ATG CAG CAG AAC    2208
Ala Ala Val Thr Pro Glu Glu Arg His Leu Ser Lys Met Gln Gln Asn
                725                 730                 735

GGC TAC GAA AAT CCA ACC TAC AAG TTC TTT GAG CAG ATG CAG AAC        2253
Gly Tyr Glu Asn Pro Thr Tyr Lys Phe Phe Glu Gln Met Gln Asn
            740                 745                 750
```

(2) INFORMATION FOR SEQ ID NO:4:

(i) SEQUENCE CHARACTERISTICS:
        (A) LENGTH: 751 amino acids
        (B) TYPE: amino acid
        (D) TOPOLOGY: linear (ii) MOLECULE TYPE: protein (xi) SEQUENCE DESCRIPTION: SEQ ID NO:4:

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190
```

-continued

```
Ser Asp Asn Val Asp Ser Ala Asp Ala Glu Glu Asp Asp Ser Asp Val
            195                 200                 205
Trp Trp Gly Gly Ala Asp Thr Asp Tyr Ala Asp Gly Ser Glu Asp Lys
    210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Gly Ala Thr Glu Arg Thr Thr Ser Ile
            260                 265                 270
Ala Thr Thr Thr Thr Thr Thr Glu Ser Val Glu Glu Val Val Arg
    275                 280                 285
Glu Val Cys Ser Glu Gln Ala Glu Thr Gly Pro Cys Arg Ala Met Ile
290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Ile Pro Thr Thr Ala Ala Ser Thr
                340                 345                 350
Pro Asp Ala Val Asp Lys Tyr Leu Glu Thr Pro Gly Asp Glu Asn Glu
            355                 360                 365
His Ala His Phe Gln Lys Ala Lys Glu Arg Leu Glu Ala Lys His Arg
    370                 375                 380
Glu Arg Met Ser Gln Val Met Arg Glu Trp Glu Glu Ala Glu Arg Gln
385                 390                 395                 400
Ala Lys Asn Leu Pro Lys Ala Asp Lys Lys Ala Val Ile Gln His Phe
                405                 410                 415
Gln Glu Lys Val Glu Ser Leu Glu Gln Glu Ala Ala Asn Glu Arg Gln
            420                 425                 430
Gln Leu Val Glu Thr His Met Ala Arg Val Glu Ala Met Leu Asn Asp
    435                 440                 445
Arg Arg Arg Leu Ala Leu Glu Asn Tyr Ile Thr Ala Leu Gln Ala Val
450                 455                 460
Pro Pro Arg Pro Arg His Val Phe Asn Met Leu Lys Lys Tyr Val Arg
465                 470                 475                 480
Ala Glu Gln Lys Asp Arg Gln His Thr Leu Lys His Phe Glu His Val
                485                 490                 495
Arg Met Val Asp Pro Lys Lys Ala Ala Gln Ile Arg Ser Gln Val Met
            500                 505                 510
Thr His Leu Arg Val Ile Tyr Glu Arg Met Asn Gln Ser Leu Ser Leu
    515                 520                 525
Leu Tyr Asn Val Pro Ala Val Ala Glu Glu Ile Gln Asp Glu Val Asp
530                 535                 540
Glu Leu Leu Gln Lys Glu Gln Asn Tyr Ser Asp Asp Val Leu Ala Asn
545                 550                 555                 560
Met Ile Ser Glu Pro Arg Ile Ser Tyr Gly Asn Asp Ala Leu Met Pro
                565                 570                 575
Ser Leu Thr Glu Thr Lys Thr Thr Val Glu Leu Leu Pro Val Asn Gly
            580                 585                 590
Glu Phe Ser Leu Asp Asp Leu Gln Pro Trp His Ser Phe Gly Ala Asp
    595                 600                 605
```

```
Ser Val Pro Ala Asn Thr Glu Asn Glu Val Glu Pro Val Asp Ala Arg
    610                 615                 620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
                645                 650                 655

Arg His Asp Ser Gly Tyr Glu Val His His Gln Lys Leu Val Phe Phe
                660                 665                 670

Ala Glu Asp Val Gly Ser Asn Lys Gly Ala Ile Ile Gly Leu Met Val
                675                 680                 685

Gly Gly Val Val Ile Ala Thr Val Ile Val Ile Thr Leu Val Met Leu
690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
                740                 745                 750
```

(2) INFORMATION FOR SEQ ID NO:5:

(i) SEQUENCE CHARACTERISTICS:
        (A) LENGTH: 2310 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1-2310
        (D) OTHER INFORMATION: /function= "coding region for APP770."

(xi) SEQUENCE DESCRIPTION: SEQ ID NO:5:

```
ATG CTG CCC GGT TTG GCA CTG CTC CTG CTG GCC GCC TGG ACG GCT CGG      48
Met Leu Pro Gly Leu Ala Leu Leu Leu Leu Ala Ala Trp Thr Ala Arg
1               5                   10                  15

GCG CTG GAG GTA CCC ACT GAT GGT AAT GCT GGC CTG CTG GCT GAA CCC      96
Ala Leu Glu Val Pro Thr Asp Gly Asn Ala Gly Leu Leu Ala Glu Pro
            20                  25                  30

CAG ATT GCC ATG TTC TGT GGC AGA CTG AAC ATG CAC ATG AAT GTC CAG     144
Gln Ile Ala Met Phe Cys Gly Arg Leu Asn Met His Met Asn Val Gln
        35                  40                  45

AAT GGG AAG TGG GAT TCA GAT CCA TCA GGG ACC AAA ACC TGC ATT GAT     192
Asn Gly Lys Trp Asp Ser Asp Pro Ser Gly Thr Lys Thr Cys Ile Asp
50                  55                  60

ACC AAG GAA GGC ATC CTG CAG TAT TGC CAA GAA GTC TAC CCT GAA CTG     240
Thr Lys Glu Gly Ile Leu Gln Tyr Cys Gln Glu Val Tyr Pro Glu Leu
65                  70                  75                  80

CAG ATC ACC AAT GTG GTA GAA GCC AAC CAA CCA GTG ACC ATC CAG AAC     288
Gln Ile Thr Asn Val Val Glu Ala Asn Gln Pro Val Thr Ile Gln Asn
                85                  90                  95

TGG TGC AAG CGG GGC CGC AAG CAG TGC AAG ACC CAT CCC CAC TTT GTG     336
Trp Cys Lys Arg Gly Arg Lys Gln Cys Lys Thr His Pro His Phe Val
            100                 105                 110

ATT CCC TAC CGC TGC TTA GTT GGT GAG TTT GTA AGT GAT GCC CTT CTC     384
Ile Pro Tyr Arg Cys Leu Val Gly Glu Phe Val Ser Asp Ala Leu Leu
```

```
              115                 120                     125
GTT CCT GAC AAG TGC AAA TTC TTA CAC CAG GAG AGG ATG GAT GTT TGC      432
Val Pro Asp Lys Cys Lys Phe Leu His Gln Glu Arg Met Asp Val Cys
        130                 135                 140

GAA ACT CAT CTT CAC TGG CAC ACC GTC GCC AAA GAG ACA TGC AGT GAG      480
Glu Thr His Leu His Trp His Thr Val Ala Lys Glu Thr Cys Ser Glu
145                 150                 155                 160

AAG AGT ACC AAC TTG CAT GAC TAC GGC ATG TTG CTG CCC TGC GGA ATT      528
Lys Ser Thr Asn Leu His Asp Tyr Gly Met Leu Leu Pro Cys Gly Ile
                165                 170                 175

GAC AAG TTC CGA GGG GTA GAG TTT GTG TGT TGC CCA CTG GCT GAA GAA      576
Asp Lys Phe Arg Gly Val Glu Phe Val Cys Cys Pro Leu Ala Glu Glu
            180                 185                 190

AGT GAC AAT GTG GAT TCT GCT GAT GCG GAG GAG GAT GAC TCG GAT GTC      624
Ser Asp Asn Val Asp Ser Ala Asp Ala Glu Glu Asp Asp Ser Asp Val
        195                 200                 205

TGG TGG GGC GGA GCA GAC ACA GAC TAT GCA GAT GGG AGT GAA GAC AAA      672
Trp Trp Gly Gly Ala Asp Thr Asp Tyr Ala Asp Gly Ser Glu Asp Lys
    210                 215                 220

GTA GTA GAA GTA GCA GAG GAG GAA GAA GTG GCT GAG GTG GAA GAA GAA      720
Val Val Glu Val Ala Glu Glu Glu Glu Val Ala Glu Val Glu Glu Glu
225                 230                 235                 240

GAA GCC GAT GAT GAC GAG GAC GAT GAG GAT GGT GAT GAG GTA GAG GAA      768
Glu Ala Asp Asp Asp Glu Asp Asp Glu Asp Gly Asp Glu Val Glu Glu
                245                 250                 255

GAG GCT GAG GAA CCC TAC GAA GAA GCC ACA GAG AGA ACC ACC AGC ATT      816
Glu Ala Glu Glu Pro Tyr Glu Glu Ala Thr Glu Arg Thr Thr Ser Ile
            260                 265                 270

GCC ACC ACC ACC ACC ACC ACA GAG TCT GTG GAA GAG GTG GTT CGA          864
Ala Thr Thr Thr Thr Thr Thr Glu Ser Val Glu Glu Val Val Arg
        275                 280                 285

GAG GTG TGC TCT GAA CAA GCC GAG ACG GGG CCG TGC CGA GCA ATG ATC      912
Glu Val Cys Ser Glu Gln Ala Glu Thr Gly Pro Cys Arg Ala Met Ile
    290                 295                 300

TCC CGC TGG TAC TTT GAT GTG ACT GAA GGG AAG TGT GCC CCA TTC TTT      960
Ser Arg Trp Tyr Phe Asp Val Thr Glu Gly Lys Cys Ala Pro Phe Phe
305                 310                 315                 320

TAC GGC GGA TGT GGC GGC AAC CGG AAC AAC TTT GAC ACA GAA GAG TAC     1008
Tyr Gly Gly Cys Gly Gly Asn Arg Asn Asn Phe Asp Thr Glu Glu Tyr
                325                 330                 335

TGC ATG GCC GTG TGT GGC AGC GCC ATG TCC CAA AGT TTA CTC AAG ACT     1056
Cys Met Ala Val Cys Gly Ser Ala Met Ser Gln Ser Leu Leu Lys Thr
            340                 345                 350

ACC CAG GAA CCT CTT GCC CGA GAT CCT GTT AAA CTT CCT ACA ACA GCA     1104
Thr Gln Glu Pro Leu Ala Arg Asp Pro Val Lys Leu Pro Thr Thr Ala
        355                 360                 365

GCC AGT ACC CCT GAT GCC GTT GAC AAG TAT CTC GAG ACA CCT GGG GAT     1152
Ala Ser Thr Pro Asp Ala Val Asp Lys Tyr Leu Glu Thr Pro Gly Asp
    370                 375                 380

GAG AAT GAA CAT GCC CAT TTC CAG AAA GCC AAA GAG AGG CTT GAG GCC     1200
Glu Asn Glu His Ala His Phe Gln Lys Ala Lys Glu Arg Leu Glu Ala
385                 390                 395                 400

AAG CAC CGA GAG AGA ATG TCC CAG GTC ATG AGA GAA TGG GAA GAG GCA     1248
Lys His Arg Glu Arg Met Ser Gln Val Met Arg Glu Trp Glu Glu Ala
                405                 410                 415

GAA CGT CAA GCA AAG AAC TTG CCT AAA GCT GAT AAG AAG GCA GTT ATC     1296
Glu Arg Gln Ala Lys Asn Leu Pro Lys Ala Asp Lys Lys Ala Val Ile
            420                 425                 430

CAG CAT TTC CAG GAG AAA GTG GAA TCT TTG GAA CAG GAA GCA GCC AAC     1344
Gln His Phe Gln Glu Lys Val Glu Ser Leu Glu Gln Glu Ala Ala Asn
```

-continued

| | | | | | | | | | | | | | |
|---|---|---|---|---|---|---|---|---|---|---|---|---|---|
| Gln | His | Phe | Gln | Glu | Lys | Val | Glu | Ser | Leu | Glu | Gln | Glu | Ala | Ala | Asn |
| | | | 435 | | | | 440 | | | | 445 | | |

```
GAG AGA CAG CAG CTG GTG GAG ACA CAC ATG GCC AGA GTG GAA GCC ATG      1392
Glu Arg Gln Gln Leu Val Glu Thr His Met Ala Arg Val Glu Ala Met
450                 455                 460

CTC AAT GAC CGC CGC CGC CTG GCC CTG GAG AAC TAC ATC ACC GCT CTG      1440
Leu Asn Asp Arg Arg Arg Leu Ala Leu Glu Asn Tyr Ile Thr Ala Leu
465                 470                 475                 480

CAG GCT GTT CCT CCT CGG CCT CGT CAC GTG TTC AAT ATG CTA AAG AAG      1488
Gln Ala Val Pro Pro Arg Pro Arg His Val Phe Asn Met Leu Lys Lys
                485                 490                 495

TAT GTC CGC GCA GAA CAG AAG GAC AGA CAG CAC ACC CTA AAG CAT TTC      1536
Tyr Val Arg Ala Glu Gln Lys Asp Arg Gln His Thr Leu Lys His Phe
        500                 505                 510

GAG CAT GTG CGC ATG GTG GAT CCC AAG AAA GCC GCT CAG ATC CGG TCC      1584
Glu His Val Arg Met Val Asp Pro Lys Lys Ala Ala Gln Ile Arg Ser
    515                 520                 525

CAG GTT ATG ACA CAC CTC CGT GTG ATT TAT GAG CGC ATG AAT CAG TCT      1632
Gln Val Met Thr His Leu Arg Val Ile Tyr Glu Arg Met Asn Gln Ser
530                 535                 540

CTC TCC CTG CTC TAC AAC GTG CCT GCA GTG GCC GAG GAG ATT CAG GAT      1680
Leu Ser Leu Leu Tyr Asn Val Pro Ala Val Ala Glu Glu Ile Gln Asp
545                 550                 555                 560

GAA GTT GAT GAG CTG CTT CAG AAA GAG CAA AAC TAT TCA GAT GAC GTC      1728
Glu Val Asp Glu Leu Leu Gln Lys Glu Gln Asn Tyr Ser Asp Asp Val
                565                 570                 575

TTG GCC AAC ATG ATT AGT GAA CCA AGG ATC AGT TAC GGA AAC GAT GCT      1776
Leu Ala Asn Met Ile Ser Glu Pro Arg Ile Ser Tyr Gly Asn Asp Ala
            580                 585                 590

CTC ATG CCA TCT TTG ACC GAA ACG AAA ACC ACC GTG GAG CTC CTT CCC      1824
Leu Met Pro Ser Leu Thr Glu Thr Lys Thr Thr Val Glu Leu Leu Pro
        595                 600                 605

GTG AAT GGA GAG TTC AGC CTG GAC GAT CTC CAG CCG TGG CAT TCT TTT      1872
Val Asn Gly Glu Phe Ser Leu Asp Asp Leu Gln Pro Trp His Ser Phe
    610                 615                 620

GGG GCT GAC TCT GTG CCA GCC AAC ACA GAA AAC GAA GTT GAG CCT GTT      1920
Gly Ala Asp Ser Val Pro Ala Asn Thr Glu Asn Glu Val Glu Pro Val
625                 630                 635                 640

GAT GCC CGC CCT GCT GCC GAC CGA GGA CTG ACC ACT CGA CCA GGT TCT      1968
Asp Ala Arg Pro Ala Ala Asp Arg Gly Leu Thr Thr Arg Pro Gly Ser
                645                 650                 655

GGG TTG ACA AAT ATC AAG ACG GAG GAG ATC TCT GAA GTG AAG ATG GAT      2016
Gly Leu Thr Asn Ile Lys Thr Glu Glu Ile Ser Glu Val Lys Met Asp
            660                 665                 670

GCA GAA TTC CGA CAT GAC TCA GGA TAT GAA GTT CAT CAT CAA AAA TTG      2064
Ala Glu Phe Arg His Asp Ser Gly Tyr Glu Val His His Gln Lys Leu
        675                 680                 685

GTG TTC TTT GCA GAA GAT GTG GGT TCA AAC AAA GGT GCA ATC ATT GGA      2112
Val Phe Phe Ala Glu Asp Val Gly Ser Asn Lys Gly Ala Ile Ile Gly
    690                 695                 700

CTC ATG GTG GGC GGT GTT GTC ATA GCG ACA GTG ATC GTC ATC ACC TTG      2160
Leu Met Val Gly Gly Val Val Ile Ala Thr Val Ile Val Ile Thr Leu
705                 710                 715                 720

GTG ATG CTG AAG AAG AAA CAG TAC ACA TCC ATT CAT CAT GGT GTG GTG      2208
Val Met Leu Lys Lys Lys Gln Tyr Thr Ser Ile His His Gly Val Val
                725                 730                 735

GAG GTT GAC GCC GCT GTC ACC CCA GAG GAG CGC CAC CTG TCC AAG ATG      2256
Glu Val Asp Ala Ala Val Thr Pro Glu Glu Arg His Leu Ser Lys Met
            740                 745                 750
```

```
CAG CAG AAC GGC TAC GAA AAT CCA ACC TAC AAG TTC TTT GAG CAG ATG    2304
Gln Gln Asn Gly Tyr Glu Asn Pro Thr Tyr Lys Phe Phe Glu Gln Met
        755                 760                 765

CAG AAC                                                            2310
Gln Asn
    770
```

(2) INFORMATION FOR SEQ ID NO:6:

(i) SEQUENCE CHARACTERISTICS:
        (A) LENGTH: 770 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320
```

-continued

```
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
                340                 345                 350
Thr Gln Glu Pro Leu Ala Arg Asp Pro Val Lys Leu Pro Thr Thr Ala
                355                 360                 365
Ala Ser Thr Pro Asp Ala Val Asp Lys Tyr Leu Glu Thr Pro Gly Asp
                370                 375             380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Ala
                405                 410                 415
Glu Arg Gln Ala Lys Asn Leu Pro Lys Ala Asp Lys Lys Ala Val Ile
                420                 425                 430
Gln His Phe Gln Glu Lys Val Glu Ser Leu Glu Gln Glu Ala Ala Asn
                435                 440                 445
Glu Arg Gln Gln Leu Val Glu Thr His Met Ala Arg Val Glu Ala Met
                450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
                500                 505                 510
Glu His Val Arg Met Val Asp Pro Lys Lys Ala Ala Gln Ile Arg Ser
                515                 520                 525
Gln Val Met Thr His Leu Arg Val Ile Tyr Glu Arg Met Asn Gln Ser
                530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
                580                 585                 590
Leu Met Pro Ser Leu Thr Glu Thr Lys Thr Thr Val Glu Leu Leu Pro
                595                 600                 605
Val Asn Gly Glu Phe Ser Leu Asp Asp Leu Gln Pro Trp His Ser Phe
                610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
                660                 665                 670
Ala Glu Phe Arg His Asp Ser Gly Tyr Glu Val His His Gln Lys Leu
                675                 680                 685
Val Phe Phe Ala Glu Asp Val Gly Ser Asn Lys Gly Ala Ile Ile Gly
                690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
```

```
Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:7:

CCGATGATGA CGAGGACGAT                                              20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:8:

TGAACACGTG ACGAGGCCGA                                              20

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:9:

```
Phe Arg Val Gly Ser
             5
```

(2) INFORMATION FOR SEQ ID NO:10:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:10:

```
Asp Ala Glu Phe Arg Gly Gly Cys
             5
```

METHOD FOR SELECTING A TRANSGENIC MOUSE MODEL OF ALZHEIMER'S DISEASE

This application is a continuation-in-part of U.S. application Ser. No. 08/660,487, filed Jun. 7, 1996, which is a continuation-in-part of U.S. application Ser. No. 08/480, 653, filed Jun. 7, 1995. This application is also a continuation-in-part of U.S. application Ser. No. 08/659, 797, filed Jun. 7, 1996, which is a continuation-in-part of U.S. application Ser. No. 08/486,538, filed Jun. 7, 1995. This application is also a continuation-in-part of U.S. application Ser. No. 08/486,538, filed Jun. 7, 1995.

BACKGROUND OF THE INVENTION

Transgenic animal models of Alzheimer's disease are described along with a method of using the transgenic animal models to screen for therapeutics useful for the treatment of Alzheimer's disease.

Alzheimer's disease (AD) is a degenerative disorder of the brain first described by Alios Alzheimer in 1907 after examining one of his patients who suffered drastic reduction in cognitive abilities and had generalized dementia (*The early story of Alzheimer's Disease,* edited by Bick et al. (Raven Press, New York 1987)). It is the leading cause of dementia in elderly persons. AD patients have increased problems with memory loss and intellectual functions which progress to the point where they cannot function as normal individuals. With the loss of intellectual skills the patients exhibit personality changes, socially inappropriate actions and schizophrenia (*A Guide to the Understanding of Alzheimer's Disease and Related Disorders,* edited by Jorm (New York University Press, New York 1987). AD is devastating for both victims and their families, for there is no effective palliative or preventive treatment for the inevitable neurodegeneration.

The impact of AD on society and on the national economy is enormous. It is expected that the demented elderly population in the United States will increase by 41% by the year 2000. It is expensive for the health care systems that must provide institutional and ancillary care for the AD patients at an estimated annual cost of $40 billion (Jorm (1987); Fisher, "Alzheimer's Disease", New York Times, Aug. 23, 1989, page D1, edited by Reisberg (The Free Press, New York & London 1983)). These factors imply action must be taken to generate effective treatments for AD.

At a macroscopic level, the brains of AD patients are usually smaller, sometimes weighing less than 1,000 grams. At a microscopic level, the histopathological hallmarks of AD include neurofibrillary tangles (NFT), neuritic plaques, and degeneration of neurons. AD patients exhibit degeneration of nerve cells in the frontal and temporal cortex of the cerebral cortex, pyramidal neurons of hippocampus, neurons in the medial, medial central, and cortical nuclei of the amygdala, noradrenergic neurons in the locus coeruleus, and the neurons in the basal forebrain cholinergic system. Loss of neurons in the cholinergic system leads to a consistent deficit in cholinergic presynaptic markers in AD (Fisher (1983); *Alzheimer's Disease and Related Disorders, Research and Development* edited by Kelly (Charles C. Thomas, Springfield, Ill. 1984)). In fact, AD is defined by the neuropathology of the brain.

AD is associated with neuritic plaques measuring up to 200 μm in diameter in the cortex, hippocampus, subiculum, hippocampal gyrus, and amygdala. One of the principal constituents of neuritic plaques is amyloid, which is stained by Congo Red (Fisher (1983); Kelly (1984)). Amyloid plaques stained by Congo Red are extracellular, pink or rust-colored in bright field, and birefringent in polarized light. The plaques are composed of polypeptide fibrils and are often present around blood vessels, reducing blood supply to various neurons in the brain.

Various factors such as genetic predisposition, infectious agents, toxins, metals, and head trauma have all been suggested as possible mechanisms of AD neuropathy. However, available evidence strongly indicates that there are distinct types of genetic predispositions for AD. First, molecular analysis has provided evidence for mutations in the amyloid precursor protein (APP) gene in certain AD-stricken families (Goate et al. *Nature* 349:704–706 (1991); Murrell et al. *Science* 254:97–99 (1991); Chartier-Harlin et al. *Nature* 353:844–846 (1991); Mullan et al., *Nature Genet.* 1:345–347 (1992)). Additional genes for dominant forms of early onset AD reside on chromosome 14 and chromosome 1 (Rogaev et al., *Nature* 376:775–778 (1995); Levy-Lahad et al., *Science* 269:973–977 (1995); Sherrington et al., *Nature* 375:754–760 (1995)). Another loci associated with AD resides on chromosome 19 and encodes a variant form of apolipoprotein E (Corder, *Science* 261:921–923 (1993).

Amyloid plaques are abundantly present in AD patients and in Down's Syndrome individuals surviving to the age of 40. The overexpression of APP in Down's Syndrome is recognized as a possible cause of the development of AD in Down's patients over thirty years of age (Rumble et al., *New England J. Med.* 320:1446–1452 (1989); Mann et al., *Neurobiol. Aging* 10:397–399 (1989)). The plaques are also present in the normal aging brain, although at a lower number. These plaques are made up primarily of the amyloid β peptide (Aβ; sometimes also referred to in the literature as β-amyloid peptide or β peptide) (Glenner and Wong, *Biochem. Biophys. Res. Comm.* 120:885–890 (1984)), which is also the primary protein constituent in cerebrovascular amyloid deposits. The amyloid is a filamentous material that is arranged in beta-pleated sheets. Aβ is a hydrophobic peptide comprising up to 43 amino acids. The determination of its amino acid sequence led to the cloning of the APP cDNA (Kang et al., *Nature* 325:733–735 (1987); Goldgaber et al., *Science* 235:877–880 (1987); Robakis et al., *Proc. Natl. Acad. Sci.* 84:4190–4194 (1987); Tanzi et al., *Nature* 331:528–530 (1988)) and genomic APP DNA (Lemaire et al., *Nucl. Acids Res.* 17:517–522 (1989); Yoshikai et al., *Gene* 87, 257–263 (1990)). A number of forms of APP cDNA have been identified, including the three most abundant forms, APP695, APP751, and APP770. These forms arise from a single precursor RNA by alternate splicing. The gene spans more than 175 kb with 18 exons (Yoshikai et al. (1990)). APP contains an extracellular domain, a transmembrane region and a cytoplasmic domain. Aβ consists of up to 28 amino acids just outside the hydrophobic transmembrane domain and up to 15 residues of this transmembrane domain. Thus, Aβ is a cleavage product derived from APP which is normally found in brain and other tissues such as heart, kidney and spleen. However, Aβ deposits are usually found in abundance only in the brain.

The larger alternate forms of APP (APP751, APP770) consist of APP695 plus one or two additional domains. APP751 consists of all 695 amino acids of APP695 plus an additional 56 amino acids which has homology to the Kunitz family of serine protease inhibitors (KPI) (Tanzi et al. (1988); Weidemann et al., *Cell* 57:115–126 (1989); Kitaguchi et al., *Nature* 331:530–532 (1988); Tanzi et al., *Nature* 329:156 (1987)). APP770 contains all 751 amino acids of APP751 and an additional 19 amino acid domain homologous to the neuron cell surface antigen OX-2 (Weidemann et al. (1989); Kitaguchi et al. (1988)). Unless otherwise noted, the amino acid positions referred to herein are the positions as they appear in APP770. The amino acid number of equivalent positions in APP695 and APP751 differ in some cases due to the absence of the OX-2 and KPI domains. By convention, the amino acid positions of all forms of APP are referenced by the equivalent positions in the APP770 form. Unless otherwise noted, this convention is followed herein. Unless otherwise noted, all forms of APP and fragments of APP, including all forms of Aβ, referred to herein are based on the human APP amino acid sequence. APP is post-translationally modified by the removal of the leader sequence and by the addition of sulfate and sugar groups.

Van Broeckhaven et al., *Science* 248:1120–1122 (1990), have demonstrated that the APP gene is tightly linked to hereditary cerebral hemorrhage with amyloidosis (HCHWA-D) in two Dutch families. This was confirmed by the finding of a point mutation in the APP coding region in two Dutch patients (Levy et al., *Science* 248:1124–1128 (1990)). The mutation substituted a glutamine for glutamic acid at position 22 of the Aβ (position 618 of APP695, or position 693 of APP770). In addition, certain families are genetically predisposed to Alzheimer's disease, a condition referred to as familial Alzheimer's disease (FAD), through mutations resulting in an amino acid replacement at position 717 of the full length protein (Goate et al. (1991); Murrell et al. (1991); Chartier-Harlin et al. (1991)). These mutations co-segregate with the disease within the families and are absent in families with late-onset AD. This mutation at amino acid 717 increases the production of the $A\beta_{1-42}$ form of Aβ from APP (Suzuki et al., *Science* 264.1336–1340 (1994)). Another mutant form contains a change in amino acids at positions 670 and 671 of the full length protein (Mullan et al. (1992)). This mutation to amino acids 670 and 671 increases the production of total Aβ from APP (Citron et al., *Nature* 360:622–674 (1992)).

There are no robust animal models to study AD, although aging nonhuman primates seem to develop amyloid plaques of Aβ in brain parenchyma and in the walls of some meningeal and cortical vessels. Although aged primates and canines can serve as animal models, they are expensive to maintain, need lengthy study periods, and are quite variable in the extent of pathology that develops.

There are no spontaneous animal mutations with sufficient similarities to AD to be useful as experimental models. Various models have been proposed in which some AD-like symptoms may be induced by electrolysis, transplantation of AD brain samples, aluminum chloride, kainic acid or choline analogs (Kisner et al., *Neurobiol. Aging* 7:287–292 (1986); Mistry et al., *J Med Chem* 29:337–343 (1986)). Flood et al., *Proc. Natl. Acad. Sci.* 88:3363–3366 (1986), reported amnestic effects in mice of four synthetic peptides homologous to the Aβ. Because none of these share with AD either common symptoms, biochemistry or pathogenesis, they are not likely to yield much useful information on etiology or treatment.

Several transgenic rodent lines have been produced that express either the human APP gene or human APP complementary DNA regulated by a variety of promoters. Transgenic mice with the human APP promoter linked to *E. coli* β-galactosidase (Wirak et al., *The EMBO J* 10:289–296 (1991)) as well as transgenic mice expressing the human APP751 cDNA (Quon et al. *Nature* 352:239–241 (1991)) or subfragments of the cDNA including the Aβ (Wirak et al., *Science* 253:323–325 (1991); Sandhu et al., *J. Biol. Chem.* 266:21331–21334 (1991); Kawabata et al., *Nature* 354:476–478 (1991)) have been produced. Results obtained in the different studies appear to depend upon the source of promoter and the protein coding sequence used. For example, Wirak et al., *Science* 253:323–325 (1991), found that in transgenic mice expressing a form of the Aβ, intracellular accumulation of "amyloid-like" material, reactive with antibodies prepared against Aβ were observed but did not find other histopathological disease symptoms. The intracellular nature of the antibody-reactive material and the lack of other symptoms suggest that this particular transgenic animal is not a faithful model system for Alzheimer's disease. Later studies have shown that similar staining is seen in non-transgenic control mice and Wirak et al., *Science* 253:323–325 (1991) was partially retracted in a comment in *Science* 255:143–145 (1992). Thus, the staining seen by Wirak et al. appears to be artifactual.

Kawabata et al. (1991) report the production of amyloid plaques, neurofibrillary tangles, and neuronal cell death in their transgenic animals. In each of these studies, Aβ or a fragment containing Aβ was expressed. Wirak et al. (1991), used the human APP promoter while Kawabata et al. (1991) used the human thy-1 promoter. However, Kawabata et al. (1991) was later retracted by Kawabata et al., *Nature* 356:23 (1992) and Kawabata et al., *Nature* 356:265 (1992). In transgenic mice expressing the APP751 cDNA from the neuron-specific enolase promoter of Quon et al. (1991), rare, small extracellular deposits of material reactive with antibody prepared against synthetic Aβ were observed. A review of the papers describing these early transgenic mice indicate that do not produce characteristic Alzheimer pathologies (see Marx, *Science* 255:1200–1202 (1992)).

Transgenic mice expressing APP751 from a neuron-specific enolase (NSE) promoter were recently described by McConlogue et al., *Neurobiol. Aging* 15:S12 (1994), Higgins et al., *Ann Neurol.* 35:598–607 (1995), Mucke et al., *Brain Res.* 666:151–167 (1994), Higgins et al., *Proc. Natl. Acad. Sci. USA* 92:4402–4406 (1995), and U.S. Pat. No. 5,387,742 to Cordell. Higgins et al., *Ann Neurol.* 35:598–607 (1995) describe results with the same mice as described by Quon et al. (1991). Such mice have only sparse Aβ deposits which are more typical of very early AD and young Down's syndrome cases. The deposits seen in this transgenic mouse were also seen, although at a lower abundance, in non-transgenic control animals. Mature lesions such as frequent compacted plaques, neuritic dystrophy and extensive gliosis are not seen in these mice (Higgins et al., *Ann Neurol.* 35:598–607 (1995)). McConlogue et al. (1994) reported finding no Aβ deposits in these mice.

Transgenic mice in which APP is expressed from the neuronal specific synaptophysin promoter express APP at low levels equivalent to that in brain tissue from the NSE APP mice described above. These mice were also reported not to display any brain lesions (Higgins et al.).

Transgenic mice containing yeast artificial chromosome (YAC) APP constructs have also been made (Pearson and Choi, *Proc. Natl. Acad. Sci. USA* 90:10578–10582 (1993); Lamb et al., *Nature Genetics* 5:22–30 (1993); Buxbaum et al., *Biochem. Biophys. Res. Comm.* 197:639–645 (1993)). These mice contain the entire human APP genomic gene and express human APP protein at levels similar to endogenous APP; higher levels of expression than that obtained in mice using the NSE promoter. None of these mice, however, show evidence of pathology similar to AD.

Alzheimer's disease animal models, including transgenic models, have been recently reviewed by Lannfelt et al., Behavioural Brain Res. 57:207–213 (1993), and Fukuchi et al., Ann. N. Y. Acad. Sci. 695:217–223 (1993). Lannfelt et al. points out that none of the prior transgenic animals that show apparent plaques demonstrate neuropathological changes characteristic of AD. Lannfelt et al. also discusses possible reasons for the "failure" of previous transgenic animal models. Similarly, Fukuchi et al. discusses the failure of prior transgenic animal models to display most of the characteristics known to be associated with AD. For example, the transgenic mouse reported by Quon et al. is reported to produce Aβ immunoreactive deposits that stain only infrequently with thioflavin S and not at all with Congo Red, in contrast to the staining pattern of AD Aβ deposits.

Alzheimer's disease is characterized by numerous changes in the expression levels of various proteins, the biochemical activity and histopathology of brain tissue, as well as cognitive changes in affected individuals. Such characteristic changes associated with AD have been well documented. The most prominent change, as noted above, is the deposition of Aβ into amyloid plaques (Haass and Selkoe, Cell 75:1039–1042 (1993)). A variety of other molecules are also present in plaques, such as apolipoprotein E, laminin, amyloid P component, and collagen type IV (Kalaria and Perry, Brain Research 631:151–155 (1993); Ueda et al., Proc. Natl. Aca. Sci. USA 90:11282–11286 (1993)). Changes in cytoskeletal markers have also been associated with AD, such as the changes in microtubule-associated protein tau, MAP-2 or neurofilaments (Kosik et al., Science 256: 780–783 (1992); Lovestone and Anderton, Current Opinion in Neurology & Neurosurgery 5:883–888 (1992); Brandan and Inestrosa, General Pharmacology 24:1063–1068 (1993); Trojanowski et al., Brain Pathology 3:45–54 (1993); Masliah et al., American Journal of Pathology 142:871–882 (1993)). Alzheimer's disease is also known to stimulate an immunoinflammatory response, increasing such inflammatory markers as glial fibrillary acidic protein (GFAP), α2-macroglobulin, and interleukins 1 and 6 (IL-1 and IL-6) (Frederickson and Brunden, Alzheimer Disease and Associated Disorders 8:159–165 (1994); McGeer et al., Canadian Journal of Neurological Sciences 18:376–379 (1991); Wood et al., Brain Research 629:245–252 (1993)). Finally, neuronal and neurotransmitter changes have been associated with AD, such as the cholinergic, muscarinic, serotinergic, adrenergic, and adensosine receptor systems (Rylett et al., Brain Res 289:169–175 (1983); Sims et al., Lancet 1:333–336 (1980); Nitsch et al., Science 258:304–307 (1992); Masliah and Terry, Clinical Neuroscience 1:192–198 (1993); Greenamyre and Maragos, Cerebrovascular and Brain Metabolism Reviews 5:61–94 (1993); McDonald and Nemeroff, Psychiatric Clinics of North America 14:421–422 (1991); Mohr et al., Journal of Psychiatry & Neuroscience 19:17–23 (1994)).

It is therefore an object of the present invention to provide an animal model for Alzheimer's disease that is constructed using transgenic technology.

It is a further object of the present invention to provide transgenic animals characterized by certain genetic abnormalities in the expression of the amyloid precursor protein.

It is a further object of the present invention to provide transgenic animals exhibiting one or more histopathologies similar to those of Alzheimer's disease.

It is a further object of the present invention to provide transgenic animals expressing one or more Aβ-containing proteins at high levels in brain tissue.

It is a further object of the present invention to provide a method of screening potential drugs for the treatment of Alzheimer's disease using transgenic animal models.

SUMMARY OF THE INVENTION

The construction of transgenic animal models for testing potential treatments for Alzheimer's disease is described. The models are characterized by a greater similarity to the conditions existing in naturally occurring Alzheimer's disease, based on the ability to control expression of one or more of the three major forms of the β-amyloid precursor protein (APP), APP695, APP751, and APP770, or subfragments thereof, as well as various point mutations based on naturally occurring mutations, such as the FAD mutations at amino acid 717, and predicted mutations in the APP gene. The APP gene constructs are prepared using the naturally occurring APP promoter of human, mouse, or rat origin, efficient promoters such as human platelet derived growth factor β chain (PDGF-B) gene promoter, as well as inducible promoters such as the mouse metallothionine promoter, which can be regulated by addition of heavy metals such as zinc to the animal's water or diet. Neuron-specific expression of constructs can be achieved by using the rat neuron specific enolase promoter.

The constructs are introduced into animal embryos using standard techniques such as microinjection or embryonic stem cells. Cell culture based models can also be prepared by two methods. Cells can be isolated from the transgenic animals or prepared from established cell cultures using the same constructs with standard cell transfection techniques.

The constructs disclosed herein generally encode all or a contiguous portion of one of the three forms of APP: APP695, APP751, or APP770, preferably an Aβ-containing protein, as described herein. Examples of Aβ-containing proteins are proteins that include all or a contiguous portion of APP770, APP770 bearing a mutation in amino acid 669, 670, 671, 690, 692, and/or 717, APP751, APP751 bearing a mutation in amino acid 669, 670, 671, 690, 692, and/or 717, APP695, and APP695 bearing a mutation in amino acid 669, 670, 671, 690, 692, and/or 717, where each of these Aβ-containing proteins includes amino acids 672 to 714 of human APP. Some specific constructs that are described employ the following protein coding sequences: the APP770 cDNA; the APP770 cDNA bearing a mutation at amino acid 669, 670, 671, 690, 692, 717, or a combination of these mutations; the APP751 cDNA containing the KPI protease inhibitor domain without the OX-2 domain in the construct; the APP751 cDNA bearing a mutation at amino acid 669, 670, 671, 690, 692, 717, or a combination of these mutations; the APP695 cDNA; the APP695 cDNA bearing a mutation at amino acid 669, 670, 671, 690, 692, 717, or a combination of these mutations; APP695, APP751, or APP770 cDNA truncated at amino acid 671 or 685, the sites of β-secretase or α-secretase cleavage, respectfully; APP cDNA truncated to encode amino acids 646 to 770 of APP; APP cDNA truncated to encode amino acids 646 to 770 of APP and including at least one intron; the APP leader sequence followed by the Aβ region (amino acids 672 to 714 of APP) plus the remaining carboxy terminal 56 amino acids of APP; the APP leader sequence followed by the Aβ region plus the remaining carboxy terminal 56 amino acids with the addition of a mutation at amino acid 717; the APP leader sequence followed by the Aβ region; the Aβ region plus the remaining carboxy terminal 56 amino acids of APP; the Aβ region plus the remaining carboxy terminal 56 amino acids of APP with the addition of a mutation at amino acid 717; a combination cDNA/genomic APP gene construct; a combination cDNA/genomic APP gene construct with the addition of a mutation at amino acid 669, 670, 671, 690, 692, 717, or a combination of these mutations; a combination cDNA/genomic APP gene construct truncated at amino acid 671 or 685; and an APP cDNA construct containing at least amino acids 672 to 722 of APP.

These protein coding sequences are operably linked to leader sequences specifying the transport and secretion of the encoded Aβ related protein. A preferred leader sequence is the APP leader sequence. These combined protein coding sequences are in turn operably linked to a promoter that causes high expression of Aβ in transgenic animal brain tissue. A preferred promoter is the human platelet derived growth factor β chain (PDGF-B) gene promoter. Additional constructs include a human yeast artificial chromosome construct controlled by the PDGF-B promoter; a human yeast artificial chromosome construct controlled by the PDGF-B promoter with the addition of a mutation at amino acid 669, 670, 671, 690, 692, 717, or a combination of these mutations; the endogenous mouse or rat APP gene modified through the process of homologous recombination between the APP gene in a mouse or rat embryonic stem (ES) cell and a vector carrying the human APP cDNA bearing a mutation at amino acid position 669, 670, 671, 690, 692, 717, or a combination of these mutations, such that sequences in the resident rodent chromosomal APP gene beyond the recombination point (the preferred site for recombination is within APP exon 9) are replaced by the analogous human sequences bearing a mutation at amino acid 669, 670, 671, 690, 692, 717, or a combination of these mutations. These constructs can be introduced into the transgenic animals and then combined by mating of animals expressing the different constructs.

The transgenic animals, or animal cells, are used to screen for compounds altering the pathological course of Alzheimer's disease as measured by their effect on the amount and/or histopathology of Alzheimer's disease markers in the animals, as well as by behavioral alterations. These markers include APP and APP cleavage products; Aβ; other plaque related molecules such as apolipoprotein E, laminin, and collagen type IV; cytoskeletal markers, such as spectrin, tau, neurofilaments, and MAP-2; inflammatory markers, such as GFAP, α2-macroglobulin, IL-1, and IL-6; and neuronal and synaptic neurotransmitter related markers, such as GAP43 and synaptophysin, and those associated with the cholinergic, muscarinic, serotinergic, adrenergic, and adenosine receptor systems.

BRIEF DESCRIPTION OF THE DRAWINGS

The boxed portions of the drawings indicate the amino acid coding portions of the constructs. Filled portions indicate the various domains of the protein as indicated in the Figure Legend. Lines indicate sequences in the clones that are 5' or 3' untranslated sequences, flanking genomic sequences, or introns. The break in the line to the left of the constructs in FIGS. 7a and 7b and FIGS. 8a and 8b indicates the presence of a long DNA sequence.

FIG. 1a is a schematic of the APP770 cDNA coding sequence.

FIG. 1b is a schematic of the APP770 cDNA coding sequence bearing a mutation at position 717.

FIG. 2a is a schematic of the APP751 cDNA coding sequence.

FIG. 2b is a schematic of the APP751 cDNA coding sequence bearing a mutation at position 717.

FIG. 3a is a schematic of the APP695 coding sequence.

FIG. 3b is a schematic of the APP695 cDNA coding sequence bearing a mutation at position 717.

FIG. 6a is a schematic of a combination cDNA/genomic coding sequence allowing alternative splicing of the KPI and OX-2 exons.

FIG. 6b is a schematic of a combination cDNA/genomic coding sequence bearing a mutation at position 717 and allowing alternative splicing of the KPI and OX-2 exons.

FIG. 7a is a schematic of a human APP YAC coding sequence.

FIG. 7b is a schematic of a human APP YAC coding sequence bearing a mutation at position 717.

FIGS. 8a and 8b are schematics of genetic alteration of the mouse APP gene by homologous recombination between the mouse APP gene in a mouse ES cell and a vector carrying the human APP cDNA (either of the wild-type (FIG. 8a) or FAD mutant form (FIG. 8b)) directed to the exon 9 portion of the gene. As a result of this recombination event, sequences in the resident mouse chromosomal APP gene beyond the recombination point in exon 9 are replaced by the analogous human sequences.

DETAILED DESCRIPTION OF THE INVENTION

Figure 4A:
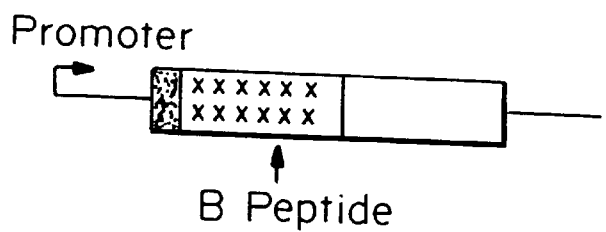
FIG. 4a is a schematic of a coding sequence for the carboxy terminal portion of APP.
Figure 4B:
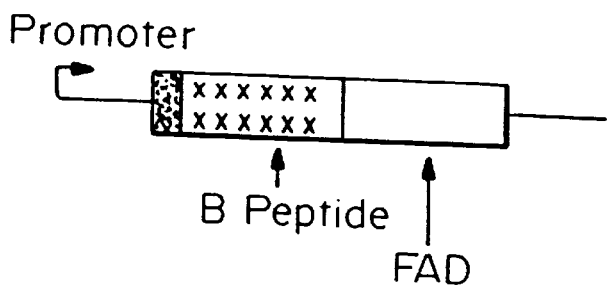
FIG. 4b is a schematic of a coding sequence for the carboxy terminal portion of APP bearing a mutation at position 717.

The constructs and transgenic animals and animal cells are prepared using the methods and materials described below.

Sources of Materials.

Restriction endonucleases are obtained from conventional commercial sources such as New England Biolabs (Beverly, Mass.), Promega Biological Research Products (Madison, Wis.), and Stratagene (La Jolla Calif.). Radioactive materials are obtained from conventional commercial sources such as Dupont/NEN or Amersham. Custom-designed oligonucleotides for site-directed mutagenesis are available from any of several commercial providers of such materials such as Bio-Synthesis Inc., Lewisville, Tex. Kits for carrying out site-directed mutagenesis are available from commercial suppliers such as Promega Biological Research Products and Stratagene. Clones of cDNA including the APP695, APP751, and APP770 forms of APP mRNA were obtained directly from Dr. Dmitry Goldgaber, NIH. Libraries of DNA are available from commercial providers such as Stratagene, La Jolla, Calif., or Clontech, Palo Alto, Calif. PC12 and 3T3 cells were obtained from ATCC (#CRL1721 and #CCL92, respectively). An additional PC12 cell line was obtained from Dr. Charles Marotta of Harvard Medical School, Massachusetts General Hospital, and McLean Hospital. Standard cell culture media appropriate to the cell line are obtained from conventional commercial sources such as Gibco/BRL. Murine stem cells, strain D3, were obtained from Dr. Rolf Kemler (Doetschman et al., *J. Embryol. Exp. Morphol.* 87:27 (1985)). Lipofectin for DNA transfection and the drug G418 for selection of stable transformants are available from Gibco/BRL.

Definition of APP cDNA Clones.

The cDNA clone APP695 is of the form of cDNA described by Kang et al., *Nature* 325:733–735 (1987), and represents the most predominant form of APP in the brain. The cDNA clone APP751 is of the form described by Ponte et al., *Nature* 331:525–527 (1988). This form contains an insert of 168 nucleotides relative to the APP695 cDNA. The 168 nucleotide insert encodes the KPI domain. The cDNA clone APP770 is of the form described by Kitaguchi et al. *Nature* 331:530–532 (1988). This form contains an insert of 225 nucleotides relative to the APP695 cDNA. This insert includes the 168 nucleotides present in the insert of the APP751 cDNA, as well as an addition 57 nucleotide region that does not appear in APP751 cDNA. The 225 nucleotide insert encodes for the KPI domain as well as the OX-2 domain. All three forms arise from the same precursor RNA transcript by alternative splicing. The 168 nucleotide insert is present in both APP751 cDNA and APP770 cDNA.

The sequence encoding APP695 is shown in SEQ ID NO:1. This sequence begins with the first base of the initiation codon AUG and encodes a 695 amino acid protein. The region from nucleotide 1789 to 1917 of SEQ ID NO:1 encodes the Aβ. The amino acid sequence of APP695 is shown in SEQ ID NO:2. Amino acids 597 to 639 of SEQ ID NO:2 form the Aβ. The amino-acid composition of the APP695 is A57, C12, D47, E85, F17, G31, H25, I23, K38, L52, M21, N28, P31, Q33, R33, S30, T45, V62, W8, Y17 resulting in a calculated molecular weight of 78,644.45. These sequences are derived from Kang et al. (1988).

The sequence encoding APP751 is shown in SEQ ID NO:3. This sequence begins with the first base of the initiation codon AUG and encodes a 751 amino acid protein. Nucleotides 866 to 1033 of SEQ ID NO:3 do not appear in APP695 cDNA. The region from nucleotide 1957 to 2085 of SEQ ID NO:3 encodes the Aβ. The amino acid sequence of APP751 is shown in SEQ ID NO:4. Amino acids 289 to 345 of SEQ ID NO:4 do not appear in APP695. This 57 amino acid region includes the KPI domain. Amino acids 653 to 695 of SEQ ID NO:4 form the Aβ. These sequences are derived from Ponte et al. (1988).

The sequence encoding APP770 is shown in SEQ ID NO:5. This sequence begins with the first base of the initiation codon AUG and encodes a 770 amino acid protein. Nucleotides 866 to 1090 of SEQ ID NO:5 do not appear in APP695 cDNA. Nucleotides 1034 to 1090 of SEQ ID NO:5 do not appear in APP751 cDNA. The region from nucleotide 2014 to 2142 encodes the Aβ. The amino acid sequence of APP770 is shown in SEQ ID NO:6. Amino acids 289 to 364 of SEQ ID NO:6 do not appear in APP695. This 76 amino acid region includes the KPI and OX-2 domains. Amino acids 345 to 364 of SEQ ID NO:6 do not appear in APP751. This 20 amino acid region includes the OX-2 domain. Amino acids 672 to 714 form the Aβ. A probable membrane-spanning region of the APP occurs from amino acid 700 to 723. Unless otherwise stated, all references herein to nucleotide positions refer to the numbering of SEQ ID NO:5. This is the numbering derived from the APP770 cDNA. Unless otherwise stated, all references herein to amino acid positions refer to the numbering of SEQ ID NO:6. This is the numbering derived from APP770. According to this numbering convention, for example, amino acid position 717 refers to amino acid 717 of APP770, amino acid 698 of APP751, and amino acid 642 of APP695. The above sequences are derived from Kang et al. (1988) and Kitaguchi et al. (1988).

Unless otherwise noted, all forms of APP and fragments of APP, including all forms of Aβ, referred to herein are based on the human APP amino acid sequence. For example, Aβ refers to the human Aβ, APP refers to human APP, and APP770 refers to human APP770. As used herein, the term cDNA refers not only to DNA molecules actually prepared by reverse transcription of mRNA, but also any DNA molecule encoding a protein where the coding region is not interrupted, that is, a DNA molecule having a continuous open reading frame encoding a protein. As such, the term cDNA as used herein provides a convenient means of referring to a protein encoding DNA molecule where the protein encoding region is not interrupted by intron sequences (or any other sequences not encoding protein).

Definition of the APP Genomic Locus.

Characterization of phage and cosmid clones of human genomic DNA clones listed in Table 1 below originally established a minimum size of at least 100 kb for the Alzheimer's gene. There are a total of 18 exons in the APP gene (Lemaire et al., *Nucl. Acid Res* 17:517–522 (1989); Yoshikai et al. (1990); Yoshikai et al., *Nucleic Acids Res* 102:291–292 (1991)). Yoshikai et al. (1990) describes the sequences of the exon-intron boundaries of the APP gene. These results taken together indicate that the miniimum size of the Alzheimer's gene is 175 kb.

TABLE 1

Alzheimer's Cosmid and Lambda Clones.

| Library | Name of Clone | Insert Size (kb) | Assigned APP Region |
|---|---|---|---|
| Cosmid | 1 GPAPP47A | 35 | 25 kb promoter & 9 kb intron 1 |
| | 2 GPAAP36A | 35 | 12 kb promoter & 22 kb intron 1 |
| | 3 GAPP30A | 30–35 | 5' coding region |
| | 4 GAPP43A | 30–35 | exons 9, 10 and 11 |
| Lambda | 1 GAPP6A | 12 | exon 6 |
| | 2 GAPP6B | 18 | exons 4 and 5 |
| | 3 GPAPP20A | 20 | exon 6 |
| | 4 GAPP20B | 17 | exons 4 and 5 |
| | 5 GAPP28A | 18 | exons 4 and 5 |
| | 6 GAPP3A | 14 | exon 6 |
| | 7 GAPP4A | 19 | exon 6 |
| | 8 GAPP10A | 16 | exons 9, 10 and 11 |
| | 9 GAPP16A | 21 | exon 6 |

Table 2 indicates where the 17 introns interrupt the APP coding sequence. The numbering refers to the nucleotide positions of APP770 cDNA as shown in SEQ ID NO:5. The starting nucleotide of exon 1 represents the first transcribed nucleotide. It is negative because the +1 nucleotide is the first nucleotide of the AUG initiator codon by convention (Kang et al. (1988)). The ending nucleotide of exon 18 represents the last nucleotide present in the mRNA prior to the poly(A) tail (Yoshikai et al. (1990)). It has been discovered that Yoshikai et al. (1990) and Yoshikai et al. (1991)

contain an error in the location of exon 8. FIG. 1 of Yoshikai et al. (1991) includes an EcoRI fragment between EcoRI fragments containing exon 7 and exon 8. In fact, this intervening EcoRI fragment is actually located immediately after exon 8, so that the EcoRI fragment containing exon 7 and the EcoRI fragment containing exon 8 are adjacent to each other.

TABLE 2

Location of Introns in APP Gene Sequence.

| | Starting nucleotide | Ending nucleotide | Following Intron |
|---|---|---|---|
| Exon 1 | −146 | 57 | Intron 1 |
| Exon 2 | 58 | 225 | Intron 2 |
| Exon 3 | 226 | 355 | Intron 3 |
| Exon 4 | 356 | 468 | Intron 4 |
| Exon 5 | 469 | 662 | Intron 5 |
| Exon 6 | 663 | 865 | Intron 6 |
| Exon 7 | 866 | 1033 | Intron 7 |
| Exon 8 | 1034 | 1090 | Intron 8 |
| Exon 9 | 1091 | 1224 | Intron 9 |
| Exon 10 | 1225 | 1299 | Intron 10 |
| Exon 11 | 1300 | 1458 | Intron 11 |
| Exon 12 | 1459 | 1587 | Intron 12 |
| Exon 13 | 1588 | 1687 | Intron 13 |
| Exon 14 | 1688 | 1909 | Intron 14 |
| Exon 15 | 1910 | 1963 | Intron 15 |
| Exon 16 | 1964 | 2064 | Intron 16 |
| Exon 17 | 2065 | 2211 | Intron 17 |
| Exon 18 | 2212 | 3432 | |

APP Gene Mutations.

Certain families are genetically predisposed to Alzheimer's disease, a condition referred to as familial Alzheimer's disease (FAD), through mutations resulting in an amino acid replacement at position 717 of the full length protein (Goate et al. (1991); Murrell et al. (1991); Chartier-Harlin et al. (1991)). These mutations co-segregate with the disease within the families. For example, Murrell et al. (1991) described a specific mutation found in exon 17 (which Murrell et al. refers to as exon 15) where the valine of position 717 is replaced by phenylalanine.

Another FAD mutant form contains a change in amino acids at positions 670 and 671 of the full length protein (Mullan et al. (1992)). In one form of this mutation, the lysine at position 670 is replaced by asparagine and the methionine at position 671 is replaced by leucine. The effect of this mutation is to increase the production of Aβ in cultured cells approximately 7-fold (Citron et al., Nature 360: 672–674 (1992); Lai et al., Science 259:514–516 (1993)). Replacement of the methionine at position 671 with leucine by itself has also been shown to increase production of Aβ. Additional mutations in APP at amino acids 669, 670, and 671 have been shown to reduce the amount of Aβ processed from APP (Citron et al., Neuron 14:661–670 (1995)). The APP construct with Val at amino acid 690 produces an increased amount of a truncated form of Aβ.

APP expression clones can be constructed that bear a mutation at amino acid 669, 670, 671, 690, 692, or 717 of the full length protein. The mutations from Lys to Asn and from Met to Leu at amino acids 670 and 671, respectively, are sometimes referred to as the Swedish mutation. Additional mutations can also be introduced at amino acids 669, 670, or 671 which either increase or reduce the amount of Aβ processed from APP. Mutations at these amino acids in any APP clone or transgene can be created by site-directed mutagenesis (Vincent et al., Genes & Devel. 3:334–347 (1989)), or, once made, can be incorporated into other constructs using standard genetic engineering techniques.

Some mutations at amino acid 717 are sometimes referred to as the Hardy mutation. Such mutations can include conversion of the wild-type Val717 codon to a codon for Ile, Phe, Gly, Tyr, Leu, Ala, Pro, Trp, Met, Ser, Thr, Asn, or Gln. A preferred substitution for Val717 is Phe. These mutations predispose individuals expressing the mutant proteins to develop Alzheimer's disease. It is believed that the mutations affect the expression and/or processing of APP, shifting the balance toward Alzheimer's pathology. Mutations at amino acid 669 can include conversion of the wild-type Val669 codon to a codon for Trp, or deletion of the codon. Mutations at amino acid 670 can include conversion of the wild-type Lys670 codon to a codon for Asn or Glu, or deletion of the codon. Mutations at amino acid 671 can include conversion of the wild-type Met671 codon to a codon for Leu, Val, Lys, Tyr, Glu, or Ile, or deletion of the codon. A preferred substitution for Lys670 is Asn, and a preferred substitution for Met671 is Leu. These mutations predispose individuals expressing the mutant proteins to develop Alzheimer's disease. The other listed mutations to amino acids 669, 670, and 671 are known to reduce the amount of Aβ processed from APP (Citron et al. (1995)). It is believed that these mutations affect processing of APP leading to a change in Aβ production.

Truncated forms of APP can also be expressed from transgene constructs. For example, APP cDNA truncated to encode amino acids 646 to 770 of APP. The APP cDNA construct truncated to encode amino acids 646 to 770 of APP, and operatively linked to the PDGF-B promoter, is referred to as PDAPPc125.

Nucleic Acid Constructs Encoding Aβ-containing Proteins.

Constructs for use in transgenic animals include a promoter for expression of the construct in a mammalian cell and a region encoding a protein that includes all or a contiguous portion of one of the three forms of APP: APP695, APP751, or APP770, with or without specific amino acid mutations as described herein. It is preferred that protein encoded is an Aβ-containing protein. As used herein, an Aβ-containing protein is a protein that includes all or a contiguous portion of one of the three forms of APP: APP695, APP751, or APP770, with or without specific amino acid mutations as described herein, where the protein includes all or a portion of amino acids 672 to 714 of human APP. Preferred Aβ-containing proteins include amino acids 672 to 714 of human APP. Preferred forms of such Aβ-containing proteins include all or a contiguous portion of APP770, APP770 bearing a mutation in amino acid 669, 670, 671, 690, 692, and/or 717, APP751, APP751 bearing a mutation in amino acid 669, 670, 671, 690, 692, and/or 717, APP695, and APP695 bearing a mutation in amino acid 669, 670, 671, 690, 692, and/or 717, where each of these Aβ-containing proteins includes amino acids 672 to 714 of human APP.

Preferred forms of the above Aβ-containing proteins are APP770; APP770 bearing a mutation in the codon encoding one or more amino acids selected from the group consisting of amino acid 669, 670, 671, 690, 692, 717; APP751; APP751 bearing a mutation in the codon encoding one or more amino acids selected from the group consisting of amino acid 669, 670, 671, 690, 692, 717; APP695; APP695 bearing a mutation in the codon encoding one or more amino acids selected from the group consisting of amino acid 669, 670, 671, 690, 692, 717; a protein consisting of amino acids 646 to 770 of APP; a protein consisting of amino acids 670 to 770 of APP; a protein consisting of amino acids 672 to 770 of APP; and a protein consisting of amino acids 672 to 714 of APP.

In the constructs disclosed herein, the DNA encoding the Aβ-containing protein can be cDNA or a cDNA/genomic DNA hybrid, wherein the cDNA/genomic DNA hybrid includes at least one APP intron sequence wherein the intron sequence is sufficient for splicing.

Preferred constructs contain DNA encoding APP770; DNA encoding APP770 bearing a mutation in the codon encoding amino acid 669, 670, 671, 690, 692, 717, or a combination of these mutations; a fragment of DNA encoding APP770 which encodes an amino acid sequence comprising amino acids 672 to 714 of APP770; DNA encoding APP751; DNA encoding APP751 bearing a mutation in the codon encoding amino acid 669, 670, 671, 690, 692, 717, or a combination of these mutations; a fragment of DNA encoding APP751 which encodes an amino acid sequence comprising amino acids 672 to 714 of APP770; DNA encoding APP695; DNA encoding APP695 bearing a mutation in the codon encoding amino acid 669, 670, 671, 690, 692, 717, or a combination of these mutations; a fragment of DNA encoding APP695 which encodes an amino acid sequence comprising amino acids 672 to 714 of APP770; APP cDNA truncated to encode amino acids 646 to 770 of APP; a combination cDNA/genomic DNA hybrid APP gene construct; a combination cDNA/genomic DNA hybrid APP gene construct bearing a mutation in the codon encoding amino acid 669, 670, 671, 690, 692, 717, or a combination of these mutations; or a combination cDNA/genomic DNA hybrid APP gene construct truncated at amino acid 671 or 685.

Preferred forms of such constructs are APP770 cDNA; APP770 cDNA bearing a mutation in the codon encoding amino acid 669, 670, 671, 690, 692, 717, or a combination of these mutations; a fragment of APP770 cDNA encoding an APP amino acid sequence, the amino acid sequence comprising amino acids 672 to 714 of APP770; APP751 cDNA; APP751 cDNA bearing a mutation in the codon encoding amino acid 669, 670, 671, 690, 692, 717, or a combination of these mutations; a fragment of APP751 cDNA encoding an APP amino acid sequence, the amino acid sequence comprising amino acids 672 to 714 of APP770; APP695 cDNA; APP695 cDNA bearing a mutation in the codon encoding amino acid 669, 670, 671, 690, 692, 717, or a combination of these mutations; a fragment of APP695 cDNA encoding an APP amino acid sequence, the amino acid sequence comprising amino acids 672 to 714 of APP770; APP cDNA truncated to encode amino acids 646 to 770 of APP; a combination cDNA/genomic DNA hybrid APP gene construct; a combination cDNA/genomic DNA hybrid APP gene construct bearing a mutation in the codon encoding amino acid 669, 670, 671, 690, 692, 717, and a combination of these mutations; and a combination cDNA/genomic DNA hybrid APP gene construct truncated at amino acid 671 or 685.

Construction of Transgenes.

Construction of various APP transgenes can be accomplished using any suitable genetic engineering technique, such as those described in Sambrook et al., *Molecular Cloning: A Laboratory Manual* (Cold Spring Harbor Laboratory, N.Y., 1989). Regions of APP clones that have been engineered or mutated can be interchanged by using convenient restriction enzyme sites present in APP cDNA clones. A NruI site starts at position −5 (relative to the first nucleotide of the AUG initiator codon). A KpnI and an Asp718 site both start at position 57 (these are isoschizomers leaving different sticky ends). A XcmI site starts at position 836 and cuts at position 843. A ScaI site starts at position 1004. A XhoI site starts at position 1135. A BamHI site starts at position 1554. A BglII site starts at position 1994. An EcoRI site starts at position 2020. A SpeI site starts at position 2583. Another EcoRI site starts at position 3076.

Figure 5:
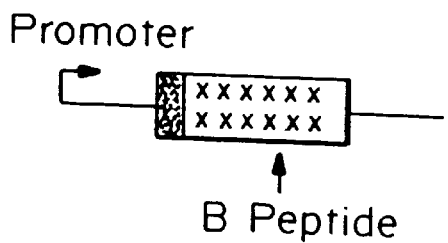
FIG. 5 is a schematic of a coding sequence for the Aβ portion of APP.

The clones bearing various portions of the human APP gene sequence shown in FIGS. 1a to 5 can be constructed in a common manner using standard genetic engineering techniques. For example, these clones can be constructed by first cloning the polyA addition signal from SV40 virus, as a 253 base pair BclI to BamHI fragment (Reddy et al., *Science* 200:494–502 (1978), into a modified vector from the pUC series. Next, the cDNA coding sequences (APP770, APP751, or APP695) can be inserted. Correct orientation and content of the fragments inserted can be determined through restriction endonuclease mapping and limited sequencing. The clones bearing various carboxy terminal portions of the human APP gene sequence shown in FIGS. 4a, 4b, and 5 can be constructed through several steps in addition to those indicated above. For example, an APP770 cDNA clone (SEQ ID NO:5) can be digested with Asp718 which cleaves after nucleotide position 57. The resulting 5' extension is filled in using the Klenow enzyme (Sambrook et al. (1989)) and ligated to a hexanucleotide of the following sequence: AGATCT, the recognition site for BglII. After cleavage with BglII, which also cuts after position 1994, and re-ligation, the translational reading frame of the protein is preserved. The truncated protein thus encoded contains the leader sequence, followed by approximately 6 amino acids that precede the Aβ, followed by the Aβ, and the 56 terminal amino acids of APP. The clone in FIG. 5 is created by converting the nucleotide at position 2138 to a T by site directed mutagenesis in the clone of FIG. 4a, thus creating a termination codon directly following the last amino acid codon of the Aβ. APP cDNA clones naturally contain an NruI site that cuts 2 nucleotides upstream from the initiator methionine codon. This site can be used for attachment of the different promoters used to complete each construct.

APP transgenes can also be constructed using PCR cloning techniques. Such techniques allow precise coupling of DNA fragments in the transgenes.

Combination cDNA/Genomic DNA Clones.

Endogenous APP expression results from transcription of precursor mRNA followed by alternative splicing to produce three main forms of APP. It is believed that this alternative splicing may be important in producing the pattern of APP expression involved in Alzheimer's disease. It is also believed that the presence of introns in expression constructs can influence the level and nature of expression by, for example, targeting precursor mRNA to mRNA processing and transport pathways (Huang et al., *Nucleic Acids Res.* 18:937–947 (1990)). Accordingly, transgenes combining cDNA and genomic DNA, which include intron sequences, are a preferred type of construct.

The RNA splicing mechanism requires only a few specific and well known consensus sequences. Such sequences have been identified in APP genomic DNA by Yoshikai et al. (1990). The disclosed transgenes can be constructed using one or more complete and intact intron sequences. However, it is preferred that the transgenes are constructed using truncated intron sequences that contain an effective amount of intron sequence to allow splicing. In general, truncated intron sequences that retain the splicing donor site, the splicing acceptor site, and the splicing branchpoint sequence will constitute an effective amount of an intron. The sufficiency of any truncated intron sequence can be determined by testing for the presence of correctly spliced mRNA in transgenic cells using methods described below.

Other intron sequences and splicing signals which are not derived from APP gene sequences may also be used in the transgene constructs. Such intron sequences will enhance expression of the transgene construct. A preferred heterologous intron is a hybrid between the adenovirus major late region first exon and intron junction and an IgG variable region splice acceptor. This hybrid intron can be constructed, for example, by joining the 162 bp PvuII to HindIII fragment of the adenovirus major late region, containing 8 bp of the first exon and 145 bp of the first intron, and the 99 bp HindIII to PstI fragment of the IgG variable region splice acceptor clone-6, as described by Bothwell et al., *Cell* 24:625–637 (1981). A similar splice signal has been shown to enhance expression of a construct to which it was attached, as described by Manley et al., *Nucleic Acids Res.* 18:937–947 (1990). It is preferred that the heterologous intron be placed between the promoter and the region encoding the APP.

Combination cDNA/genomic expression clones include (1) nucleic acid constructs containing a combination of APP cDNA encoding exons 1–6 and 9–18 and genomic APP sequences encoding introns 6, 7 and 8, and exons 7 and 8, and (2) nucleic acid constructs that do not contain a combination of APP cDNA encoding exons 1–6 and 9–18 and genomic APP sequences encoding introns 6, 7 and 8, and exons 7 and 8.

A preferred APP combination cDNA/genomic expression clone includes an effective amount of introns 6, 7 and 8, as shown in FIGS. 6a and 6b. Such a transgene can be constructed as follows. A preferred method of construction is described in Example 5. A plasmid containing the cDNA portion of the clone can be constructed by first converting the TaqI site at position 860 in an APP770 cDNA clone to an XhoI site by site-directed mutagenesis. Cleavage of the resulting plasmid with XhoI cuts at the new XhoI site and a pre-existing XhoI site at position 1135, and releases the KPI and OX-2 coding sequence. The plasmid thus generated serves as the acceptor for the KPI and OX-2 alternative splicing cassette.

The alternative splicing cassette can be created through a series of cloning steps involving genomic DNA. First, the TaqI site at position 860 in a genomic clone containing exon 6 and the adjacent downstream intron can be converted to an XhoI site by site-directed mutagenesis. Cleavage of the resulting plasmid with XhoI cuts at the new XhoI site and an XhoI site within either intron 6 or 7. This fragment, containing a part of exon 6 and at least a part of adjacent intron 6, can then be cloned into the XhoI site in a plasmid vector. Second, a genomic clone containing exon 9 and the adjacent upstream genomic sequences is cleaved with XhoI, cleaving the clone at the XhoI site at position 1135 (position 910 using the numbering system of Kang et al. (1987)) and an XhoI site in either intron 7 or 8. This fragment, containing a part of exon 9 and at least a part of adjacent intron 8, can then be cloned into the XhoI site of another plasmid vector. These two exon/intron junction fragments can then be released from their respective plasmid vectors by cleavage with XhoI and either BamHI or BglII, and cloned together into the XhoI site of another plasmid vector. It is preferred that the exon/intron junction fragments be excised with BamHI. It is most preferable that BamHI sites are engineered in the intron portion of the exon/intron junction fragments prior to their excision. This allows the elimination of lengthy extraneous intron sequences from the cDNA/genomic clone.

The XhoI fragment resulting from cloning the two exon/intron junction fragments together can be cleaved with either BamHI or BglII, depending on which enzyme was used for excision step above, and the genomic 6.8 kb BamHI segment, containing the KPI and OX-2 coding region along with their flanking intron sequences, can be inserted. This fragment was identified by Kitaguchi et al. (1988) using Southern blot analysis of BamHI-digested lymphocyte DNA from one normal individual and eight Alzheimer's disease patients using a 212 bp TaqI-AvaI fragment, nucleotides 862 to 1,073, of APP770 cDNA as the hybridization probe. Genomic DNA clones containing the region of the 225 bp insert can be isolated, for example, from a human leukocyte DNA library using the 212 bp TaqI-AvaI fragment as a probe. In the genomic DNA, the 225 bp sequence is located in a 168 bp exon (exon 7) and a 57 bp exon (exon 8), separated by an intron of approximately 2.6 kb (intron 7), with both exons flanked by intron-exon consensus sequences. The exon 7 corresponds to nucleotides 866 to 1,033 of APP770, and the exon 8 to nucleotides 1,034 to 1,090. Exon 7 encodes the highly conserved region of the Kunitz-type protease inhibitor family domain.

After cleavage with XhoI, this alternative splicing cassette, containing both exon and intron sequences, can then be excised by cleavage with XhoI and inserted into the XhoI site of the modified APP770 cDNA plasmid (the acceptor plasmid) constructed above. These cloning steps generate a combination cDNA/genomic expression clone that allows cells in a transgenic animal to regulate the inclusion of the KPI and OX-2 domains by a natural alternative splicing mechanism. An analogous gene bearing a mutation at amino acid 669, 670, 671, 690, 692, 717, or a combination of these mutations, can be constructed either directly by in vitro mutagenesis. A mutation to amino acid 717 can also be made by using the mutated form of APP770 cDNA described above to construct an acceptor plasmid.

Promoters.

Different promoter sequences can be used to control expression of nucleotide sequences encoding Aβ-containing proteins. The ability to regulate expression of the gene encoding an Aβ-containing protein in transgenic animals is believed to be useful in evaluating the roles of the different APP gene products in AD. The ability to regulate expression of the gene encoding an Aβ-containing protein in cultured cells is believed to be useful in evaluating expression and processing of the different Aβ-containing gene products and may provide the basis for cell cultured drug screens. A preferred promoter is the human platelet derived growth factor β (PDGF-B) chain gene promoter (Sasahara et al., *Cell* 64:217–227 (1991)).

Preferred promoters for the disclosed APP constructs are those that, when operatively linked to the protein coding sequences, mediate expression of one or more of the following expression products to at least a specific level in brain tissue of a two to four month old animal transgenic for one of the disclosed APP constructs. The products and their expression levels are $A\beta_{tot}$ to a level of at least 30 ng/g (6.8 pmoles/g) brain tissue and preferably at least 40 ng/g (9.12 pmoles/g) brain tissue, $A\beta_{1-42}$ to a level of at least 8.5 ng/g (1.82 pmoles/g) brain tissue and preferably at least 11.5 ng/g (2.5 pmoles/g) brain tissue, full length APP (FLAPP) and APPα combined (FLAPP+APPα) to a level of at least 150 pmoles/g brain tissue, APPα to a level of at least 42 pmoles/g brain tissue, and mRNA encoding human Aβ-containing protein to a level at least twice that of mRNA encoding the endogenous APP of the transgenic animal. $A\beta_{tot}$ is the total of all forms of Aβ. $A\beta_{1-42}$ is a form of Aβ having amino acids 1 to 42 of Aβ (corresponding to amino acids 672 to 714 of APP). FLAPP+APPα refers to APP forms containing the first 12 amino acids of the Aβ region (corresponding to amino acids 672 to 684 of APP). Thus, FLAPP+APPα represents a mixture of full length forms of APP and APP cleaved at the α-secretase site (Esch et al., Science 248:1122–1124 (1990)). APPβ is APP cleaved at the β-secretase site (Seubert et al., Nature 361:260–263 (1993)).

It is intended that the levels of expression described above refer to amounts of expression product present and are not limited to the specific units of measure used above. Thus, an expression level can be measured, for example, in moles per gram of tissue, grams per grams of tissue, moles per volume of tissue, and in grams per volume of tissue. The equivalence of these units of measure to the measures listed above can be determined using known conversion methods.

The levels of expression described above need not occur in all brain tissues. Thus, a promoter is considered preferred if at least one of the levels of expression described above occurs in at least one type of brain tissue. Where expression is tissue-specific, it is understood that if the expression level is sufficient in the specific brain tissue, the promoter is considered preferred even though the expression level in brain tissue as a whole may not, and need not, reach a threshold level. It is preferred that this level of expression is observed in hippocampal and/or cortical brain tissue. The promoter can mediate expression of the above expression products to the levels described above either constitutively or by induction. Induction can be accomplished by, for example, administration of an activator molecule, by heat, or by expression of a protein activator of transcription for the promoter operatively linked to the gene encoding an Aβ-containing protein. Many inducible expression systems which would be suitable for this purpose are known to those of skill in the art.

It is preferred that, in making the above measurements, the brain tissue is prepared by the following method. A brain from a transgenic test animal is dissected and the tissue is kept on ice throughout the homogenization procedure except as noted. The brain tissue is homogenized in 10 volumes (w/v) of 5 M guanidine-HCl, 50 mM Tris-HCl, pH 8.5. The sample is then gently mixed for 2 to 4 hours at room temperature. Homogenates are then diluted 1:10 in cold casein buffer #1 (0.25% casein/phosphate buffered saline (PBS) 0.05% sodium azide, pH 7.4, 1× protease inhibitor cocktail) for a final 0.5 M guanidine concentration and kept on ice. 100× protease inhibitor cocktail is composed of 2 mg/ml aprotinin, 0.5 M EDTA, pH 8.0, 1 mg/ml leupeptin. Diluted homogenates are then spun in an Eppendorf microfuge at 14,000 rpm for 20 minutes at 4° C. If further dilutions are required, they can be made with cold guanidine buffer #2 (1 part guanidine buffer #1 to 9 parts casein buffer #1).

It is preferred that the following assay be used to identify preferred promoters for their ability to mediate expression of Aβ to the levels described above. Antibody 266 (Seubert et al., Nature 359:325–327 (1992)) is dissolved at 10 μg/ml in buffer (0.23 g/L NaH$_2$PO$_4$-H$_2$O, 26.2 g/L NaHPO$_4$-7H$_2$O, 1 g/L sodium azide adjusted to pH 7.4) and 100 μl/well is coated onto 96-well immunoassay plates (Costar) and allowed to bind overnight. The plate is then aspirated and blocked for at least 1 hour with a 0.25% human serum albumin solution in 25 g/L sucrose, 10.8 g/L Na$_2$HPO$_4$-7H$_2$O, 1.0 g/L NaH$_2$PO$_4$-H$_2$O, 0.5 g/L sodium azide adjusted to pH 7.4. The 266 coated plate is then washed 1× with wash buffer (PBS/0.05% Tween 20) using a Skatron plate washer. 100 μl/well of Aβ1–40 standards and brain tissue samples are added to the plate in triplicate and incubated overnight at 4° C. Aβ1–40 standards are made from 0.0156, 0.0312, 0.0625, 0.125, 0.250, 0.500, and 1.000 μg/ml stocks in DMSO stored at −40° C. as well as a DMSO only control for background determination. Aβ standards consist of 1:100 dilution of each standard into guanidine buffer #3 (1 part BSA buffer to 9 parts guanidine buffer #1) followed by a 1:10 dilution into casein buffer #1 (Note: the final Aβ concentration range is 15.6 to 1000 pg/ml and the final guanidine concentration is 0.5 M). BSA buffer consists of 1% bovine serum albumin (BSA, immunoglobulin-free)/PBS/0.05% sodium azide. The plates and casein buffer #2 (0.25% casein/PBS/0.05% Tween 20/pH 7.4) are then brought to room temperature (RT). The plates are then washed 3× with wash buffer. Next, 100 μl/well of 3D6-biotin at 0.5 μg/ml in casein buffer #2 is added to each well and incubated at 1 hour at RT.

Monoclonal antibody 3D6 was raised against the synthetic peptide DAEFRGGC (SEQ ID NO:10) which was conjugated through the cysteine to sheep anti-mouse immunoglobulin. The antibody does not recognize secreted APP but does recognize species that begin at Aβ position 1 (Asp). For biotinylating 3D6, follow Pierce's NHS-Biotin protocol for labeling IgG (cat. #20217X) except use 100 mM sodium bicarbonate, pH 8.5 and 24 mg NHS-biotin per ml of DMSO.

The plates are then again washed 3× with wash buffer. Then, 100 μl/well of horseradish peroxidase (HRP)-avidin (Vector Labs, cat. # A-2004) diluted 1:4000 in casein buffer #2 is added to each well and incubated for 1 hour at RT. The plates are washed 4× with wash buffer and then 100 μl/well of TMB substrate (Slow TMB-ELISA (Pierce cat. # 34024)) at RT is added to each well and incubated for 15 minutes at RT. Finally, 25 μl/well of 2 N H$_2$SO$_4$ is added to each well to stop the enzymatic reaction, and the plate is read at 450 nm to 650 nm using the Molecular Devices Vmax reader.

It is preferred that the relative levels of mRNA encoding human Aβ-containing protein mRNA encoding the endogenous APP of the transgenic animal be measured in the manner described by Bordonaro et al., Biotechniques 16:428–430 (1994), and Rockenstein et al., J. Biol. Chem. 270:28257–28267 (1995). Preferred methods for measuring the expression level of Aβ$_{1-42}$, FLAPP+APPα, and APPβ are described in Example 8.

Yeast Artificial Chromosomes.

The constructs shown in FIGS. 7a and 7b can be constructed as follows. Large segments of human genomic DNA, when cloned into certain vectors, can be propagated as autonomously-replicating units in the yeast cell. Such vector-borne segments are referred to as yeast artificial chromosomes (YAC; Burke et al. Science 236:806 (1987)). A human YAC library is commercially available (Clontech, Palo Alto, Calif.) with an average insert size of 250,000 base pairs (range of 180,000 to 500,000 base pairs). A YAC clone of the Alzheimer's gene can be directly isolated by screening the library with the human APP770 cDNA. The inclusion of all of the essential gene regions in the clone can be confirmed by PCR analysis.

The YAC-APP clone, shown in FIG. 7a, can be established in embryonic stem (ES) cells by selecting for neomycin resistance encoded by the YAC vector. ES cells bearing the YAC-APP clone can be used to produce transgenic mice by established methods described below under "Transgenic Mice" and "Embryonic Stem Cell Methods". The YAC-APP gene bearing a mutation at amino acid 717 (FIG. 7b) can be produced through the generation of a YAC library using genomic DNA from a person affected by a mutation at amino acid 717. Such a clone can be identified and established in ES cells as described above.

Genetic Alteration of the Mouse APP Gene.

The nucleotide sequence homology between the human and murine Alzheimer's protein genes is approximately 85%. Within the Aβ-coding region, there are three amino acid differences between the two sequences. Amino acids Lys 670, Met671, and Val717,which can be mutated to alter APP processing, are conserved between mouse, rat, and man. Wild-type rodents do not develop Alzheimer's disease nor do they develop deposits or plaques in their central nervous system (CNS) analogous to those present in human Alzheimer's patients. Therefore, it is possible that the human but not the rodent form of Aβ is capable of causing disease. Homologous recombination (Capecchi, *Science* 244:1288–1292 (1989)) can be used to convert the mouse Alzheimer's gene in situ to a gene encoding the human Aβ by gene replacement. This recombination is directed to a site downstream from the KPI and OX-2 domains, for example, within exon 9, so that the natural alternative splicing mechanisms appropriate to all cells within the transgenic animal can be employed in expressing the final gene product.

Both wild-type (FIG. 8a) and mutant (FIG. 8b) forms of human cDNA can be used to produce transgenic models expressing either the wild-type or mutant forms of APP. The recombination vector can be constructed from a human APP cDNA (APP695, APP751, or APP770 form), either wild-type, mutant at amino acid 669, 670, 671, 690, 692, 717, or a combination of these mutations. Cleavage of the recombination vector, for example, at the XhoI site within exon 9, promotes homologous recombination within the directly adjacent sequences (Capecchi (1989)). The endogenous APP gene resulting from this event would be normal up to the point of recombination, within exon 9 in this example, and would consist of the human cDNA sequence thereafter.

Preparation of Constructs for Transfections and Microinjections.

DNA clones for microinjection are cleaved with enzymes appropriate for removing the bacterial plasmid sequences, such as SalI and NotI, and the DNA fragments electrophoresed on 1% agarose gels in TBE buffer (Sambrook et al. (1989)). The DNA bands are visualized by staining with ethidium bromide, and the band containing the APP expression sequences is excised. The excised band is then placed in dialysis bags containing 0.3 M sodium acetate, pH 7.0. DNA is electroeluted into the dialysis bags, extracted with phenol-chloroform (1:1), and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column for three times to bind DNA to the column matrix. After one wash with 3 ml of low salt buffer, the DNA is eluted with 0.4 ml of high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of DNA for microinjection are also described in Hogan et al., *Manipulating the Mouse Embryo* (Cold Spring Harbor Laboratory, Cold Spring Harbor, N.Y., 1986); in Palmiter et al., *Nature* 300:611 (1982); in *The Qiagenologist, Application Protocols,* 3rd edition, published by Qiagen, Inc., Chatsworth, Calif.; and in Sambrook et al., *Molecular Cloning: A Laboratory Manual* (Cold Spring Harbor Laboratory, Cold Spring Harbor, N.Y., 1989).

Construction of Transgenic Animals.

A. Animal Sources.

Animals suitable for transgenic experiments can be obtained from standard commercial sources such as Charles River (Wilmington, Mass.), Taconic (Germantown, N.Y.), and Harlan Sprague Dawley (Indianapolis, Ind.). Many strains are suitable, but Swiss Webster (Taconic) female mice are preferred for embryo retrieval and transfer. B6D2F$_1$ (Taconic) males can be used for mating and vasectomized Swiss Webster studs can be used to stimulate pseudopregnancy. Vasectomized mice and rats can be obtained from the supplier.

B. Microinjection Procedures.

The procedures for manipulation of the rodent embryo and for microinjection of DNA are described in detail in Hogan et al., Manipulating the Mouse Embryo (Cold Spring Harbor Laboratory, Cold Spring Harbor, N.Y., 1986), the teachings of which are incorporated herein.

C. Transgenic Mice.

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two cell stage.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

D. Transgenic Rats.

The procedure for generating transgenic rats is similar to that of mice (Hammer et al., *Cell* 63:1099–112 (1990)). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBS (Dulbecco's phosphate buffered saline) with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10 to 12 embryos are transferred into each rat oviduct through the infundibulum. The incision is then closed with sutures, and the foster mothers are housed singly.

E. Embryonic Stem (ES) Cell Methods.

1. Introduction of cDNA into ES Cells.

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and Embryonic Stem Cells, A Practical Approach,* ed. E. J. Robertson, (IRL Press 1987), the teachings of which are incorporated herein. Selection of the desired clone of transgene-containing ES cells can be accomplished through one of several means. For random gene integration, an APP clone is co-precipitated with a gene encoding neomycin resistance. Transfection is carried out by one of several methods described in detail in Lovell-Badge, in *Teratocarcinomas and Embryonic Stem Cells, A Practical Approach,* ed. E. J. Robertson, (IRL Press 1987), or in Potter et al., *Proc. Natl. Acad. Sci. USA* 81:7161 (1984). Lipofection can be performed using reagents such as provided in commercially available kits, for example DOTAP (Boehringer-Mannheim) or lipofectin (BRL). Calcium phosphate/DNA precipitation, lipofection, direct injection, and electroporation are the preferred methods. In these procedures, $0.5 \times 10^6$ ES cells are plated into tissue culture dishes and transfected with a mixture of the linearized APP clone and 1 mg of pSV2neo DNA (Southern and Berg, *J. Mol. Appl. Gen.* 1:327–341 (1982)) precipitated in the presence of 50 mg lipofectin (BRL) in a final volume of 100 μl. The cells are fed with selection medium containing 10% fetal bovine serum in DMEM supplemented with G418 (between 200 and 500 μg/ml). Colonies of cells resistant to G418 are isolated using cloning rings and expanded. DNA is extracted from drug resistant clones and Southern blots using an APP770 cDNA probe can be used to identify those clones carrying the APP sequences. PCR detection methods may also used to identify the clones of interest.

DNA molecules introduced into ES cells can also be integrated into the chromosome through the process of homologous recombination, described by Capecchi (1989). Direct injection results in a high efficiency of integration. Desired clones can be identified through PCR of DNA prepared from pools of injected ES cells. Positive cells within the pools can be identified by PCR subsequent to cell cloning (Zimmer and Gruss, *Nature* 338:150–153 (1989). DNA introduction by electroporation is less efficient and requires a selection step. Methods for positive selection of the recombination event (for example, neo resistance) and dual positive-negative selection (for example, neo resistance and gancyclovir resistance) and the subsequent identification of the desired clones by PCR have been described by Joyner et al., *Nature* 338:153–156 (1989), and Capecchi (1989), the teachings of which are incorporated herein.

2. Embryo Recovery and ES Cell Injection.

Naturally cycling or superovulated female mice mated with males can be used to harvest embryos for the implantation of ES cells. It is desirable to use the C57BL/6 strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10 to 20 ES cells are injected into blastocysts using a glass microneedle with an internal diameter of approximately 20 μm.

3. Transfer of Embryos to Pseudopregnant Females.

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

Identification, Characterization, and Utilization of Transgenic Mice and Rats.

Transgenic rodents can be identified by analyzing their DNA. For this purpose, tail samples (1 to 2 cm) can be removed from three week old animals. DNA from these or other samples can then be prepared and analyzed by Southern blot, PCR, or slot blot to detect transgenic founder ($F_0$) animals and their progeny ($F_1$ and $F_2$).

A. Pathological Studies.

The various $F_0$, $F_1$, and $F_2$ animals that carry a transgene can be analyzed by immunohistology for evidence of Aβ deposition, expression of APP or APP cleavage products, neuronal or neuritic abnormalities, and inflammatory responses in the brain. Brains of mice and rats from each transgenic line are fixed and then sectioned. Sections are stained with antibodies reactive with the APP and/or the Aβ. Secondary antibodies conjugated with fluorescein, rhodamine, horse radish peroxidase, or alkaline phosphatase are used to detect the primary antibody. These methods permit identification of amyloid plaques and other pathological lesions in specific areas of the brain. Plaques ranging in size from 9 to >50 μm characteristically occur in the brains of AD patients in the cerebral cortex, but also may be observed in deeper grey matter including the amygdaloid nucleus, corpus striatum and diencephalon. Sections can also be stained with other antibodies diagnostic of Alzheimer's plaques, recognizing antigens such as APP, Alz-50, tau, A2B5, neurofilaments, synaptophysin, MAP-2, ubiquitin, complement, neuron-specific enolase, and others that are characteristic of Alzheimer's pathology (Wolozin et al., *Science* 232:648 (1986); Hardy and Allsop, *Trends in Pharm. Sci.* 12:383–388 (1991); Selkoe, *Ann. Rev. Neurosci.* 12:463–490 (1989); Arai et al., *Proc. Natl. Acad. Sci. USA* 87:2249–2253 (1990); Majocha et al., *Amer. Assoc. Neuropathology Abs* 99:22 (1988); Masters et al., *Proc. Natl. Acad. Sci.* 82:4245–4249 (1985); Majocha et al., *Can J Biochem Cell Biol* 63:577–584 (1985)). Staining with thioflavin S and Congo Red can also be carried out to analyze the presence of amyloid and co-localization of Aβ deposits within neuritic plaques and NFTs.

B. Analysis of APP and Aβ Expression.

1. mRNA.

Messenger RNA can be isolated by the acid guanidinium thiocyanate-phenol:chloroform extraction method (Chomaczynski and Sacchi, *Anal Biochem* 162:156–159 (1987)) from cell lines and tissues of transgenic animals to determine expression levels by Northern blots, RNAse and nuclease protection assays.

2. Protein.

APP, Aβ, and other fragments of APP can and have been detected by using polyclonal and monoclonal antibodies that are specific to the APP extra-cytoplasmic domain, Aβ region, $A\beta_{1-42}$, $A\beta_{1-40}$, APPβ, FLAPP+APPα, and C-terminus of APP. A variety of antibodies that are human sequence specific, such as 10D5 and 6C6, are very useful for this purpose (Games et al. (1995)).

3. Western Blot Analysis.

Protein fractions can be isolated from tissue homogenates and cell lysates and subjected to Western blot analysis as described by, for example, Harlow et al., *Antibodies: A Laboratory Manual*, (Cold Spring Harbor, N.Y., 1988); Brown et al., *J. Neurochem.* 40:299–308 (1983); and Tate-Ostroff et al., *Proc Natl Acad Sci* 86:745–749 (1989).

Briefly, the protein fractions are denatured in Laemmli sample buffer and electrophoresed on SDS-Polyacrylamide gels. The proteins are then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of APP derived proteins.

C. Pathological and Behavioral Studies.

1. Pathological Studies.

Immunohistology and thioflavin S staining are conducted as described elsewhere herein.

In situ Hybridizations:

Radioactive or enzymatically labeled nucleic acid probes can be used to detect mRNA in situ. The probes are degraded or prepared to be approximately 100 nucleotides in length for better penetration of cells. The hybridization procedure of Chou et al., *J. Psych. Res.* 24:27–50 (1990), for fixed and paraffin embedded samples is briefly described below although similar procedures can be employed with samples sectioned as frozen material. Paraffin slides for in situ hybridization are dewaxed in xylene and rehydrated in a graded series of ethanols and finally rinsed in phosphate buffered saline (PBS). The sections are post-fixed in fresh 4% paraformaldehyde. The slides are washed with PBS twice for 5 minutes to remove paraformaldehyde. Then the sections are permeabilized by treatment with a 20 μg/ml proteinase K solution. The sections are re-fixed in 4% paraformaldehyde, and basic molecules that could give rise to background probe binding are acetylated in a 0.1 M triethanolamine, 0.3 M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

2. Behavioral Studies.

Behavioral tests designed to assess learning and memory deficits are employed. An example of such as test is the Morris water maze (Morris, *Learn Motivat.* 12:239–260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no local cues to mark the platform's location will be given to the animals. In this form, the animal must learn the platform's location relative to distal visual cues, and can be used to assess both reference and working memory. A learning deficit in the water maze has been demonstrated with PDAPP transgenic mice. An example of behavioral analysis for assessing the effect of transgenic expression of Aβ-containing proteins is described in Example 9.

Operant Behavior Studies of Memory Function:

Memory function of the disclosed transgenic animals can be assessed by testing memory-related feeding behavior (Dunnett, "Operant delayed matching and non-matching position in rats" in Behavioral Neuroscience, Volume I: A Practical Approach (Sagal, ed., IRL Press, N.Y., 1993) pages 123–136; Zornetzen, *Behav. Neur. Biol.* 36:49–60 (1982)). Transgenic and non-transgenic mice, are trained to earn food rewards in a two component operant procedure. One component features a delayed spatial alternation schedule. Under this schedule, the mouse must remember over a variable time delay which lever it has pressed in the previous trial so that it can earn a reward by pressing the alternate lever on the current trial. This provides a measure of the animal's recent or "working" memory. The second component features a discrimination spatial alternation schedule. Under this schedule, the mouse earns a reward by pressing whatever lever is illuminated. This discrimination behavior is an example of reference memory. These two groups of mice, transgenic and non-transgenic, can be chronically studied over time, for example, from 3 months of age until the end of their useful life span, in order to assess the development of sensitivity to cholinergic antagonists and behavioral impairment on these memory tasks. It is expected that the disclosed transgenic mice will model the cognitive deficits of Alzheimer's disease with enhanced sensitivity to the memory-disrupting effects of cholinergic antagonists and impairment on "working" and reference memory tasks. Dose-response challenges with the cholinergic antagonist can be conducted at various ages. These memory behavioral tests can also be used to compare the effect of compounds on the behavioral impairment of the disclosed transgenic animals. In this case, the two groups of mice are transgenic mice to which a test compound is administered and transgenic mice to which the compound is not administered.

Emotional Reactivity and Object Recognition:

Various functions of the disclosed transgenic animals can be assessed by testing locomotor activity, emotional reactivity to a novel environment or to novel objects, and object recognition. A first set of assessments are performed in the same animals at different ages (each animal is its own control) in order to test their performance in terms of locomotor activity, emotional reactivity to a novel environment or to novel objects, and object recognition, a form of memory which is severely impaired in AD patients. On the first day, transgenic and non-transgenic control mice are individually placed in a square open field with a central platform. For 30 minutes, horizontal and vertical activity, and crossings of the platform, are recorded by blocks of 5 minutes for each animal. On the second day, each animal is submitted to two trials with an intertrial of 1 hour. On the first trial, two identical objects are placed in the open field and the animal is allowed 3 minutes of exploration. On the second trial, one of the objects is replaced by a new object and the time spent by the animal in exploring the familiar and novel object is recorded during the next 3 minutes (Ennaceur and Delacour, *Behav. Brain Res.* 31:47–59 (1988)). Animals are then tested for neophobic behavior, which is considered as an index of anxiety, in a free exploration situation, in which animals are given the opportunity to move freely between a familiar and a novel environment.

Thereafter, the same animals are submitted to various learning tasks to investigate their learning and memory capacities. They are first tested for spatial recognition memory in a T-maze delayed alternation task at 6 hour and 24 hour delays. This form of memory has been shown to be very sensitive to hippocampal damage. One half of the animals of each group is then trained in a positively reinforced lever-press task as described above. This can be used to measure post training improvement in performance of the animals, which has been shown to involve hippocampal activation. The other half of the animals is trained in spatial discrimination in an 8 arm radial maze (Oltons and Samuelson, *J. Exp. Psychol.* [*Animal Behav.*] 2:97–116 (1976)) in order to evaluate working and reference memory and to analyze their strategies (angle preference), which give a better index of memory capacities. The animals trained and tested in the bar-lever press task at 2 to 3 months old can be trained and tested in radial maze at 9 to 10 months old, and vice-versa. A working memory deficit has been demonstrated in PDAPP transgenic mice in the radial arm maze.

Two additional groups can also be submitted to the same behavioral tests as above at 9 to 10 months old in order to determine whether behavioral screening performed at 2 to 3 months old influenced further learning and memory capacities.

These memory behavioral tests can also be used to compare the effect of compounds on the behavioral impairment of the disclosed transgenic animals. In this case, the two groups of mice are transgenic mice to which a test compound is administered, and transgenic mice to which the compound is not administered.

The procedures applied to test transgenic mice are similar for transgenic rats.

D. Preferred Characteristics.

The above phenotypic characteristics of the disclosed transgenic animals can be used to identify those forms of the disclosed transgenic animals that are preferred as animal models. Additional phenotypic characteristics, and assays for measuring these characteristics, that can also be used to identify those forms of the disclosed transgenic animals that are preferred as animal models, are described in Example 6. These characteristics are preferably those that are similar to phenotypic characteristics observed in Alzheimer's disease. APP and Aβ markers which are also useful for identifying those forms of the disclosed transgenic animals that are preferred as animal models are described below. Any or all of the these markers or phenotypic characteristics can be used either alone or in combination to identify preferred forms of the disclosed transgenic animals. For example, the presence of plaques in brain tissue that can be stained with Congo red is a phenotypic characteristic which can identify a disclosed transgenic animal as preferred. It is intended that the levels of expression of certain APP-related proteins present in preferred transgenic animals (discussed above) is an independent characteristic for identifying preferred transgenic animals. Thus, the most preferred transgenic animals will exhibit both a disclosed expression level for one or more of the APP-related proteins and one or more of the phenotypic characteristics discussed above. Especially preferred phenotypic characteristics (the presence of which identifies the animal as a preferred transgenic animal) are the presence of amyloid plaques that can be stained with Congo Red (Kelly (1984)), the presence of extracellular amyloid fibrils as identified by electron microscopy by 12 months of age, and the presence of type I dystrophic neurites as identified by electron microscopy by 12 months of age (composed of spherical neurites that contain synaptic proteins and APP; Dickson et al., *Am J Pathol* 132:86–101 (1988); Dickson et al., *Acta Neuropath.* 79:486–493 (1990); Masliah et al., *J Neuropathol Exp Neurol* 52:135–142 (1993); Masliah et al., *Acta Neuropathol* 87:135–142 (1994); Wang and Munoz, *J Neuropathol Exp Neurol* 54:548–556 (1995)). Examples of the detection of these characteristics is provided in Example 6. It is most preferred that the transgenic animals have amyloid plaques that can be stained with Congo Red as of 14 months of age.

Screening of Compounds for Treatment of Alzheimer's Disease.

The transgenic animals, or animal cells derived from transgenic animals, can be used to screen compounds for a potential effect in the treatment of Alzheimer's disease using standard methodology. In such AD screening assays, the compound is administered to the animals, or introduced into the culture media of cells derived from these animals, over a period of time and in various dosages, then the animals or animal cells are examined for alterations in APP expression or processing, expression levels or localization of other AD markers, histopathology, and/or, in the case of animals, behavior using the procedures described above and in the examples below. In general, any improvement in behavioral tests, alteration in AD-associated markers, reduction in the severity of AD-related histopathology, reduction in the expression of Aβ or APP cleavage products, and/or changes in the presence, absence or levels of other compounds that are correlated with AD which are observed in treated animals, relative to untreated animals, is indicative of a compound useful for treating Alzheimer's disease. The specific proteins, and the encoding transcripts, the enzymatic or biochemical activity, and/or histopathology of those proteins, that are associated with and characteristic of AD are referred to herein as markers. Expression or localization of these markers characteristic of AD has either been detected, or is expected to be present, in the disclosed transgenic animals. These markers can be measured or detected, and those measurements compared between treated and untreated transgenic animals to determine the effect of a tested compound.

Markers useful for AD screening assays are selected based on detectable changes in these markers that are associated with AD. Many such markers have been identified in AD and have either been detected in the disclosed transgenic animals or are expected to be present in these animals. These markers fall into several categories based on their nature, location, or function. Preferred examples of markers useful in AD screening assays are described below, group as Aβ-related markers, plaque-related markers, cytoskeletal and neuritic markers, inflammatory markers, and neuronal and neurotransmitter-related markers.

A. Aβ-related Markers.

Expression of the various forms of APP and Aβ can be directly measured and compared in treated and untreated transgenic animals both by immunohistochemistry and by quantitative ELISA measurements as described above and in the examples. Currently, it is known that two forms of APP products are found, APP and Aβ (Haass and Selkoe, *Cell* 75:1039–1042 (1993)). They have been shown to be intrinsically associated with the pathology of AD in a time dependent manner. Therefore, preferred assays compare age-related changes in APP and Aβ expression in the transgenic mice. As described in Example 6, increases in Aβ have been demonstrated during aging of the PDAPP mouse.

Preferred targets for assay measurement are Aβ markers known to increase in individuals with Alzheimer's disease are total Aβ ($A\beta_{tot}$) Aβ 1–42 ($A\beta_{1-42}$; Aβ with amino acids 1–42), $A\beta_{1-40}$ (Aβ with amino acids 1–40), Aβ N3(pE) ($A\beta_{N3}(pE)$); $A\beta_{X-42}$ ($A\beta_{X-42}$; Aβ forms ending at amino acid 42); Aβ X-40 ($A\beta_{X-40}$; Aβ forms ending at amino acid 40); insoluble Aβ ($A\beta_{Isoluble}$); and soluble Aβ ($A\beta_{Soluble}$; Kuo et al., *J. Biol. Chem.* 271(8):4077–4081 (1996)). $A\beta_{N3}(pE)$ has pyroglutamic acid at position 3 (Saido, *Neuron* 14:457–466 (1995)). $A\beta_{X-42}$ refers to any of the C-terminal forms of Aβ such as $A\beta_{13-42}$. $A\beta_{Insoluble}$ refers to forms of Aβ that are recovered as described in Gravina, *J. Biol. Chem.* 270:7013–7016 (1995). APPβ can also be specifically measured to assess the amount of β-secretase activity (Seubert et al., *Nature* 361:260–263 (1993)). Several of these Aβ forms and their association with Alzheimer's disease are described by Haass and Selkoe (1993). Detection and measurement of $A\beta_{tot}$, $A\beta_{1-42}$, and $A\beta_{X-42}$ are described in Example 6. Generally, specific forms of Aβ can be assayed, either quantitatively or qualitatively using specific antibodies, as described below. When referring to amino acid positions in forms of Aβ, the positions correspond to the Aβ region of APP. Amino acid 1 of Aβ corresponds to amino acid 672 of APP, and amino acid 42 of Aβ corresponds to amino acid 714 of APP.

Also preferred as targets for assay measurement are APP markers. For example, different forms of secreted APP (termed APPα and APPβ) can also be measured (Seubert et al., *Nature* 361:260–263 (1993)). Other APP forms can also serve as targets for assays to assess the potential for compounds to affect Alzheimer's disease. These include FLAPP+APPα, full length APP, C-terminal fragments of APP, especially C100 (the last 100 amino acids of APP) and C57 to C60 (the last 57 to 60 amino acids of APP), and any forms of APP that include the region corresponding to $A\beta_{1-40}$.

APP forms are also preferred targets for assays to assess the potential for compounds to affect Alzheimer's disease. The absolute level of APP and APP transcripts, the relative levels of the different APP forms and their cleavage products, and localization of APP expression or processing are all markers associated with Alzheimer's disease that can be used to measure the effect of treatment with potential therapeutic compounds. The localization of APP to plaques and neuritic tissue is an especially preferred target for these assays.

Quantitative measurement can be accomplished using many standard assays. For example, transcript levels can be measured using RT-PCR and hybridization methods including RNase protection, Northern analysis, and R-dot analysis. APP and Aβ levels can be assayed by ELISA, Western analysis, and by comparison of immunohistochemically stained tissue sections. Immunohistochemical staining can also be used to assay localization of APP and Aβ to particular tissues and cell types. Such assays were described above and specific examples are provided below.

B. Plaque-related Markers.

A variety of other molecules are also present in plaques of individuals with AD and in the disclosed transgenic animals, and their presence in plaques and neuritic tissue can be detected. The amount of these markers present in plaques or neuritic tissue is expected to increase with the age of untreated transgenic animals. Preferred plaque-related markers are apolipoprotein E, glycosylation end products, amyloid P component, advanced glycosylation end products (Smith et al., *Proc. Natl. Acad. Sci. USA* 91:5710 (1994)), growth inhibitory factor, laminin, collagen type IV (Kalaria and Perry (1993); Ueda et al. (1993)), receptor for advanced glycosylation products (RAGE), and ubiquitin.

While the above markers can be used to detect specific components of plaques and neuritic tissue, the location and extent of plaques can also be determined by using well known histochemical stains, such as Congo Red and thioflavin S, as described above and in some examples below.

C. Cytoskeletal and Neuritic Markers.

Many changes in cytoskeletal markers associated with AD have also been detected in transgenic PDAPP mice. These markers can be used in AD screening assays to determine the effect of compounds on AD. Many of the changes in cytoskeletal markers occur either in the neurofibrillary tangles or dystrophic neurites associated with plaques (Kosik et al. (1992); Lovestone and Anderton (1992); Brandan and Inestrosa (1993); Trojanowski et al. (1993); Masliah et al. (1993)).

The following are preferred cytoskeletal and neuritic markers that exhibit changes in and/or an association with AD. These markers can be detected, and changes can be determined, to measure the effect of compounds on the disclosed transgenic animals. Spectrin exhibits increased breakdown in AD. Tau and neurofilaments display an increase in hyperphosphorylation in AD, and levels of ubiquitin increase in AD. Tau, ubiquitin, MAP-2, neurofilaments, heparin sulfate, and chrondroitin sulphate are localized to plaques and neuritic tissue in AD and in general change from the normal localization. GAP43 levels are decreased in the hippocampus and abnormally phosphorylated tau and neurofilaments are present in PDAPP transgenic mice.

D. Inflammatory Markers.

Alzheimer's disease is also known to stimulate an immunoinflammatory response, with a corresponding increase in inflammatory markers (Frederickson and Brunden (1994); McGeer et al. (1991); Wood et al. (1993)). The following are preferred inflammatory markers that exhibit changes in and/or an association with AD. Detection of changes in these markers are useful in AD screening assays. Acute phase proteins and glial markers, such as α1-antitrypsin, C-reactive protein, α2-macroglobulin (Tooyama et al., *Molecular & Chemical Neuropathology* 18:153–60 (1993)), glial fibrillary acidic protein (GFAP), Mac-1, F4/80, and cytokines, such as IL-1α and β, TNFα, IL-8, MIP-1α (Kim et al., *J. Neuroimmunology* 56:127–134 (1995)), MCP-1 (Kim et al., *J. Neurological Sciences* 128:28–35 (1995); Kim et al., *J. Neuroimmunology* 56:127–134 (1995); Wang et al., *Stroke* 26:661–665 (1995)), and IL-6, all increase in AD and are expected to increase in the disclosed transgenic animals. Complement markers, such as C3d, C1q, C5, C4d, C4bp, and C5a-C9, are localized in plaques and neuritic tissue. Major histocompatibility complex (MHC) glycoproteins, such as HLA-DR and HLA-A, D,C increase in AD. Microglial markers, such as CR3 receptor, MHC I, MHC II, CD 31, CD11a, CD11b, CD11c, CD68, CD45RO, CD45RD, CD18, CD59, CR4, CD45, CD64, and CD44 (Akiyama et al., *Brain Research* 632:249–259 (1993)) increase in AD. Additional inflammatory markers useful in AD screening assays include α2 macroglobulin receptor, Fibroblast growth factor (Tooyama et al., *Neuroscience Letters* 121:155–158 (1991)), ICAM-1 (Akiyama et al., *Acta Neuropathologica* 85:628–634 (1993)), Lactotransferrin (Kawamata et al., *American Journal of Pathology* 142:1574–85 (1993)), C1q, C3d, C4d, C5b–9, Fc gamma RI, Fc gamma RII, CD8 (McGeer et al., *Can J Neurol Sci* 16:516–527 (1989)), LCA (CD45) (McGeer et al. (1989); Akiyama et al., *Journal of Neuroimmunology* 50:195–201

(1994)), CD18 (beta-2 integrin) (Akiyama and McGeer, *Journal of Neuroimmunology* 30:81–93 (1990)), CD59 (McGeer et al., *Brain Research* 544:315–319 (1991)), Vitronectic (McGeer et al., *Canadian Journal of Neurological Sciences* 18:376–379 (1991); Akiyama et al., *Journal of Neuroimmunology* 32:19–28 (1991)), Vitronectin receptor, Beta-3 integrin (Akiyama et al. (1991)), Apo J, clusterin (McGeer et al., *Brain Research* 579:337–341 (1992)), type 2 plasminogen activator inhibitor (Akiyama et al., *Neuroscience Letters* 164:233–235 (1993)), CD44 (Akiyama et al., *Brain Research* 632:249–259 (1993)), Midkine (Yasuhara et al., *Biochemical & Biophysical Research Communications* 192:246–251 (1993)), Macrophage colony stimulating factor receptor (Akiyama et al., *Brain Research* 639:171–174 (1994)), MRP14, 27E10, and interferon-alpha (Akiyama et al., *Journal of Neuroimmunology* 50:195–201 (1994)). Additional markers which are associated with inflammation or oxidative stress include 4-hydroxynonenal-protein conjugates (Uchida et al., *Biochem. Biophys. Res. Comm.* 212:1068–1073 (1995); Uchida and Stadtman, *Methods in Enzymology* 233:371–380 (1994); Yoritaka et al., *Proc. Natl. Acad. Sci. USA* 93:2696–2701 (1996)), IκB, NFκB (Kaltschmidt et al., *Molecular Aspects of Medicine* 14:171–190 (1993)), cPLA$_2$ (Stephenson et al., *Neurobiology Dis.* 3:51–63 (1996)), COX-2 (Chen et al., *Neuroreport* 6:245–248 (1995)), Matrix metalloproteinases (Backstrom et al., *J. Neurochemistry* 58:983–992 (1992); Bignami et al., *Acta Neuropathologica* 87:308–312 (1994); Deb and Gottschall, *J. Neurochemistry* 66:1641–1647 (1995); Peress et al., *J. Neuropathology & Experimental Neurology* 54:16–22 (1995)), Membrane lipid peroxidation, Protein oxidation (Hensley et al., *J. Neurochemistry* 65:2146–2156 (1995); Smith et al., *Proc. Natl. Acad. Sci. USA* 88:10540–10543 (1991)), and diminished ATPase activity (Mark et al., *J. Neuroscience* 15:6239 (1995)). These markers can be detected, and changes can be determined, to measure the effect of compounds on the disclosed transgenic animals.

E. Neuronal and Neurotransmitter-related Markers.

Changes in neuronal and neurotransmitter biochemistry have been associated with AD and in the disclosed PDAPP animals. In AD there is a profound reduction in cortical and hippocampal cholinergic innervation. This is evidenced by the dramatic loss of the synthetic enzyme choline acetyltransferase and decreased acetylcholinersterase, synaptosomal choline uptake (as measured by hemicholinium binding) and synthesis and release of acetylcholine (Rylett et al. (1983); Sims et al. (1980); Coyle et al., *Science* 219:1184–1190 (1983); Davies and Maloney, *Lancet* 2:1403 (1976); Perry et al., *Lancet* 1:189 (1977); Sims et al., *J. Neurochem.* 40: 503–509 (1983)) all of which are useful markers. These markers can be used in AD screening assays to determine the effect of compounds on AD. There is also a loss of basal forebrain neurons and the galanin system becomes hypertrophic in AD.

In addition to changes in the markers described above in AD, there is also atrophy and loss of basal forebrain cholinergic neurons that project to the cortex and hippocampus (Whitehouse et al., *Science* 215:1237–1239 (1982)), as well as alterations of entorhinal cortex neurons (Van Hoesan et al., *Hippocampus* 1:1–8 (1991). Based upon these observations measurement of these enzyme activities, neuronal size, and neuronal count numbers are expected to decrease in the disclosed transgenic animals and are therefore useful targets for detection in AD screening assays. Basal forebrain neurons are dependent on nerve growth factor (NGF). Brain-derived neurotrophic factor (BDNF) may also decrease in the hippocampus in the disclosed transgenic animals and is therefore a useful target for detection in AD screening assays.

It has also been shown that APP and Aβ release are affected by stimulation of muscarinic receptors both in vitro in tissue culture as well as in brain slices. Similar findings have also been obtained with application of other agonists linked to phosphoinosital turnover (Nitsch et al. (1992); Hung et al., *J. Biol. Chem.* 268:22959–22962 (1993); Nitsch et al., *Proceedings of the Eighth Meeting of the International Study Group on the Pharmacology of Memory Disorders Associated with Aging* 497–503 (1995); Masliah and Terry (1993); Greenamyre and Maragos (1993); McDonald and Nemeroff (1991); Mohr et al. (1994); Perry, *British Medical Bulletin* 42:63–69 (1986); Masliah et al., *Brian Research* 574:312–316 (1992); Schwagerl et al., *Journal of Neurochemistry* 64:443–446 (1995)). Based upon these observations, it is possible that neurotransmitter agonists will reduce the production of Aβ in the disclosed transgenic animals. Based on this reasoning, screening assays that measure the effect of compounds on neurotransmitter receptors can possibly be used to identifying compounds useful in treating AD.

In addition to the well-documented changes in the cholinergic system, dysfunction in other receptor systems such as the serotinergic, adrenergic, adenosine, and nicotine receptor systems, has also been documented. Markers characteristic of these changes, as well as other neuronal markers that exhibit both metabolic and structural changes in AD are listed below. Changes in the level and/or localization of these markers can be measured using similar techniques as those described for measuring and detecting the earlier markers.

The following are preferred cytoskeletal and neuritic markers that exhibit changes in and/or an association with AD. Levels of cathepsin (cat) D,B and Neuronal Thread Protein, and phosphorylation of elongation factor-2, increase in AD. Cat D,B, protein kinase C, and NADPH are localized in plaque and neuritic tissue in AD. Activity and/or levels of nicotine receptors, 5-HT$_2$ receptor, NMDA receptor, α2-adrenergic receptor, synaptophysin, p65, glutamine synthetase, glucose transporter, PPI kinase, drebrin, GAP43, cytochrome oxidase, heme oxygenase, calbindin, adenosine A1 receptors, mono amine metabolites, choline acetyltransferase, acetylcholinesterase, and symptosomal choline uptake are all reduced in AD.

Additional markers that are associated with AD or after treatment of cells with Aβ include (1) cPLA$_2$ (Stephenson et al., *Neurobiology of Diseases* 3:51–63 (1996)), which is upregulated in AD, (2) Heme oxygenase-1 (Premkumar et al., *J. Neurochemistry* 65:1399–1402 (1995); Schipper et al., *Annals of Neurology* 37:758–768 (1995); Smith et al., *American Journal of Pathology* 145:42–47 (1994); Smith et al., *Molecular & Chemical Neuropathology* 24:227–230 (1995)), c-jun (Anderson et al., *Experimental Neurology* 125:286–295 (1994); Anderson et al., *J. Neurochemistry* 65:1487–1498 (1995)), c-fos (Anderson et al. (1994); Zhang et al., *Neuroscience* 46:9–21 (1992)), HSP27 (Renkawek et al., *Acta Neuropathologica* 87:511–519 (1994); Renkawek et al., *Neuroreport* 5:14–16 (1993)), HSP70 (Cisse et al., *Acta Neuropathologica* 85:233–240 (1993)), and MAP5 (Geddes et al., *J. Neuroscience Research* 30:183–191 (1991); Takahashi et al., *Acta Neuropathologica* 81:626–631 (1991)), which are induced in AD and in cortical cells after Aβ treatment, and (3) junb, jund, fosB, fra1 (Estus et al., *J. Cell Biology* 127:1717–1727 (1994)), cyclin D1 (Freeman et al., Neuron 12:343–355 (1994); Kranenburg et al., *EMBO*

*Journal* 15:46–54 (1996)), p53 (Chopp, *Current Opinion in Neurology & Neurosurgery* 6:6–10 (1993); Sakhi et al., *Proc. Natl. Acad. Sci. USA* 91:7525–7529 (1994); Wood and Youle, *J. Neuroscience* 15:5851–5857 (1995)), NGFI-A (Vaccarino et al., *Molecular Brain Research* 12:233–241 (1992)), and NGFI-B, which are induced in cortical cells after Aβ treatment.

F. Measuring the Amounts and Localization of AD Markers.

Quantitative measurement can be accomplished using many standard assays. For example, transcript levels can be measured using RT-PCR and hybridization methods including RNase protection, Northern analysis, and R-dot analysis. Protein marker levels can be assayed by ELISA, Western analysis, and by comparison of immunohistochemically stained tissue sections. Immunohistochemical staining can also be used to assay localization of protein markers to particular tissues and cell types. The localization and the histopathological association of AD markers can be determined by histochemical detection methods such as antibody staining, laser scanning confocal imaging, and immunoelectron micrography. Examples of such techniques are described in Masliah et al. (1993) and in Example 6 below.

In the case of receptors and enzymatic markers, activity of the receptors or enzymes can be measured. For example, the activity of neurotransmitter metabolizing enzymes such as choline acetyltransferase and acetylcholine esterase can be measured using standard radiometric enzyme activity assays.

The activity of certain neurotransmitter receptors can be determined by measuring phosphoinositol (PI) turnover. This involves measuring the accumulation of inositol after stimulation of the receptor with an agonist. Useful agonists include carbachol for cholinergic receptors and norepinephrine for glutaminergic receptors. The number of receptors present in brain tissue can be assessed by quantitatively measuring ligand binding to the receptors.

The levels and turnover of receptor ligands and neurotransmitters can be determined by quantitative assays taken at various time points. Dopamine turnover can be measured using DOPAC and HVA. MOPEG sulfate can be used to measure norepinephrine turnover and 5-HIAA can be used to measure serotonin turnover. For example, norepinephrine levels have been shown to be reduced 20% in the hippocampus of 12 to 13 month old PDAPP transgenic mice relative to controls. Generally, the above assays can be performed as described in the literature, for example, in Rylett et al. (1983); Sims et al. (1980); Coyle et al., *Science* 219:1184–1190 (1983); Davies and Maloney, *Lancet* 2:1403 (1976); Perry et al., *Lancet* 1:189 (1977); Sims et al., *J. Neurochem.* 40: 503–509 (1983). These markers are also described by Bymaster et al., *J. Pharm. Exp. Ther.* 269:282–289 (1994).

G. Screening Assays Using Cultured Cells.

Screening assays for determining the therapeutic potential of compounds can also be performed using cells derived from animals transgenic for the disclosed APP constructs and cell cultures stably transfected with the disclosed constructs. For example, such assays can be performed on cultured cells in the following manner. Cell cultures can be transfected generally in the manner described in International Patent Application No. 94/10569 and Citron et al. (1995). Derived transgenic cells or transfected cell cultures can then be plated in Corning 96-well plates at 1.5 to $2.5\times10^4$ cells per well in Dulbecco's minimal essential media plus 10% fetal bovine serum.

Following overnight incubation at 37° C. in an incubator equilibrated with 10% carbon dioxide, media are removed and replaced with media containing a compound to be tested for a two hour pretreatment period and cells were incubated as above. Stocks containing the compound to be tested are first prepared in 100% dimethylsulfoxide such that at the final concentration of compound used in the treatment, the concentration of dimethylsulfoxide does not exceed 0.5%, preferably about 0.1%.

At the end of the pretreatment period, the media are again removed and replaced with fresh media containing the compound to be tested as above and cells are incubated for an additional 2 to 16 hours. After treatment, plates are centrifuged in a Beckman GPR at 1200 rpm for five minutes at room temperature to pellet cellular debris from the conditioned media. From each well, 100 μL of conditioned media or appropriate dilutions thereof are transferred into an ELISA plate precoated with antibody 266 (an antibody directed against amino acids 13 to 28 of Aβ) as described in International Patent Application No. 94/10569 and stored at 4° C. overnight. An ELISA assay employing labelled antibody 6C6 (against amino acids 1 to 16 of Aβ) can be run to measure the amount of Aβ produced. Different capture and detection antibodies can also be used.

Cytotoxic effects of the compounds are measured by a modification of the method of Hansen et al., *J. Immun. Method.* 119:203–210 (1989). To the cells remaining in the tissue culture plate, 25 μL of a 3,(4,5-dimethylthiazol-2-yl) 2,5-diphenyltetrazolium bromide (MTT) stock solution (5 mg/mL) is added to a final concentration of 1 mg/mL. Cells are incubated at 37° C. for one hour, and cellular activity is stopped by the addition of an equal volume of MTT lysis buffer (20% w/v sodium dodecylsulfate in 50% dimethylformamide, pH 4.7). Complete extraction is achieved by overnight shaking at room temperature. The difference in the $OD_{562nm}$ and the $OD_{650nm}$ is measured in a Molecular Device's $UV_{max}$ microplate reader, or equivalent, as an indicator of the cellular viability.

The results of the Aβ ELISA are fit to a standard curve and expressed as ng/mL Aβ. In order to normalize for cytotoxicity, these results are divided by the MTT results and expressed as a percentage of the results from a control assay run without the compound.

All publications cited herein are hereby incorporated by reference.

EXAMPLE 1

Expression of pMTAPP-1 in NIH3T3 and PC12 Cells.

The clone pMTAPP-1 is an example of an APP770 expression construct as shown in FIG. 1a where the promoter used is the metallothionine promoter. Stable cell lines were derived by transfecting NIH3T3 and PC12 cell lines (ATCC #CCL92 and CRL1721). Five hundred thousand NIH3T3 or PC12 cells were plated into 100 mm dishes and transfected with a mixture of 5 mg of the SalI fragment and 1 mg of pSV2neo DNA (Southern and Berg (1982)) precipitated in the presence of 50 mg lipofectin (Gibco, BRL) in a final volume of 100 μl. Polylysine-coated plates were used for PC12 cells, which normally do not adhere well to tissue culture dishes. The cells were fed with selection medium containing 10% fetal bovine serum in DMEM or RPMI and supplemented with G418. Five hundred mg/ml (biological weight) and 250 mg/ml of G418 were used to select colonies form NIH3T3 and PC12 cells, respectively. Fifteen days after transfection, colonies of cells resistant to G418 were isolated by cloning rings and expanded in T flasks. The presence of APP cDNA in the cells was detected by PCR using the procedure of Mullis and Faloona, *Methods Enzymol.* 155:335–350 (1987), the teachings of which are incorporated herein.

Expression of APP in 25 colonies from each cell line was analyzed by immunostaining (Majocha et al. (1988)). Cells were grown to subconfluence and fixed in a solution containing 4% paraformaldehyde, 0.12 M NaCl, and 20 mm $Na_3PO_4$, pH 7.0. They were incubated overnight with a primary monoclonal antibody against a synthetic Aβ sequence (Masters et al. (1985); Glenner and Wong) provided by Dr. Ronald Majocha, Massachusetts General Hospital, Boston, Mass., followed by a generalized anti-mouse antibody conjugated to biotin (Jackson ImmunoResearch Labs, PA). Immunostaining was then performed by adding avidin-horseradish peroxidase (HRP) (Vector Labs, Burlingame, Calif.) and diaminobenzidine as the chromogen (Majocha et al. (1985)). The results indicated that the pMTAPP-1 vector was expressing APP in both NIH3T3 and PC12 cells.

EXAMPLE 2

Expression of pEAPP-1 in PC12 Cells.

pEAPP-1 is an example of an APP770 expression construct as shown in FIG. 1a where the promoter used is the 25 kb human APP gene promoter. DNA from this construct was transfected into PC12 cells as described above. Certain clones of pEAPP-1 transfected cells exhibited a differentiation phenotype morphologically similar to that exhibited by PC12 cells treated with nerve growth factor (NGF). PC12 cells normally are fairly round and flat cells. Those transfected with pEAPP-1 have cytoplasmic extensions resembling neurites. PC12 cells treated with NGF extend very long neuritic extensions. Thirteen PC12 cell clones transfected with pEAPP-1 were selected and propagated. Eight of these cell clones exhibited the spontaneous differentiation phenotype with clones 1–8, 1–1, and 1–4 exhibiting the strongest phenotypes. Staining of pEAPP-1 transfected PC12 cells with antibody against the Aβ as described in Example 1 indicated that those cells exhibiting the differentiation were also expressing APP. Because PC12 cells transfected with the pMTAPP-1 clone did not exhibit this phenotype even though the APP770 cDNA is expressed, these results suggest that expression of APP770 from the human promoter has novel properties regarding the physiology of the cell.

EXAMPLE 3

Expression of pMTA-4 in PC12 Cells.

pMTA4 is an example of the type of construct shown in FIG. 4a where the promoter used is the metallothionine promoter. The protein encoded by this construct differs slightly from that depicted in FIG. 4a. An APP770 cDNA clone was digested with Asp718 which cleaves after position 57 (number system of Kang et al. (1987)). The resulting 5' extension was filled in using the Klenow enzyme (Sambrook et al. (1989)). The same DNA preparation was also cleaved with EcoRI which also cuts after position 2020 and the resulting 5' extension was filled in using the Klenow enzyme (Sambrook et al. (1989)). Self-ligation of this molecule results in an expression clone in which the truncated protein thus encoded contains the leader sequence, followed by a shortened version of the Aβ starting with the sequence Phe-Arg-Val-Gly-Ser-of the Aβ followed by the 56 terminal amino acids of APP. DNA from this construct was transfected into PC12 cells as described above.

EXAMPLE 4

Generation of Transgenic Mice expressing APP under the control of MT-1 promoter.

Transgenic mice were made by microinjecting pMTAPP-1 vector DNA into pronuclear embryos. pMTAPP-1 is an example of the type of construct shown in FIG. 1a in which the APP770 coding sequence is operably linked to the metallothionine promoter. The procedures for microinjection into mouse embryos are described in *Manipulating the Mouse Embryo* by Hogan et al. (1986). Only a brief description of the procedures is described below.

Mice were obtained from Taconic Laboratories (German Town, N.Y.). Swiss Webster female mice were used for embryo retrieval and implantation. $B6D2F_1$ males were used for mating and vasectomized Swiss webster studs were used to simulate pseudopregnancy.

A. Embryo Recovery.

Female mice, 4 to 8 weeks of age, were induced to superovulate with 5 IU of pregnant mare's serum gonadotropin (PMSG; Sigma) followed 48 hours later by 5 IU of human chorionic gonadotropin (hCG; Sigma). Females were placed with males immediately after hCG injection. Embryos were recovered from excised oviducts of mated females 21 hours after hCG in Dulbecco's phosphate buffered saline with 0.5% bovine serum albumin (BSA; Sigma). Surrounding cumulus cells were removed with hyaluronidase (1 mg/ml). Pronuclear embryos were then washed and placed in Earle's balanced salt solution containing 0.4% BSA (EBSS) in a 37.5° C. incubator with a humidified atmosphere at 7% $CO_2$, 5% $O_2$, and 88% $N_2$ until the time of injection.

B. Microinjection.

Elutip-D™ purified SalI DNA was dissolved in 5 mM Tris (pH 7.4) and 0.1 mM EDTA at 3 μg/ml concentration for microinjection. Microneedles and holding pipettes were pulled from Fisher coagulation tubes (Fisher) on a DKI model 720 pipette puller. Holding pipettes were then broken at approximately 70 μm (O.D.) and fire polished to an I.D. of about 30 μm on a Narishige microforge (model MF-83). Pipettes were mounted on Narishige micromanipulators which were attached to a Nikon Diaphot microscope. The air-filled injection pipette was filled with DNA solution through the tip after breaking the tip against the holding pipette. Embryos, in groups of 30 to 40, were placed in 100 μk drops of EBBS under paraffin oil for micromanipulation. An embryo was oriented and held with the holding pipette. The injection pipette was then inserted into the male pronucleus (usually the larger one). If the pipette did not break through the membrane immediately the stage was tapped to assist in penetration. The nucleus was then injected and the injection was monitored by swelling of the nucleus. Following injection, the group of embryos was placed in EBSS until transfer to recipient females.

C. Transfer.

Randomly cycling adult female mice were paired with vasectomized Swiss Webster males. Recipient females were mated at the same time as donor females. At the time of transfer, the females were anesthetized with avertin. The oviducts were exposed by a single midline dorsal incision. An incision was then made through the body wall directly over the oviduct. The ovarian bursa was then torn with watch makers forceps. Embryos to be transferred were placed in DPBS and in the tip of a transfer pipet (about 10 to 12 embryos). The pipet tip was inserted into the infundibulum and embryos were transferred. After the transfer, the incision was closed by two sutures.

D. Analysis of Mice for Transgene Integration.

At three weeks of age or older, tail samples about 1 cm long were excised for DNA analysis. The tail samples were digested by incubating with shaking overnight at 55° C. in the presence of 0.7 ml 5 mM Tris, pH 8.0, 100 mM EDTA, 0.5% SDS and 350 μg of proteinase K. The digested material was extracted once with an equal volume of phenol and once with an equal volume of phenol:chloroform (1:1 mixture). The supernatants were mixed with 70 μl 3 M sodium acetate (pH 6.0) and the DNA was precipitated by adding equal volume of 100% ethanol. The DNA was spun down in a microfuge, washed once with 70% ethanol, dried and dissolved in 100 μl TE buffer (10 mM Tris pH 8.0 and 1 mM EDTA).

Ten to twenty microliters of DNA from each sample was digested with BamHI, electrophoresed on 1% agarose gels, blotted onto nitrocellulose paper, and hybridized with $^{32}$P-labeled APP cDNA fragment. Transgenic animals were identified by autoradiography of the hybridized nitrocellulose filters. The DNAs were also analyzed by PCR carried out by synthetic primers to generate an 800 bp fragment of APP DNA.

A total of 671 pronuclear embryos were microinjected out of which 73 live and 6 dead pups were born. DNA analysis identified 9 transgenic mice (5 females and 4 males) which were bred to generate $F_1$ and $F_2$ transgenics. These animals can be analyzed for expression of mRNA and protein of APP in different tissues and for analysis of behavioral and pathological abnormalities as described above. Transgenic mice with this construct express transgenic RNA.

EXAMPLE 5

Construction of APP construct containing a combination cDNA/genomoc coding sequence.

A cDNA/genomic APP construct containing introns 6, 7 and 8 was prepared by combining APP cDNA encoding exons 1–6 and 9–18 with genomic APP sequences encoding introns 6, 7 and 8, and exons 7 and 8 (see FIGS. 6a and 6b). In order to create a splicing cassette small enough for convenient insertion in a pUC vector, two deletions in intronic sequences were made. A deletion was made in intron 6 from position 143 of intron 6 to the BamHI site located upstream of the beginning of exon 7 (1658 bp before the beginning of exon 7). Another deletion was made in intron 8 from the first BamHI site in intron 8 to a site at 263 bp before the beginning of exon 9. To avoid confusion, these truncated forms of APP introns 6 and 8 are referred to herein as intron Δ6 and intron Δ8. BamHI sites were engineered at the sites of these deletions, so that they are marked by the presence of BamHI sites. In this construct, referred to as PDAPP, exons 7 and 8 and intron 7 are intact genomic sequences, except that the unique XhoI site in intron 7 was destroyed.

DNA fragments containing the truncated introns were generated as follows: a BamHI site was engineered 143 bp into intron 6 nucleotide by PCR mutagenesis ("Mutagenesis by PCR" in *PCR Technology: Current Innovations* (Griffith and Griffith, eds., CRC Press, 1994) pages 69–83) and another BamHI site was engineered by PCR mutagenesis 263 bp prior to the beginning of exon 9. These sites were engineered into separate APP genomic DNA clones containing the junctions of exon 6 and intron 6, and intron 8 and exon 9, respectively, resulting in modified APP genomic DNA clones.

Figure 11:
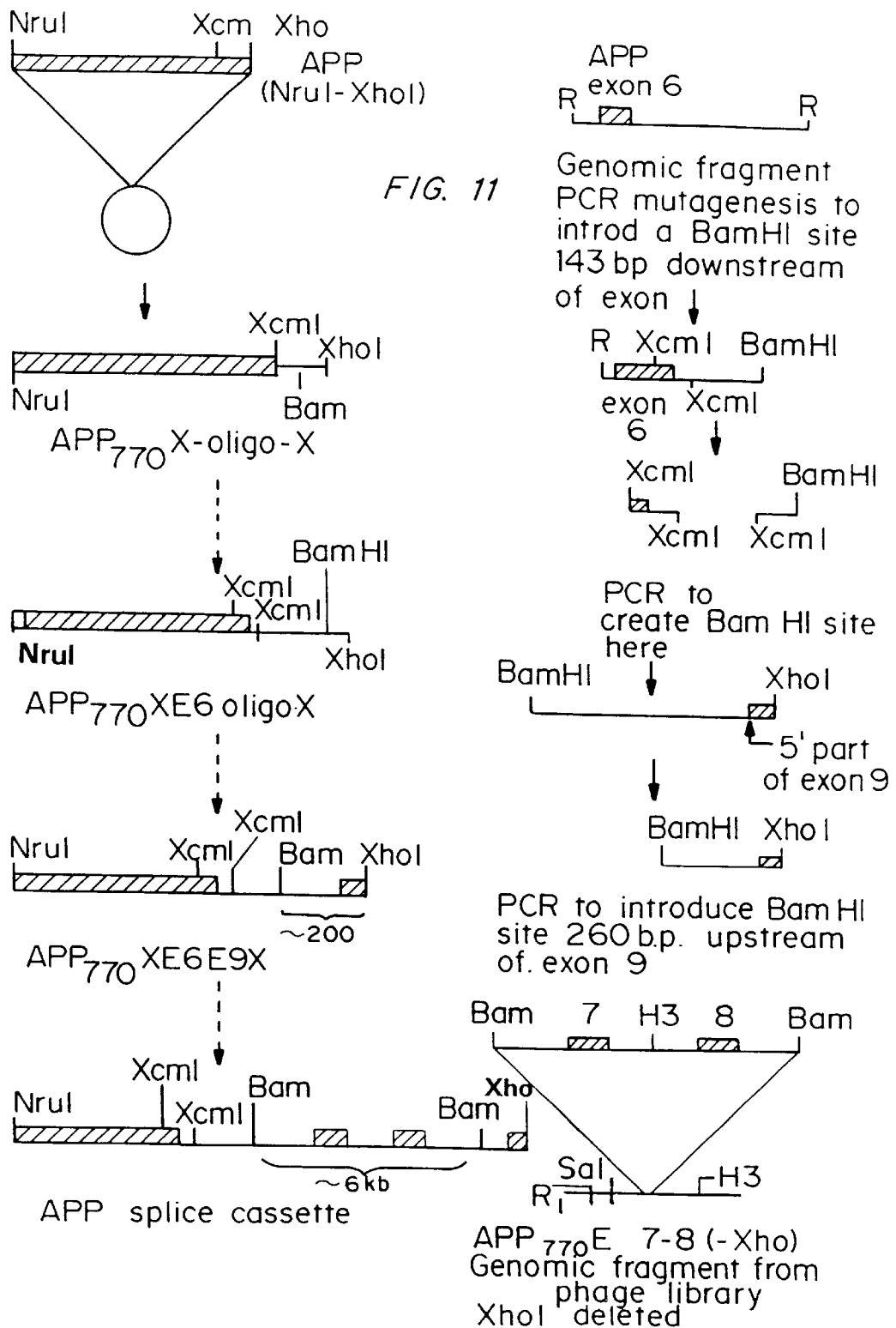
FIG. 11 is a diagram of the intermediate constructs used to construct the APP splicing cassette and the PDAPP vector.

The entire cassette was assembled in the APP cDNA clone as follows (FIG. 11). The 889 bp BamHI to XcmI fragment of APP cDNA containing exons 1 through 5 and part of exon 6 (including nucleotides 1 to 843 of SEQ ID NO:5) was cloned into a vector containing BamHI and XhoI sites downstream from the insertion site to make APP770x-oligo-x. APP770x-oligo-x was then cut with XcmI and BamHI. Then two fragments were obtained from the modified APP genomic DNA clone containing the junction of exon 6 and intron 6 described above by cutting with XcmI and BamHI. The resulting 34 bp fragment from the XcmI in exon 6 to the XcmI in intron 6, and 131 bp fragment from the XcmI in intron 6 to the artificially created BamHI site at position 143 bp of intron 6 were ligated into APP770x-oligo-x in a three-way ligation step to make APP770x-E6oligo-x. The orientation of the fragments was confirmed by sequencing. APP770x-E6oligo-x was then cut with BamHI and XhoI. Then the 313 bp BamHI and XhoI fragment from the modified APP genomic DNA clone containing the junction of intron 8 and exon 9 was ligated into APP770x-E6oligo-x to make APP770xE6E9x.

Figure 10:
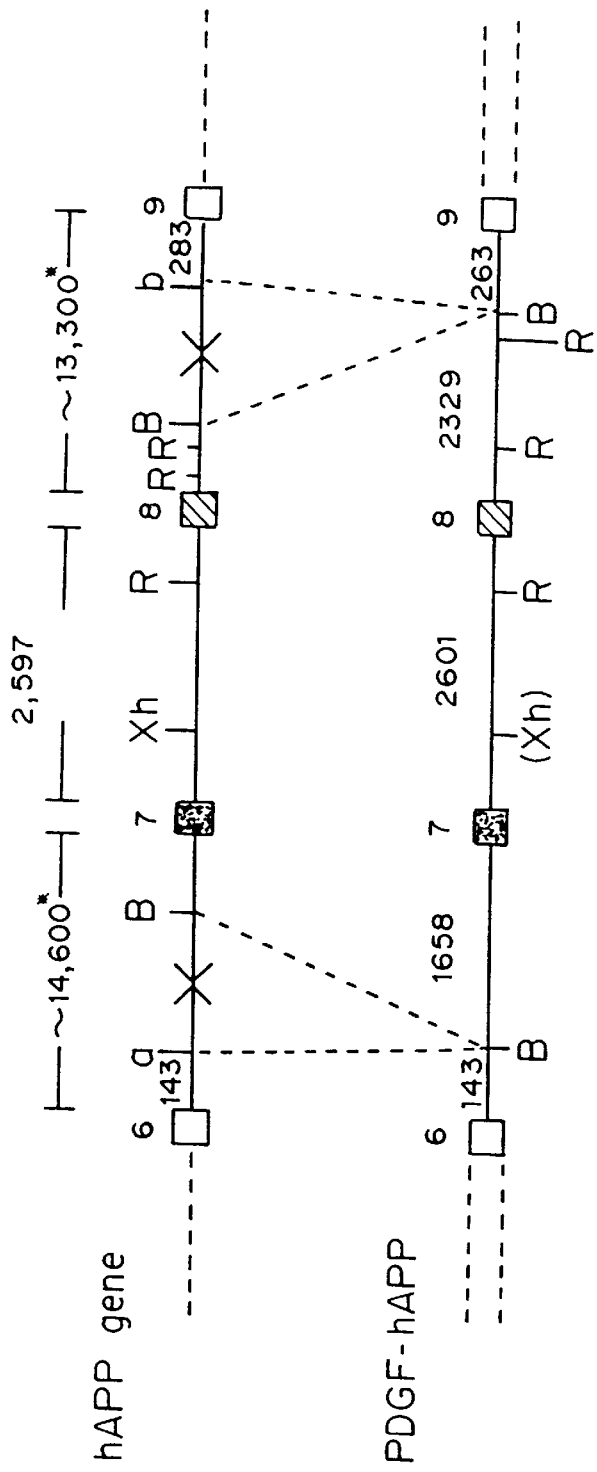
FIG. 10 is a diagram of the genomic region of APP present in the PDAPP construct. The sizes of original introns 6, 7 and 8, as well as the sizes of the final introns are indicated on the diagram. The locations of the deletions in introns 6 and 8 present in the PDAPP construct are also indicated.

APP770xE6E9x was then cut with BamHI and the 6.8 kb BamHI fragment of APP genomic DNA encoding the KPI and OX-2 domains (exons 7 and 8) was inserted at this site. This fragment starts at the BamHI site 1658 bp upstream of the start of exon 7 and extends to the first BamHI site in intron 8. This BamHI fragment was obtained from a lambda phage genomic clone encoding this portion of the APP gene, that was obtained from a Human Placental genomic library in the Lambda FIXII vector obtained from Stratagene. This BamHI fragment originally contained an XhoI site which was destroyed by cutting, filling in, and religation. The locations of the deletions are diagramed in FIG. 10. This clone, containing exons 1–8 and part of 9, and introns 6, 7 and 8, was termed the "APP splicing cassette." The APP splicing cassette was cut out with NruI and XhoI and used to replace the NruI to XhoI cDNA fragment of APP cDNA bearing the Hardy mutation. This mutant form of APP cDNA was produced by converting the G at nucleotide position 2145 to T by site directed mutagenesis. This changes the encoded amino acid from Val to Phe. The resulting construct is a combination cDNA/genomic APP "minigene."

Sequencing of the 6.8 kb BamHI fragment containing APP exons 7 and 8 derived from the APP genomic clone used to generate this construct showed that intron 7 is 2.6 kb long, and that the first BamHI site in intron 8, the upstream site of the deletion in intron 8 engineered into the APP minigene construct, is 2329 bp downstream from the end of exon 8. This does not coincide with the restriction map of the APP gene published by Yoshikai et al. (1990) and Yoshikai et al. (1991). Comparison of their map to our sequence indicates that Yoshikai et al. switched the order of two EcoRI fragments in their restriction mapping. The 1.60 kb EcoRI fragment containing exon 8 is actually upstream of the 1.48 kb EcoRI fragment and the 1.48 kb EcoRI fragment Yoshikai et al. mapped in intron 7 is actually in intron 8. We have confirmed this location for the EcoRI fragment containing exon 8 by sizing of PCR generated fragments from human DNA.

This APP minigene was operatively linked to the PDGF-B promoter to provide expression of the APP cDNA/genomic construct in mammalian cells. The PDGF β-chain 5' flanking sequence was inserted upstream of the NruI site at the beginning of the APP minigene. This fragment includes 1.3 kb upstream of the transcription initiation site, where the PDGF-B promoter resides, and approximately 70 bp of 5' untranslated region, ending at the AurII site (Higgins et al.

Figure 9:
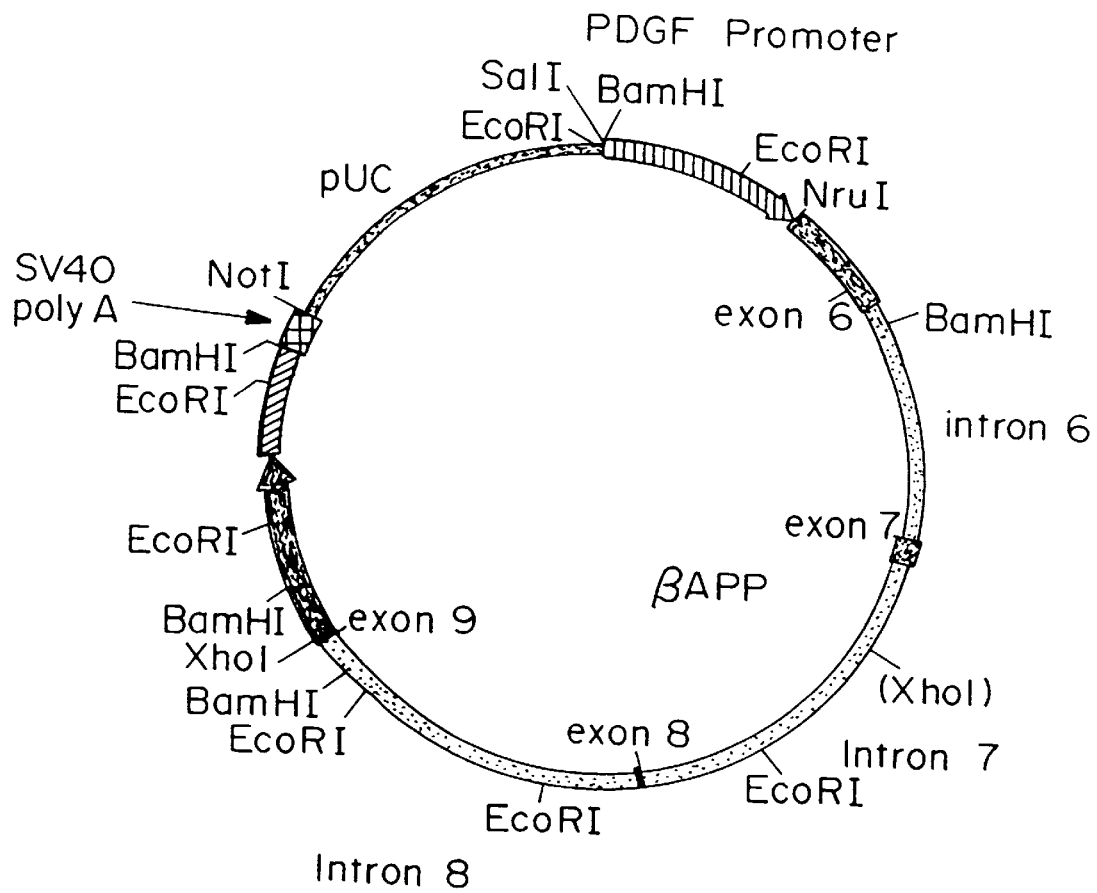
FIG. 9 is a schematic map of the PDAPP vector, a combination cDNA/genomic APP construct.

(1994)). The late SV40 polyadenylation signal, carried on a 240 bp BamHI to BclI fragment, was added downstream of the APP minigene. This construct, combining the PDGF-B promoter, the APP splicing cassette, the Hardy mutation, and the SV40 polyadenylation signal is referred to as PDAPP (FIG. 9).

EXAMPLE 6

Transgenic mice containing the PDAPP construct.

Transgenic mice were generated using the PDAPP construct described in Example 5. Transgenic mice were generated by microinjection using standard techniques as described above. PDAPP DNA was microinjected into the embryos at the two-cell stage. Plasmid sequences (pUC) were removed by Sad and NotI digestion before microinjection. Seven founder mice were generated and line 109 was used for extensive analysis. Only heterozygous animals were used. Southern analysis of 104 animals from four generations showed that approximately 40 copies of the transgene were inserted at a single site and transmitted in a stable manner. Human APP messenger RNA was produced in several tissues of the transgenic mouse, but at especially high levels in brain. RNase protection assays revealed at least 20-fold more APP expression in the brains of line 109 animals than in the mouse lines expressing neuron-specific enolase (NSE)-promoter-driven APP transgenes previously described by Quon et al. (1991), Mucke et al., *Brain Res.* 666:151–167 (1994), McConlogue et al., *Neurobiol. Aging* 15:S12 (1994), and Higgins et al., *Ann Neurol.* 35:598–607 (1994).

A. Expression of APP Transcripts and Protein.

RNA was isolated from brain tissue as described by Chomaczynski and Sacchi, *Analyt. Biochem.* 162:156–159 (1987), and subjected to RT-PCR as described by Wang et al., *Proc. Natl. Acad. Sci. U.S.A.* 86:9717–9721 (1989), using human-specific APP primers (5'-CCGATGATGACGAGGACGAT-3', SEQ ID NO:7; 5'-TGAACACGTGACGAGGCCGA-3', SEQ ID NO:8) using 40 cycles of 1 minute at 94° C., 40 seconds at 60° C., and 50 seconds at 72° C. RT-PCR analysis demonstrated the presence of transcripts encoding the 695, 751 and 770 isoforms of human APP in transgenic animal brains but not in brains from non-transgenic littermates. The identities of the human APP RT-PCR bands from the transgenic mouse RNA were verified by subcloning and sequencing.

The relative levels and alternative splicing of APP transcripts in brains of PDAPP transgenic mice, NSE-APP transgenic mice, non-transgenic mice, and humans with and without AD were compared in RNase protection assays (Rockenstein et al., *J. Biol. Chem.* 270:28257–28267 (1995)). PDAPP mice expressed approximately 5-fold higher total APP mRNA levels than non-transgenic controls, and at least 20-fold higher human APP mRNA levels than most NSE-APP transgenic mice. While NSE-driven human APP expression does not affect the levels of murine APP mRNA, PDAPP transgenic mice showed a significant 30% decrease in murine APP transcripts. While the relative abundances of murine APP770:751:695 mRNAs in non-transgenic mouse brains were roughly 1:1:35, the corresponding human APP mRNA levels in PDAPP transgenic mouse brains were 5:5:1.

Analysis of holo-APP was performed by brain homogenization in 10 volumes of PBS containing 0.5 mM EDTA, 10 $\mu$g ml$^{-1}$ leupeptin and 1 mM PMSF. Samples were spun at 12,000 g for 10 min and the pellets resuspended in RIPA (150 mM NaCl, 50 mM Tris, ph 8.0, 20 mM EDTA, 1.0% deoxycholate, 1.0% Triton X-100, 0.1% SDS, 1 mM PMSF and 10 $\mu$g ml$^{-1}$ leupeptin). Samples (each containing 30 $\mu$g total protein) were analyzed by SDS-PAGE, transferred to Immobilon membranes and reacted with either the holo-APP antibody, anti-6 (anti Bx 6), described by Oltersdorf et al., *J. Biol. Chem.* 285:4492–4497 (1990), or 8E5 monoclonal antibody. 8E5 was prepared against a bacterial fusion protein encompassing human APP residues 444–692 (Oltersdorf et al. (1990)) and is human-specific, showing essentially no crossreactivity against mouse APP. Immunoblot analysis of total APP expression (human and mouse) in transgenic mouse line 109 and control littermate brain tissue using C-terminal APP antibody anti-6 showed much higher levels of expression in the transgenic mice. Immunoblot analysis of brain homogenates using either the holo-APP polyclonal antibody anti-6 or the human-specific APP monoclonal antibody 8E5 revealed human APP over-expression in the transgenic mouse at levels at least 3-fold higher in hippocampus than either endogenous mouse APP levels or those in AD brain.

For immunoblot analysis of A$\beta$, a 9-month-old mouse brain was homogenized in 5 ml 6 M guanidine HCl, 50 mM Tris, pH 7.5. The homogenate was centrifuged at 100,000 g for 15 min and the supernatant was dialyzed against H$_2$O overnight adjusted to PBS with 1 mM PMSF and 25 $\mu$g ml$^{-1}$ leupeptin. This material was immunoprecipitated with antibody 266 resin, and immunoblotted with the human-specific A$\beta$ antibody, 6C6, as described by Seubert et al., *Nature* 359:325–327 (1992). Using this human-specific A$\beta$ antibody (6C6), a 4 kD $\beta$ amyloid-immunoreactive peptide was isolated from the brains of the transgenic animals, which corresponds to the relative molecular mass of A$\beta$. Brain levels of A$\beta$ were at least 10-fold higher in line 109 animals than in the previously described human APP transgenic mice. Embryonic day 16 cortical cell cultures from transgenic animals constitutively secreted human A$\beta$, including a substantial fraction of A$\beta$ 1–42 (5 ng ml$^{-1}$ total A$\beta$; 0.7 ng ml$^{-1}$ A$\beta$ 1–42), as detected in media by human-specific A$\beta$ enzyme-linked immunosorbent assays, as described by Seubert et al. (1992) and McConlogue et al. (1994), and as described in Example 8. Thus, line-109 animals greatly overexpressed human APP mRNA, holo-APP and A$\beta$ in their brains.

B. Histopathology of PDAPP Transgenic Mice.

Brains from 180 transgenic and 160 age-matched non-transgenic age-matched controls (4 to 20 months old) representing five generations of the line 109 pedigree were extensively examined histopathologically. Some mouse brains were removed and placed in alcohol fixative (Arai et al., *Proc. Natl. Acad. Sci. U.S.A.* 87:2249–2253 (1990)) for 48 hours before paraffin embedding. Other mice were perfused with saline followed by 4% paraformaldehyde in 0.1 M sodium phosphate. For paraffin embedded brains, 6 $\mu$m coronal or parasaggital sections from transgenic and non-transgenic mice were placed adjacent to each other on poly-L-lysine coated slides. The sections were deparaffinized, rehydrated and treated with 0.03% H$_2$O$_2$ for 30 min before overnight incubation at 4° C. with a 1:1,000 dilution of the A$\beta$ antibody, R1280 (Tamaoka et al., *Proc. Natl. Acad. Sci. U.S.A.* 89:1345–1349 (1992)). For absorption studies, synthetic human A$\beta$ 1–40 peptide (Games et al., *Neurobiol. Aging* 13:569–576 (1992)) in 10% aqueous dimethylsulphoxide was added to a final concentration of 7.0 $\mu$M to the diluted antibody and incubated for 2 hours at 37° C. The diluent was applied to the sections and processed under the same conditions as the standard antibody solution.

Peroxidase rabbit IgG kit (Vector Labs) was then used as recommended, with 3,3'-diaminobenzidine (DAB) as the chromogen. Similarly fixed human AD brain was processed simultaneously under identical conditions.

Before 4 months of age, no obvious Aβ deposition was detected. However, by approximately 4 months of age, the transgenic animals began to exhibit deposits of human Aβ in the hippocampus, corpus callosum and cerebral cortex. These Aβ plaques increased with age, and by eight months many deposits of 30 to 200 μm were seen. As the animals aged beyond 9 months, the density of the plaques increased until the Aβ-staining pattern resembled that of AD. Vascular amyloid, another feature of AD pathology, developed in older mice. Robust pathology was also seen in another transgenic line generated from the PDAPP vector (line 35).

Aβ deposits of varying morphology were clearly evident as a result of using a variety of Aβ antibodies, including well characterized human-specific Aβ antibodies and antibodies specific for the free amino and carboxy termini of Aβ 1–42. Antibody 9204, described by Saido et al., *J. Biol. Chem.* 289:15253–15257 (1994), is specific to Aβ 1–5 and was used at a concentration of 7.0 μg ml$^{-1}$. Antibody 277–2, specific for Aβ 1–42, was prepared by immunizing New Zealand white rabbits with the peptide cysteine-aminoheptanoic acid-Aβ 33–42 conjugated to cationized BSA ('Super Carriers'; Pierce) using a standard immunization protocol (500 μg per injection). Specific antibodies were affinity-purified from serum against the immunogen immobilized on agarose beads. Before incubation with antibody 277–2, sections were treated for 1 to 2 min with 80% formic acid. For detection, the antibody was reacted using the peroxidase rabbit IgG kit (Vector Labs). The product was then visualized using DAB as the chromogen, Some sections were then incubated overnight at 4° C. with a 1:500 dilution of polyclonal anti-GFAP (Sigma). The GFAP antibody was reacted using the alkaline phosphatase anti-rabbit IgG kit and alkaline phosphatase substrate kit 1 (Vector Labs; used according to the manufacturer's recommendations). Additional sections were incubated overnight with the F480 antibody (Serotec) used at a 1:40 dilution to visualize microglial cells. The mouse peroxidase kit (Vector Labs) was then used according to the manufacturer's recommendations. Some sections were stained with thioflavin S using standard procedures (Dickson et al., *Acta Neuropath.* 79:486–493 (1990)) and viewed with ultraviolet light through an FITC filter of maximum wavelength 440 nm.

Serial sections demonstrated many plaques were positively stained with both the 9204 and 277–2 antibodies. The forms of the Aβ deposition ranged from diffuse irregular types to compacted plaques with cores. Roughly spherical, and wispy, irregular deposits, were labelled with antibody 9204 specific for the free amino terminus of Aβ. Astrocytic gliosis associated with Aβ deposition was evident after double immunolabelling with antibodies to glial fibrillary acidic protein (GFAP) and human Aβ. A compacted Aβ core and 'halo' was evident in several plaques. Non-transgenic littermates showed none of these neuropathological changes. Immunostaining was fully absorbable with the relevant synthetic peptide, and was apparent using a variety of processing conditions, including fixation with paraformaldehyde and Trojanowski methods. Many plaques were stained with thioflavin S, and some were also stained using the Bielschowsky silver method and were birefringent with Congo Red, indicating the true amyloid nature of these deposits.

The majority of plaques were intimately surrounded by GFAP-positive reactive astrocytes, similar to the gliosis found in AD plaques. The neocortices of the transgenic mice contained diffusely activated microglial cells, as defined by their amoeboid appearance, shortened processes, and staining with Mac-1 antibody. Staining by antibodies recognizing phosphorylated neurofilaments and phosphorylated tau indicated that aberrant phosphorylation occurred in PDAPP brain that was similar to AD. These phosphorylations are seen in AD and are thought to preclude formation of neurofibrillary tangles. Although paired helical filaments (PHF) have not yet been detected in PDAPP mice, the detection of abnormally phosphorylated neurofilaments and tau are thought to be associated with, and the initial step in, the formation of PHF in AD.

Clear evidence for neuritic pathology was apparent using both conventional and confocal immunomicroscopy. Forty μm thick vibratome sections were incubated overnight at 4° C. with R1280 (1:1,000) in combination with polyclonal anti-synaptophysin (1:150; Dako) or 8E5 (7.0 μg $^{-1}$). Some sections were incubated with anti-synaptophysin or monoclonal anti-MAP 2 (1:20, Boehringer-Mannheim), and then reacted with a goat anti-rabbit biotinylated antibody (1:100) followed by a mixture of FITC-conjugated horse anti-mouse IgG (1:75) and avidin D Texas red (1:100) (Vector Labs). The double-immunolabelled sections were viewed on a Zeiss Axiovert 35 microscope with attached laser confocal scanning system MRC 600 (Bio-Rad). The Texas red channel collected images of the R1280 or synaptophysin labelling, and the FITC channel collected synaptophysin, 8E5, or MAP 2 labelling. Optical z-sections 0.5 μm in thickness were collected from each region, similar to the image processing and storage described by Masliah et al., *J. Neuropath. Exp Neurol.* 52:619–632 (1993).

Many Aβ plaques were closely associated with distorted neurites that could be detected with human APP-specific antibodies and with anti-synaptophysin antibodies, suggesting that these neurites were derived in part from axonal sprouts, as observed in the AD brain. The plaques compressed and distorted the surrounding neuropil, also as in the AD brain. Synaptic and dendritic density were also reduced in the molecular layer of the hippocampal dentate gyrus of the transgenic mice. This was evident by reduced immunostaining for the presynaptic marker synaptophysin and the dendritic marker MAP-2 in AD brain (Masliah et al., *Am. J. Path.* 138:235–246 (1991)).

Confirmation of the presence of extracellular Aβ was obtained using immunoelectron microscopy. For immunoelectron microscopy, mice were perfused with saline followed by 2.0% paraformaldehyde and 1.0% glutaraldehyde in cacodylate buffer. Forty μm thick vibratome sections were incubated with the R1280 antibody, and reacted using a peroxidase rabbit IgG kit (Vector Labs). Immunolabelled sections with Aβ deposits were then fixed in 1.0% ammonium tetraoxide and embedded in epon/araldite before viewing ultrathin sections with a Jeol CX100 electron microscope (Masliah et al., *Acta Neuropath.* 81:428–433 (1991)).

TABLE 3

Ultrastructural Similarities and Differences Between AD and PDAPP Transgenic Plaques.

|  | Alzheimer's Disease | PDAPP |
|---|---|---|
| Amyloid fibrils | | |
| size | 9–11 mn | 9–11 nm |
| electron density | moderate | high |

TABLE 3-continued

Ultrastructural Similarities and Differences
Between AD and PDAPP Transgenic Plaques.

|  | Alzheimer's Disease | PDAPP |
|---|---|---|
| pinocytic vesicles | abundant | occasional |
| Dystrophic neurites | | |
| TYPE I | | |
| dense laminar bodies | abundant | abundant |
| synaptic vesicles and contacts | yes | yes |
| neurofilament accumulation | yes | yes |
| TYPE II | | |
| paired helical filaments | yes | none? |
| Cells associated with amyloid formation | | |
| microglia | abundant | occasional |
| neurons | occasional | abundant |
| neurosecretory granules | abundant | abundant |
| rough endoplasmic reticulum | abundant | abundant |
| coated pits | yes | yes |

Tables 3 and 4 present a summary of the above results, showing cytological and pathological similarities between AD and PDAPP mice. For every feature examined, with the exception of paired helical filaments, the PDAPP mice exhibited pathology characteristic of AD. These findings show that production of human APP in transgenic (TG) mice is sufficient to cause not only amyloid deposition, but also many of the complex subcellular degenerative changes associated with AD.

TABLE 4

Pathology in Alzheimer's Disease and the PDAPP Mouse.

|  | Alzheimer's Disease | PDAPP |
|---|---|---|
| Aβ Deposition into Plaques | | |
| Diffuse | + | + |
| Neuritic | + | + |
| Vascular | + | + |
| Brain Region Specificity | + | + |
| Neuritic Dystrophy | + | + |
| Synaptic Loss | + | + |
| Inflammatory Response | | |
| Astrocytosis | + | + |
| Microgliosis | + | + |
| Cytoskeletal Alterations | | |
| Phosphorylated Neurofilaments | + | + |
| Phosphorylated Tau | + | + |
| PHF/Tangles | + | −(?) |

The most notable feature of these transgenic mice is their Alzheimer-like neuropathology, which includes extracellular Aβ deposition, dystrophic neuritic components, gliosis, and loss of synaptic density with regional specificity resembling that of AD. Plaque density increases with age in these transgenic mice, as it does in humans (Selkoe, *Rev. Neurosi.* 17:489–517 (1994)), implying a progressive Aβ deposition that exceeds its clearance, as also proposed for AD (Maggio et al., *Proc. Natl. Acad. Sci. U.S.A.* 89:5462–5466 (1992)). The PDAPP transgenic mice provide strong new evidence for the primacy of APP expression and Aβ deposition in AD neuropathology. Such mice also provide a sufficiently robust AD model in which to test whether compounds that lower Aβ production and/or reduce its neurotoxicity in vitro can produce beneficial effects in an animal model prior to advancing such drugs into human trials.

EXAMPLE 7

Construction APP transgenes expressing APP from the PDGF-B promoter.

PDAPP transgenic mice contain a splicing cassette that permits expression of all three major human APP isoforms, where expression is driven by the PDGF-B promoter, and which includes a mutation in amino acid 717, the site of familial AD mutations. It is expected that these features, and others described above, can be used independently to produce transgenic mice useful as models of Alzheimer's disease. Some specific examples of such constructs are described below.

A. Construction of PDAPP-wt.

Figure 12:
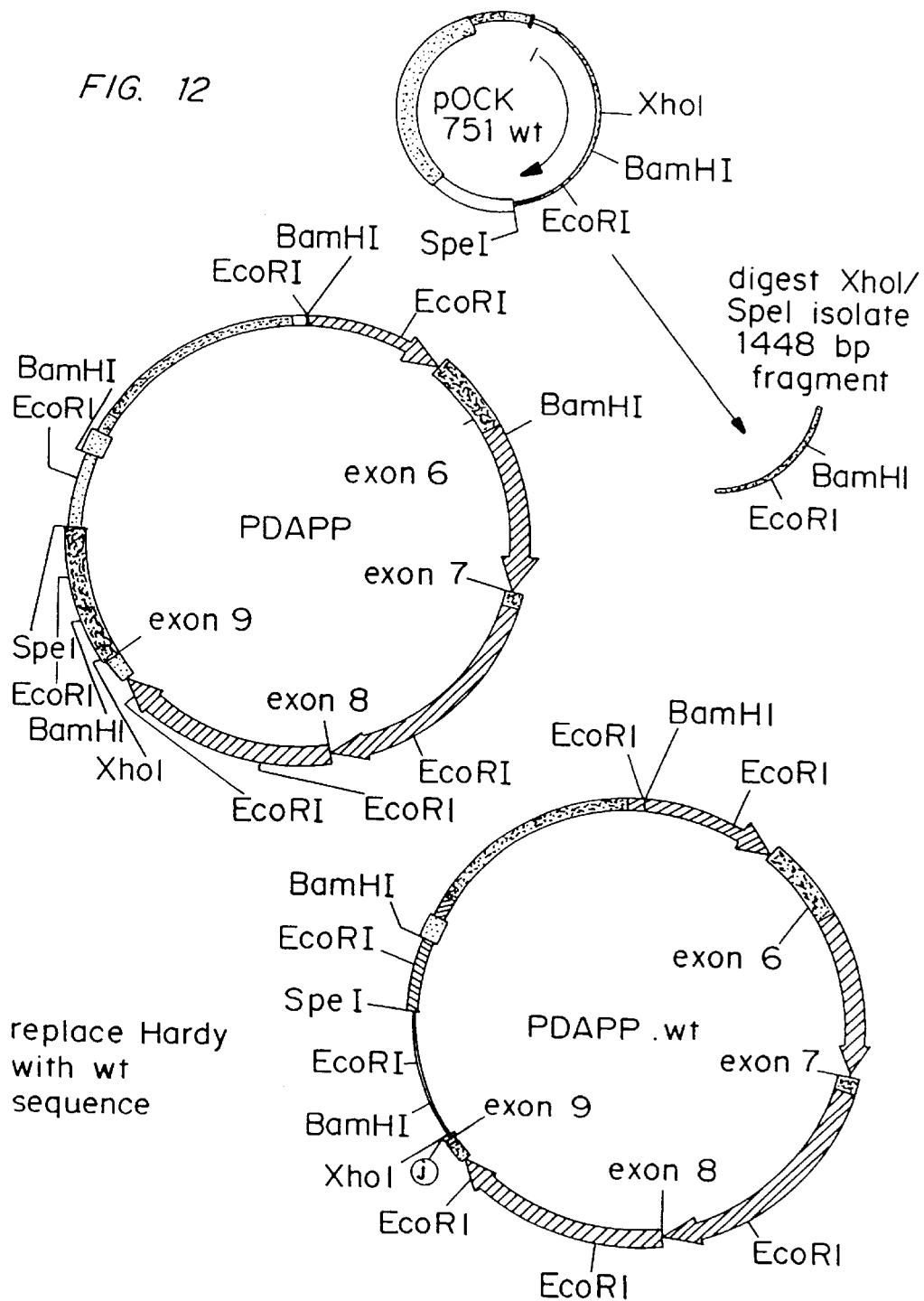
FIG. 12 is a diagram of the PDAPP-wt vector and the plasmids used to make the PDAPP-wt vector.

A wild type version of the cDNA/genomic clone PDAPP was constructed in which the mutation to amino acid 717 was replaced with the wild type. This was accomplished by replacing the 1448 bp XhoI to SpeI fragment of PDAPP, which includes the part of the APP cDNA sequence that encodes the Hardy mutation in which Val717 is replaced by Phe, with the 1448 bp XhoI to SpeI fragment of a wild type APP clone. This fragment corresponds to the region from position 1135 to 2588 of SEQ ID NO:5. None of the intron sequences of PDAPP are replaced or removed by this substitution. This construct is referred to as PDAPP-wt. A schematic of PDAPP-wt and its construction is shown in FIG. 12.

B. Construction of PDAPP-SwHa.

Another version of the cDNA/genomic clone PDAPP was constructed in which the Swedish mutant at amino acids 670 and 671 was introduced. Plasmid pNSE751.delta3'spl.sw contains cDNA of the human APP751 which includes the Swedish mutation of Lys to Asn and Met to Leu at amino acids 670 and 671, respectively. A 563 bp EcoRI to SpeI fragment from this plasmid was replaced with the corresponding 563 bp EcoRI to SpeI fragment of PDAPP, which includes an identical part of the APP cDNA sequence with the exception of Phe717 of the Hardy mutation. This fragment corresponds to the region from position 2020 to 2588 of SEQ ID NO:5. This results in pNSE.delta3'spl.sw/ha, which contains both the Swedish mutation at amino acids 670 and 671, and the Hardy mutation at amino acid 717.

Figure 13:
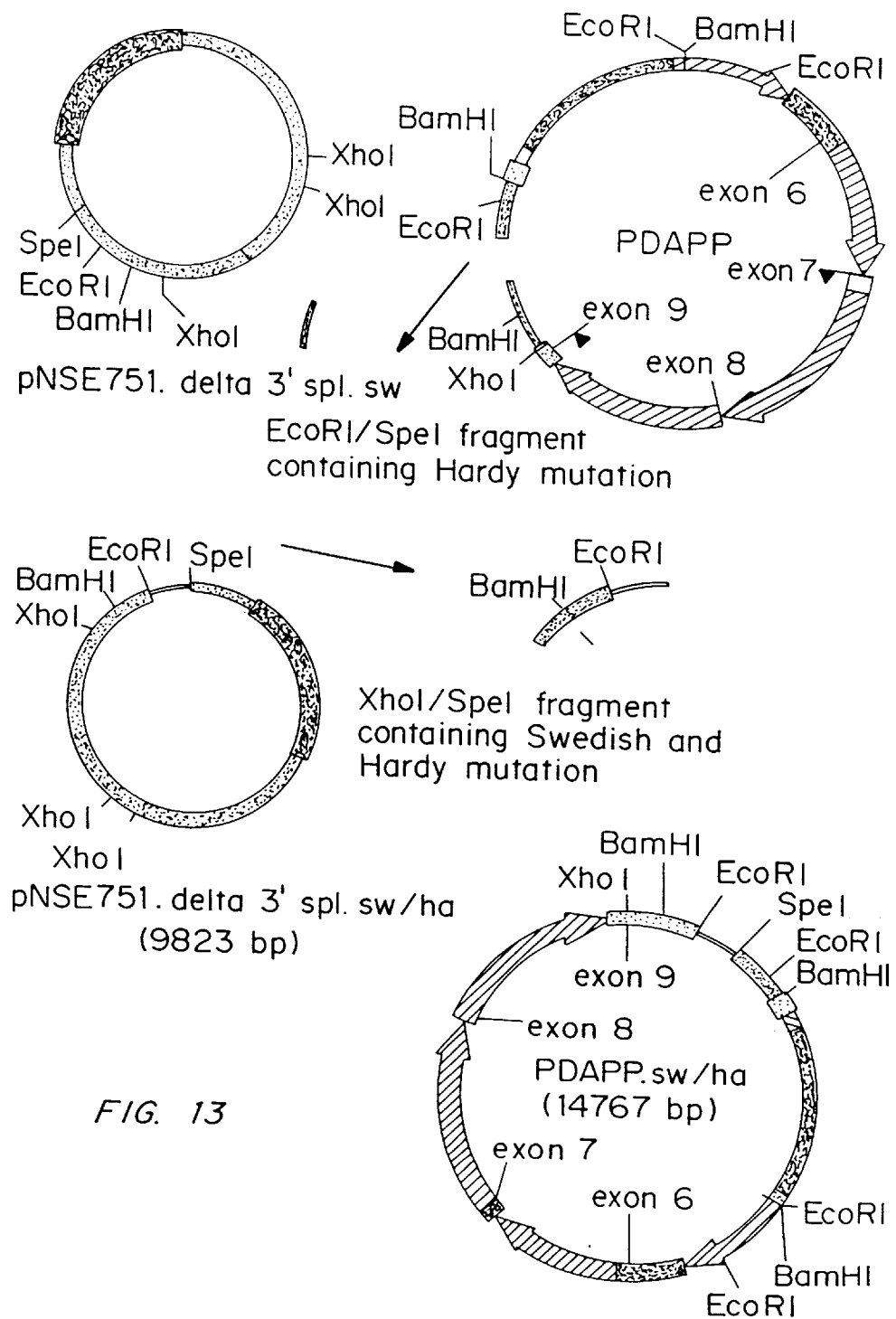
FIG. 13 is a diagram of the PDAPP-Sw/Ha vector and the plasmids and intermediate constructs used to make the PDAPP-Sw/Ha vector.
Figure 14:
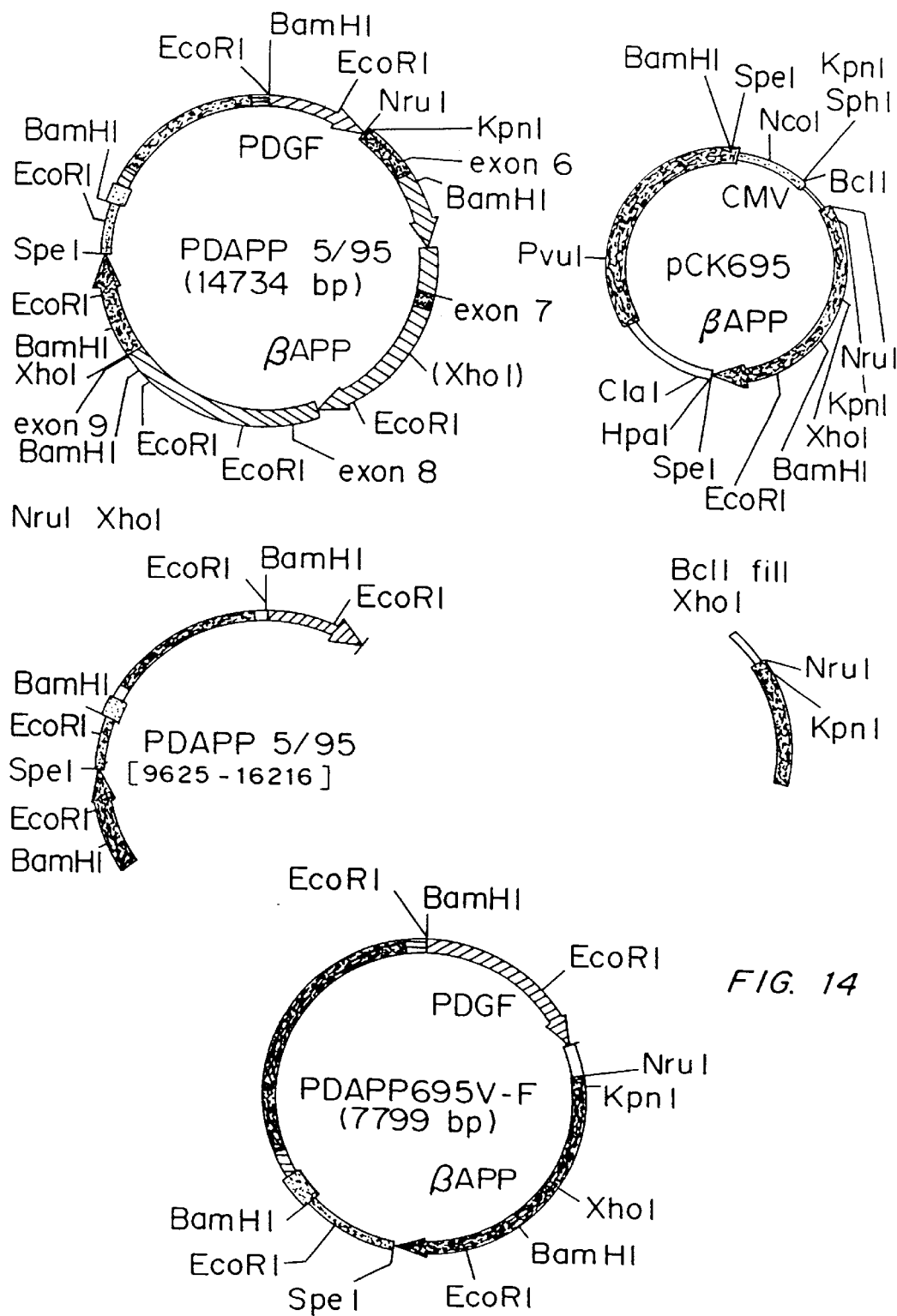
FIG. 14 is a diagram of the PDAPP695$_{V-F}$ vector and the plasmids and intermediate constructs used to make the PDAPP695$_{V-F}$ vector.
Figure 15A:
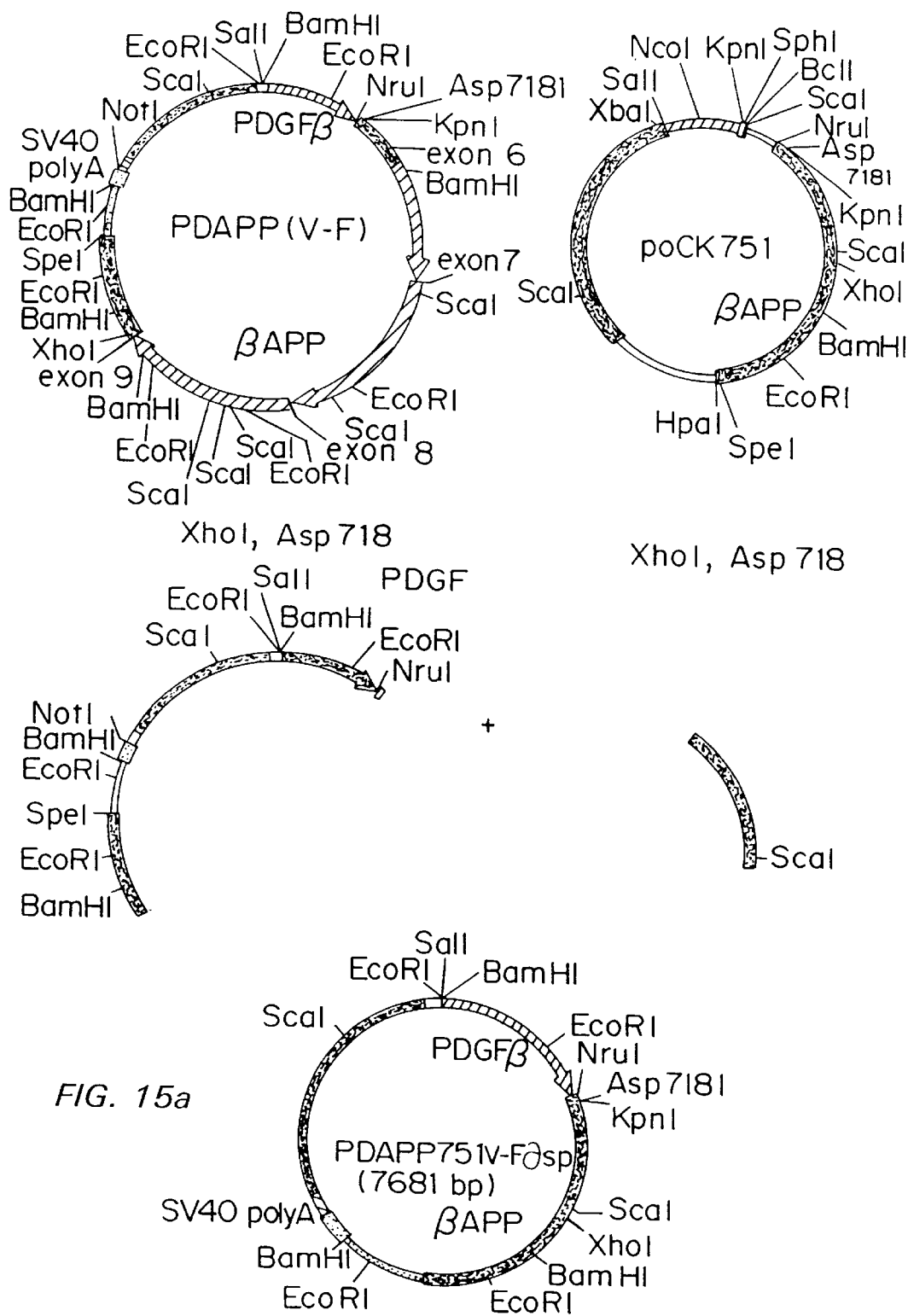
FIGS. 15a and 15b are a diagram of the PDAPP751$_{V-F}$ vector and the plasmids and intermediate constructs used to make the PDAPP751$_{V-F}$ vector.
Figure 15B:
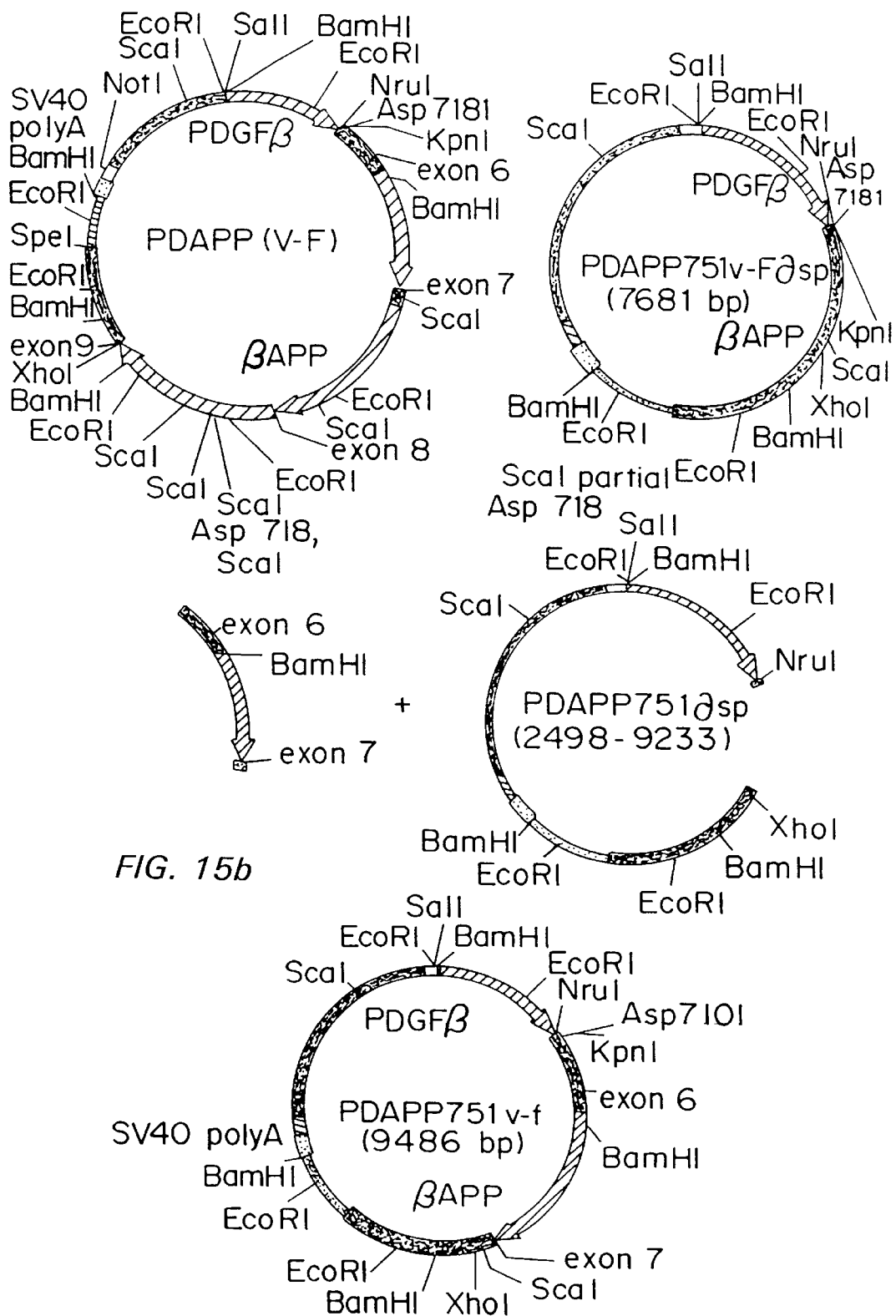

The 1448 bp XhoI to SpeI fragment of PDAPP was then replaced with the 1448 bp XhoI to SpeI fragment of pNSE752.delta3'spl.sw/ha, which contains both the Swedish mutation and the Hardy mutation, to form PDAPP-Sw/Ha. A schematic of PDAPP-Sw/Ha and its construction is shown in FIG. 13.

C. Construction of PDAPP695$_{V-F}$.

A construct encoding only APP695, but retaining the Hardy mutation, PDGF-B promoter, and vector sequences of PDAPP, can be made. This can be accomplished by ligating the 6.6 kb XhoI to NruI fragment from PDAPP, which contains the C-terminal part of the APP sequences, and the polyadenylation, pUC, and PDGF-B promoter sequences, to the 1.2 kb XhoI to BclI fragment of pCK695, which contains a hybrid splice signal and the remaining N-terminal portion of the APP sequences (on a 911 bp XhoI to NruI fragment of APP695 cDNA). The hybrid splice signal is the same as was described earlier and is also present in vector pohCK751, which is described by Dugan et al., *J Biological Chem.* 270:10982–10989 (1995). pCK695 is identical to pohCK751 except that the herpes simples virus replication and packaging sequences of pohCK751 were removed, and the plasmid encodes APP695 instead of APP751.

In this vector the PDGF-B promoter drives the expression of APP695 containing the mutation of Val717 to Phe. The hybrid splice signal is included to potentially enhance expression. Additional vectors derived from this may be constructed which lack any splice signals, or into which other splice signals have been added to obtain this same function.

D. Construction of PDAPP751$_{V-F}$.

A construct encoding only APP751, but retaining the Hardy mutation, PDGF-B promoter, and vector sequences of PDAPP, can be made. This can be accomplished by ligating the 6.65 kb XhoI to KpnI fragment of PDAPP, including part of the APP sequences, the polyadenylation signals, pUC and PDGF-B promoter sequences to the 1.0 kb KpnI to XhoI fragment containing the remainder of the human APP751 cDNA sequences (nucleotides 57 to 1084 of SEQ ID NO:3) to make the intermediate plasmid PDAPPδsp751$_{V-F}$. The 1.0 kb KpnI to XhoI fragment encoding a portion of human APP751 can be obtained from the plasmid poCK751, which is identical to pohCK751 except that the herpes simplex viral sequences were removed.

To introduce splicing sequences, the first intron from PDAPP, which is intron Δ6, is then inserted into PDAPPδsp751$_{V-F}$ to make PDAPP751$_{V-F}$. To accomplish this, the 2,758 bp Asp718 to ScaI fragment of PDAPP containing exons 2 through 6, intron Δ6, and part of exon 7, is ligated to the 6,736 bp fragment obtained by complete digestion of PDAPPδsp751$_{V-F}$ with Asp718 and partial digestion with ScaI. This 6,736 bp fragment provides the remaining additional APP sequences (part of exon 1, the rest of exon 7, and exons 9 through 18), polyadenylation signals, pUC and PDGF-B promoter sequences. The resulting construct is referred to as PDAPP751$_{V-F}$.

In this vector the PDGF-B promoter drives the expression of APP751 containing the mutation of Val717 to Phe. One splice signal (derived from intron 6) is included to potentially enhance expression. Additional vectors derived from this may be constructed which lack any splice signals, or into which other splice signals have been added to obtain this same function.

E. Construction of PDAPP770$_{V-F}$.

A construct encoding only APP770, but retaining the Hardy mutation, PDGF-B promoter, and vector sequences of PDAPP, can be made. This can be accomplished by replacing the KpnI to XhoI fragment of PDAPP751$_{V-F}$ containing APP exons 2–7 and a part of exon 9, with the KpnI to XhoI fragment of APP770 cDNA, which contains exons 2–8 and a part of exon 9. This fragment corresponds to nucleotides 57 to 1140 of SEQ ID NO:5. The resulting construct is referred to as PDAPP770$_{V-F}$.

In this vector the PDGF-B promoter drives the expression of APP770 containing the mutation of Val717 to Phe. PDAPP770$_{V-F}$ contains the same intron sequences present in PDAPP751$_{V-F}$. Additional vectors derived from this may be constructed into which a splice signals have been added to obtain enhanced expression.

EXAMPLE 8

Expresssion Levels of APP Expression Products in Brain Tissue of PDAPP Mice.

The PDAPP mouse line described in Example 6 was examined for the levels of several derivatives of the APP in hippocampal, cortical, and cerebellar brain regions of mice of various ages. Levels of APP cleaved at the beta-secretase site (APPβ) and APP containing at least 12 amino acids of Aβ (FLAPP+APPα; a mixture of APPα and full length APP (FLAPP)) were found to be nearly constant within a given brain region at all ages evaluated. The hippocampus expressed the highest level of all APP forms. In contrast, guanidine extractable levels of Aβ showed remarkable age-dependent increases in a manner that mirrored the amyloid plaque deposition observed immunohistochemically. Specifically, Aβ levels in hippocampus increased 17-fold by 8 months of age and 106-fold by 1 year of age, compared to that found in 4 month old animals. At 1 year of age Aβ constitutes approximately 1% of the total protein in hippocampus. The cerebral cortex also showed large increases in Aβ with age. In contrast, the mean level of Aβ in cerebellum across all age groups was comparatively low and unchanging.

Further analysis of the Aβ in these brains using an ELISA specific for Aβ$_{1-42}$ showed that this longer version made up 27% of the 19 pmoles/g of the Aβ present in the brains of young animals; this percentage increased to 97% of the 690 pmoles/g in 12 month old animals. The selective deposition of Aβ$_{1-42}$ and the spacial distribution of the Aβ deposits are further evidence that the pathological processes ongoing in the PDAPP transgenic mice parallel the human Alzheimer's diseased condition.

Levels of Aβ-containing proteins were measured through the use of ELISAs configured with antibodies specific to Aβ, Aβ$_{1-42}$, APP cleaved at the β-secretase site (Seubert et al. (1993)), and APP containing the first 12 amino acids of Aβ (FLAPP+APPα; a mixture of full length APP and α-secretase cleaved APP (Esch et al.)). Striking similarities in both the regional variation and depositing form of Aβ are noted between the mouse model and the human AD condition. The results also show that, because of the magnitude and temporal predictability of Aβ deposition, the PDAPP mouse is a practical model in which to test agents that either inhibit the processing of APP to Aβ or retard Aβ amyloidosis.

A. Materials and Methods.

1. Brain Tissue Preparation.

The heterozygote transgenic (Line 109, Games et al.; Rockenstein et al.) and non-transgenic animals were anesthetized with Nembutol (1:5 solution in 0.9% saline) and perfused intracardially with ice cold 0.9% saline. The brain was removed and one hemisphere was prepared for immunohistochemical analysis, while four brain regions (cerebellum, hippocampus, thalamus, and cortex) were dissected from the other hemisphere and used for Aβ and APP measures.

To prepare tissue for ELISAs, each brain region was homogenized in 10 volumes of ice cold guanidine buffer (5.0 M guanidine-HCl, 50 mM Tris-Cl, pH 8.0) using a motorized pestle (Kontes). The homogenates were gently mixed on a Nutator for three to four hours at room temperature, then either assayed directly or stored at −20° C. prior to quantitation of Aβ and APP. Preliminary experiments showed the analytes were stable to this storage condition.

2. Aβ Measurements.

The brain homogenates were further diluted 1:10 with ice-cold casein buffer (0.25% casein, phosphate buffered saline (PBS), 0.05% sodium azide, 20 μg/ml aprotinin, 5 mM EDTA pH 8.0, 10 μg/ml leupeptin), reducing the final concentration of guanidine to 0.5 M, before centrifugation (16,000× g for 20 minutes at 4° C.). The Aβ standards (1–40 or 1–42 amino acids) were prepared such that the final composition included 0.5 M guanidine in the presence of 0.1% bovine serum albumin (BSA).

The "total" Aβ sandwich ELISA consists of two monoclonal antibodies (mAb) to Aβ. The capture antibody, 266, is specific to amino acids 13–28 of Aβ (Seubert et al. (1992)); while the antibody 3D6, which is specific to amino acids 1–5 of Aβ, was biotinylated and served as the reporter antibody. The 3D6 biotinylation procedure employs the manufacturer's (Pierce) protocol for NHS-biotin labeling of immunoglobulins except 100 mM sodium bicarbonate, pH 8.5 buffer was used. The 3D6 antibody does not recognize secreted APP or full-length APP but detects only Aβ species with amino terminal aspartic acid. The assay has a lower limit of sensitivity of approximately 50 pg/ml (11.4 pM) and showed no cross-reactivity to the endogenous murine Aβ peptide at concentrations up to 1 ng/ml.

The configuration of the $A\beta_{1-42}$-specific sandwich ELISA employs the mAb 21F12, which was generated against amino acids 33–42 of Aβ. The antibody shows less than 0.4% cross-reactivity with $A\beta_{1-40}$ in either ELISA or competitive radioimmunoassay (RIA). Biotinylated 3D6 is also the reporter antibody in this assay which has a lower limit of sensitivity of approximately 125 pg/ml (28.4 pM).

The 266 and 21F12 mAbs were coated at 10 µg/ml into 96-well immunoassay plates (Costar) overnight at room temperature. The plates were then aspirated and blocked with 0.25% human serum albumin in PBS buffer for at least 1 hour at room temperature, then stored desiccated at 4° C. until use. The plates were rehydrated with wash buffer prior to use. The samples and standards were added to the plates and incubated at room temperature for 1 hour. The plates were washed at least 3 times with wash buffer (Tris buffered saline, 0.05% Tween 20) between each step of the assay.

The biotinylated 3D6, diluted to 0.5 µg/ml in casein assay buffer (0.25% casein, PBS, 0.05% Tween 20, pH 7.4), was incubated in the well for 1 hour at room temperature. Avidin-HRP (Vector, Burlingame, Calif.), diluted 1:4000 in casein assay buffer, was added to the wells and incubated for 1 hour at room temperature. The calorimetric substrate (100 µl), Slow TMB-ELISA (Pierce), was added and allowed to react for 15 minutes, after which the enzymatic reaction is stopped with 25 µl of 2 N $H_2SO_4$. Reaction product was quantified using a Molecular Devices Vmax measuring the difference in absorbance at 450 nm and 650 nm.

3. APP ELISAs.

Two different APP assays were utilized. The first recognizes APPα and full length forms of APP (FLAPP+APPα), while the second recognizes APPβ (APP ending at the methionine preceding the Aβ domain (Seubert et al. (1993)). The capture antibody for both the FLAPP+APPα and APPβ assays is 8E5, a monoclonal antibody raised to a bacterially expressed fusion protein corresponding to human APP amino acids 444–592 (Games et al.). The reporter mAb (2H3) for the FLAPP+APPα assay was generated against amino acids 1–12 of Aβ. The lower limit of sensitivity for the 8E5/2H3 assay is approximately 11 ng/ml (150 pM). For the APPβ assay, the polyclonal antibody 192 was used as the reporter. This antibody has the same specificity as antibody 92 (Seubert et al. (1993)), that is, it is specific to the carboxy-terminus of the β-secretase cleavage site of APP. The lower limit of sensitivity for the β-secretase 8E5/192 assay is approximately 43 ng/ml (600 pM).

For both APP assays, the 8E5 mAb was coated onto 96-well Costar plates as described above for 266. Purified recombinant secreted APPα (the APP751 form) and APP596 were the reference standards used for the FLAPP+APPα and APPβ assays, respectively. APP was purified as described previously (Esch et al.) and APP concentrations were determined by amino acid analysis. The 5 M guanidine brain homogenate samples were diluted 1:10 in specimen diluent for a final buffer composition of 0.5 M NaCl, 0.1% NP-40, 0.5 M guanidine. The APP standards for the respective assays were diluted into buffer of the same final composition as for the samples. The APP standards and samples were added to the plate and incubated for 1.5 hours at room temperature. The plates were thoroughly washed between each step of the assay with wash buffer. Reporter antibodies 2H3 and 192 were biotinylated following the same procedure as for 3D6 and were incubated with samples for 1 hour at room temperature. Streptavidin-alkaline phosphatase (Boehringer Mannheim), diluted 1:1000 in specimen diluent, was incubated in the wells for 1 hour at room temperature. The fluorescent substrate 4-methyl-umbellipheryl-phosphate, was added, and the plates read on a Cytofluor™ 2350 (Millipore) at 365 nm excitation and 450 nm emission.

4. Monoclonal Antibody Production.

The immunogens for 3D6, 21F12, and 2H3 were separately conjugated to sheep anti-mouse immunoglobulin (Jackson Immunoresearch Labs) using maleimidohexanoyl-N-hydroxysuccinimide (Pierce). A/J mice (Jackson Laboratories) were given intraperitoneal injections (IP) of 100 µg of the appropriate immunogen emulsified in Freund's complete adjuvant (Sigma) and two subsequent IP injections of 100 µg immunogen were given on a biweekly basis in Freund's incomplete adjuvant (Sigma). Two to three weeks after the third boost, the highest titer mouse of a given immunogen was injected intravenously and intraperitoneally with 50–100 µg of immunogen in PBS. Three days post injection, the spleen was removed, splenocytes were isolated and fused with SP2/0-Ag14 mouse myeloma cells. The hybridoma supernatants were screened for high affinity monoclonal antibodies by RIA as previously described (Seubert et al. (1992)). Purified monoclonal antibodies were prepared from ascites.

5. Immunohistochemistry.

The tissue from one brain hemisphere of each mouse was drop-fixed in 4% paraformaldehyde and post-fixed for three days. The tissue was mounted coronally and 40 µm sections were collected using a vibratome. The sections were stored in anti-freeze at −20° C. prior to staining. Every sixth section, from the posterior part of the cortex through the hippocampus, was immunostained with biotinylated 3D6 at 4° C., overnight. The sections were then incubated with horseradish peroxidase avidin-biotin complex (Vector) and developed using 3,3'-diaminobenzidine (DAB) as the chromogen.

B. Results.

1. Aβ and APP Assays.

The FLAPP+APPα assay recognizes secreted APP including the first 12 amino acids of Aβ. Since the reporter antibody ($2H3_{1-12}$) is not specific to the alpha clip site occurring between Aβ amino acids 16 and 17 (Esch et al.), this assay also recognizes full length APP. Preliminary experiments using immobilized APP antibodies to the cytoplasmic tail of full length APP to deplete the mixture suggest that approximately 30 to 40% of the FLAPP+APPα is full length. The APPβ assay recognizes only the APP clipped immediately amino-terminal to the Aβ region due to the specificity of the polyclonal reporter antibody 192 (Seubert et al. (1993)).

The specific nature of the Aβ immunoreactivity was further characterized as follows. Guanidine homogenates of brain (excluding cerebellum and brain stem) were subjected to size exclusion chromatography (Superose 12) and the resulting fractions analyzed using the total Aβ assay. Comparisons were made of 2, 4, and 12 month transgenic mouse brain homogenates and a non-transgenic mouse brain homogenate to which $Aβ_{1-40}$, had been spiked at a level roughly equal to that found in the 12 month old transgenic mice. The elution profiles of the transgenic brain homogenate were similar in that the peak fractions of Aβ immunoreactivity occurred in the same position, a single broad symmetric peak which was coincident with the immunoreactive peak of spiked $Aβ_{1-40}$. Attempts were then made to immunodeplete the Aβ immunoreactivity using resin bound antibodies against Aβ (mAb 266 against $Aβ_{13-28}$), the secreted forms of APP (mAb 8E5 against $APP_{444-593}$ of the APP695 form), the carboxy-terminus of APP (mAb 13G8 against $APP_{676-695}$ of the APP695 form), or heparin agarose. Only the 266 resin captured Aβ immunoreactivity, demonstrating that full length APP or carboxy-terminal fragments of APP are not contributing to the Aβ measurement. The $Aβ_{1-42}$ ELISA employs a capture antibody that recognizes $Aβ_{1-42}$ but not $Aβ_{1-40}$. The $Aβ_{1-42}$ assay, like the total Aβ assay, is not affected by the full length or carboxy-terminal forms of APP containing the Aβ region in the homogenates as shown by similar immunodepletion studies.

2. Total Aβ and APP Measures.

Table 5 shows the levels of total Aβ, FLAPP+APPα, and APPβ in the hippocampus, cortex, cerebellum, and thalamus of transgenic mice as a function of age. Each data point represents the mean value for each age group. The relative levels of FLAPP+APPα and APPβ in all four brain regions remain relatively constant over time. The hippocampus expresses the highest levels of FLAPP+APPα and APPβ followed by the thalamus, cortex, and cerebellum, respectively. In the hippocampus, the levels of FLAPP+APPα are approximately 3.5 to 4.5-fold higher than APPβ at all ages. The mean value of all ages for FLAPP+APPα and APPβ assays in the hippocampus were 674 (±465) pmoles/gram and 175 (±11) pmoles/gram, respectively. From this it can be estimated that the pool of brain APP consists of approximately 50% APPα, 30% full length APP, and 20% APPβ.

TABLE 5

PDAPP Transgene Cohort Animal Data
Total Aβ & APP Measures in pmoles/gram of Brain Tissue.

| AGE IN MONTHS | Aβ & APP FORM | CEREBELLUM | HIPPOCAMPUS | CORTEX | THALAMUS |
|---|---|---|---|---|---|
| 2 | Aβ | 4.03 ± 1.08 (n = 8) | 35.41 ± 6.38 (n = 8) | 14.25 ± 2.27 (n = 8) | 6.41 ± 1.59 (n = 8) |
| 2 | FLAPP + APPα | ND | ND | ND | ND |
| 2 | APPβ | ND | ND | ND | ND |
| 4 | Aβ | 4.10 ± 0.61 (n = 14) | 38.08 ± 6.51 (n = 14) | 15.95 ± 2.60 (n = 14) | 7.60 ± 1.52 (n = 14) |
| 4 | FLAPP + APPα | 395 ± 120 (n = 14) | 703 ± 106 (n = 14) | 446 ± 70 (n = 14) | 6.37 ± 166 (n = 14) |
| 4 | APPβ | 78 ± 38 (n = 14) | 198 ± 30 (n-14) | 126 ± 23 (n = 14) | 70 ± 17 (n = 14) |
| 6 | Aβ | 4.55 ± 1.38 (n = 10) | 87.48 ± 30.33 (n = 10) | 30.19 ± 8.33 (n = 10) | 8.34 ± 2.40 (n = 10) |
| 6 | FLAPP + APPα | 403 ± 77 (n = 10) | 694 ± 107 (n = 10) | 506 ± 97 (n = 10) | 670 ± 156 (n = 10) |
| 6 | APPβ | 51 ± 87 (n = 10) | 194 ± 35 (n = 10) | 129 ± 25 (n = 10) | 56 ± 33 (n = 10) |
| 6.5 | Aβ | 5.42 ± 1.08 (n = 10) | 133.63 ± 57.10 (n = 10) | 33.27 ± 12.19 (n = 10) | 8.83 ± 1.19 (n = 10) |
| 6.5 | FLAPP + APPα | 346 ± 74 (n = 10) | 580 ± 115 (n = 10) | 436 ± 63 (n = 10) | 553 ± 123 (n = 10) |
| 6.5 | APPβ | 27 ± 77 (n = 10) | 169 ± 41 (n = 10) | 108 ± 16 (n = 10) | 58 ± 22 (n = 10) |
| 7 | Aβ | 4.44 ± 0.56 (n = 10) | 200.77 ± 94.68 (n = 10) | 60.55 ± 27.13 (n = 10) | 8.94 ± 1.19 (n = 10) |
| 7 | FLAPP + APPα | 378 ± 70 (n = 10) | 656 ± 73 (n = 10) | 469 ± 62 (n = 10) | 604 ± 107 (n = 10) |
| 7 | APPβ | 56 ± 52 (n = 10) | 176 ± 27 (n = 10) | 101 ± 20 (n = 10) | 56 ± 28 (n = 10) |
| 7.5 | Aβ | 5.14 ± 1.39 (n = 10) | 461.35 ± 345.95 (n = 10) | 81.839 ± 53.00 (n = 10) | 10.84 ± 5.22 (n = 10) |
| 7.5 | FLAPP + APPα | 362 ± 54 (n = 10) | 554 ± 77 (n = 10) | 409 ± 44 (n = 10) | 503 ± 80 (n = 10) |
| 7.5 | APPβ | 20 ± 58 (n = 10) | 168 ± 27 (n = 10) | 118 ± 21 (n = 10) | 57 ± 22 (n = 10) |
| 8 | Aβ | 4.42 ± 0.73 (n = 13) | 635.52 ± 302.45 (n = 13) | 128.68 ± 62.80 (n = 13) | 10.87 ± 3.39 (n = 13) |
| 8 | FLAPP + APPα | 386 ± 52 (n = 13) | 660 ± 102 (n = 13) | 494 ± 87 (n = 13) | 672 ± 150 (n = 13) |
| 8 | APPβ | 64 ± 77 (n = 13) | 174 ± 27 (n = 13) | 102 ± 26 (n = 13) | 57 ± 30 (n = 13) |
| 8.5 | Aβ | 5.54 ± 1.11 (n = 10) | 633.11 ± 363.14 (n = 10) | 118.39 ± 59.91 (n = 10) | 13.96 ± 7.34 (n = 10) |
| 8.5 | FLAPP + | 439 ± 79 | 764 ± 114 | 558 ± 80 | 750 ± 132 |

TABLE 5-continued

PDAPP Transgene Cohort Animal Data
Total Aβ & APP Measures in pmoles/gram of Brain Tissue.

| AGE IN MONTHS | Aβ & APP FORM | CEREBELLUM | HIPPOCAMPUS | CORTEX | THALAMUS |
|---|---|---|---|---|---|
|  | APPα | (n = 10) | (n = 10) | (n = 10) | (n = 10) |
| 8.5 | APPβ | 28 ± 59 | 185 ± 34 | 108 ± 42 | 47 ± 28 |
|  |  | (n = 10) | (n = 10) | (n = 10) | (n = 10) |
| 9 | Aβ | 5.52 ± 1.11 | 1512.39 ± 624.286 | 254.83 ± 105.927 | 19.46 ± 8.99 |
|  |  | (n = 10) | (n = 10) | (n = 10) | (n = 10) |
| 9 | FLAPP + APPα | 500 ± 112 | 763 ± 125 | 549 ± 78 | 815 ± 167 |
|  |  | (n = 10) | (n = 10) | (n = 10) | (n = 10) |
| 9 | APPβ | 4 ± 83 | 169 ± 25 | 121 ± 32 | 49 ± 26 |
|  |  | (n = 10) | (n = 10) | (n = 10) | (n = 10) |
| 10 | Aβ | 4.04 ± 1.02 | 2182.21 ± 1194.49 | 343.49 ± 165.531 | 15.46 ± 13.38 |
|  |  | (n = 11) | (n = 11) | (n = 11) | (n = 11) |
| 10 | FLAPP + APPα | 452 ± 130 | 678 ± 93 | 491 ± 102 | 693 ± 166 |
|  |  | (n = 11) | (n = 11) | (n = 11) | (n = 11) |
| 10 | APPβ | 52 ± 32 | 159 ± 22 | 87 ± 15 | 46 ± 10 |
|  |  | (n = 11) | (n = 11) | (n = 11) | (n = 11) |
| 12 | Aβ | 3.26 ± 0.35 | 4356.23 ± 1666.44 | 691.17 ± 360.93 | 18.08 ± 13.50 |
|  |  | (n = 9) | (n = 9) | (n = 9) | (n = 9) |
| 12 | FLAPP + APPα | 385 ± 166 | 638 ± 272 | 444 ± 171 | 708 ± 278 |
|  |  | (n = 10) | (n = 10) | (n = 10) | (n = 10) |
| 12 | APPβ | 41 ± 29 | 134 ± 47 | 76 ± 31 | 35 ± 19 |
|  |  | (n = 10) | (n = 10) | (n = 10) | (n = 10) |

ND = not determined

In contrast to APP levels, Aβ levels increased dramatically with age in the hippocampus and cortex. However, no such increase was noted in the cerebellum of the PDAPP transgenic mice, and only a moderate increase was seen in thalamus (Table 5). The increase of Aβ is greater in the hippocampus relative to the cortex, which also correlates with the 3D6 immunohistochemical results (see discussion below). Compared to the cortex levels of 4 month old mice, Aβ levels increase 10-fold by 8 months of age and 41-fold at 12 months old (660±380 pmoles Aβ/gram tissue at age 12 months). The corresponding increases in Aβ observed in hippocampus are even more impressive, as the 8 month value is 15 times that at 4 months old and increases to 106-fold at 12 months old (4,040±1750 pmoles Aβ/g tissue at 12 months). At 12 months of age, Aβ constitutes approximately 1% of protein in hippocampus of the PDAPP mice.

To see if the dramatic rise in brain Aβ concentration is due to amyloid deposition, we next visualized Aβ deposits immunohistochemically, using the opposite hemisphere of the same mice used for Aβ measurements. Notably, a parallel increase in Aβ plaque burden and Aβ level exists. These findings strongly argue that the rise in brain Aβ concentration determined by ELISA is due to the age-dependent amyloidosis.

3. $A\beta_{1-42}$ Measures in Transgenic Mouse Brain.

Concentrations of $A\beta_{1-42}$ in the cortex of transgenic mice were evaluated at different ages. As shown in Table 6, the percentage of Aβ which is $A\beta_{1-42}$ in the cortex of transgenic mice, also increases with age. The ELISA data suggest that $A\beta_{1-42}$ is preferentially depositing in the transgenic mice, and that the deposits detected by mAb 3D6 immunostaining are primarily $A\beta_{1-42}$.

TABLE 6

$A\beta_{1-42}$ Levels in the Cortex of Transgenic Brain.

| Age (months) | $A\beta_{1-42}$ (pmoles/g) |
|---|---|
| 4 | 4.71 |
| 8 | 75.65 |
| 10 | 247.43 |
| 12 | 614.53 |

4. Aβ Immunostaining in PDAPP Transgenic Brain.

Transgenic animals with Aβ values representing the mean Aβ value of the age group were used for 3D6 immunostaining. A progression of Aβ deposition is seen in the 4, 8, 10, and 12 months old animals. At four months of age, transgenic brains contained small, rare punctate deposits, 20 μm in diameter, that were only infrequently observed in the hippocampus and frontal and cingulate cortex. By eight months of age, these regions contained a number of thioflavin-positive Aβ aggregates that formed plaques as large as 150 μm in diameter. At ten months of age, many large Aβ deposits were found throughout the frontal and cingulate cortex, and the molecular layers of the hippocampus. The outer molecular layer of the dentate gyrus receiving perforant pathway afferents from the entorhinal cortex was clearly delineated by Aβ deposition. This general pattern was more pronounced by heavier Aβ deposition at one year of age. The anatomical localization of Aβ deposition is remarkably similar to that seen in Alzheimer's disease.

C. Discussion.

Aβ amyloidosis is an established diagnostic criteria of Alzheimer's disease (Mirra et al., *Neurology* 41:479–486 (1991)) and is consistently seen in higher cortical areas as well as the hippocampal formation of the brain in affected subjects. It is believed that Aβ amyloidosis is a relatively early event in the pathogenesis of AD that subsequently leads to neuronal dysfunction and dementia through a complex cascade of events (Mann et al., *Neurodegeneration* 1:201–215 (1992); Morris et al., *Neurology* 46:707–719

(1996)). Various pathways of APP processing have been described (reviewed in Schenk et al., *J. Med. Chem.* 38:4141–4154 (1995)) including the major a-secretase pathway where cleavage of APP occurs with Aβ (Esch et al.) and the amyloidogenic or β-secretase pathway where cleavage of APP occurs at the N-terminus of Aβ (Seubert et al. (1993)). Further cleavage of APP leads to the constitutive production of Aβ forms including those ending at position 40 ($A\beta_{1-40}$) or 42 ($A\beta_{1-42}$). ELISAs that detect specific APP products arising from these individual pathways in the PDAPP mouse brain allow determination of whether differential processing of APP contributes to the regional or temporal specificity of amyloid formation and deposition.

Aβ amyloid deposition seen in the PDAPP mouse brain is highly age and region specific. Amyloid deposition begins at around 7 months of age, and by 12 months of age, amyloid deposition is very profound throughout the hippocampus and in the rostral region of the cortex. The age dependent increases in amyloid deposition correlate well with the dramatic rise in Aβ levels in these brain regions as measured by ELISA assay. An increase in Aβ is measurable by 7 months of age and by 10 months the hippocampus as 2180 pmoles/g of Aβ, a concentration equivalent to that of my cytoskeletal proteins and comparable to the levels found in the cortex of human AD brain (Gravina et al., *J. Biol. Chem.* 270:7013–7016 (1995)). Aβ levels in the cerebellum, an unaffected brain region, still are at 4 pmoles/g—essentially unchanged relative to the levels at 4 months of age—again correlating with amyloid deposition measured by histological analyses. These results indicate that in aged PDAPP mice, brain Aβ levels reflects amyloid burden and therefore direct immunoassay measurement of brain Aβ levels can be used to test for compounds that reduce amyloid plaque burden.

In the PDAPP mouse, individuals suffering Down's Syndrome, and individuals with certain forms of FAD, overproduction of Aβ is almost certainly an accelerating factor not only in Aβ deposition but in subsequent neuropathology (Citron et al., Mann et al., Miller et al., *Archives of Biochem. Biophys.* 301:41–52 (1993)). A comparison of the Aβ measurements seen in the PDAPP mouse with those reported for AD brain tissue reveals several striking similarities. For example, in the PDAPP mouse, the relative levels of Aβ peptide in hippocampus from young (2 months of age) versus old (10 months of age) mice is nearly a hundred fold. Similar findings were noted by Gravina et al. in comparing control brain tissue relative to that of AD. The rise in brain Aβ levels in the PDAPP mouse is rather pronounced between the ages of six to nine months of age. Again, this timecourse parallels, in an accelerated manner, that seen in Down's Syndrome brain tissue, where amyloid deposition begins at approximately 30 years of age and increases substantially until approximately age 60 (Mann).

In summary, the above results show that a reproducible increase in measurable Aβ occurs in the brain tissue of the PDAPP mice and that this increase correlates with the severity of amyloid deposition. These findings indicate that these mice can be used to identify agents or compounds that pharmacologically reduce Aβ peptide production or affect its deposition.

EXAMPLE 9

Behavioral Differences in PDAPP Transgenic Mice.

Alzheimer's disease is characterized by cognitive deficits including memory loss, and impairment of memory functions. To determine if the disclosed transgenic mice exhibit similar deficits, transgenic (TG) and non-transgenic (nTG) mice were evaluated for task performance in three types of maze apparatus used to test working and reference memory; the Y maze, the radial arm maze (RAM), and the water maze. The transgenic mice tested represent the fifth generation derived from the PDAPP mice described in Example 6. The Y maze and the radial arm maze are used to assess spontaneous alternation which is a function of working memory. For the Y maze task, the mouse is placed in the stem of a Y maze twice, each time allowing a choice entry into one of the arms. Entering both arms is a successful alternation, requiring memory of the previously entered arm, while entering the same arm on both trials is a failure. Chance performance is 50% alternation, that is, 50% of the mice alternate.

For the radial arm maze task, the mouse is placed at the center of a maze with multiple arms radiating from the center. In the testing described below, a radial eight-arm maze was used. Alternation performance is measured by allowing only eight entries, with the number of different arms entered being the measure of performance. The number of different-arm entries can be compared to the number of different-arm entries expected by chance, which is 5.25 (Spetch and Wilkie, "A program that stimulates random choices in radial arm mazes and similar choice situations" *Behavior Research Methods & Instrumentation* 12:377–378 (1980)). Performance above chance, that is, above 5.25, requires memory of the previously entered arms.

The water maze used for the tests described below consists of a pool of water in which a submerged platform is placed. This hidden platform (HP) can be found by swimming mice either by chance (first trial) or through memory of positional clues visible from the tank (subsequent trials). Subject mice were trained in the hidden platform task according to standard procedures. Briefly, mice were first pretrained in a small pool (47 cm diameter, 20 cm platform), which teaches them how to navigate in water, that the platform is the goal, that there is no other escape, and that to find it they must resist their natural inclination to stay along the sides of the pool. They were then trained to find a single platform position in the hidden platform task using a larger pool and smaller platform (71 cm pool, 9 cm platform).

During the HP task, visual cues were located inside the pool (intramaze cues; black pieces of cardboard—circle, plus, or horizontal lines—located in three quadrants at the top of the wall, which was 38 cm high above water level), and various room cues were visible outside the pool (extramaze cues).

The mice assigned to the characterization cohort study were tested on the behavioral tasks described above over 3 days during the week or two before euthanasia. Their transgenic status was not known to the tester. Non-transgenic littermates were used for comparison. Each morning the subject mice were run in the Y maze and RAM as described above. They were then tested for general strength on the inclined plane (INP) test. For this, mice were placed in a 10-cm-wide runway lined with ridged plastic and elevated with the head up at 35°. The angle was then increased until the mouse slid off, and the angle was recorded. This was repeated three times each day. The average scores for the three days were calculated for each mouse for the Y maze (0=repeat, 1=alternate), RAM (number of different arms and time to finish, 10 minute limit), and INP (average of all nine trials). General activity was also rated on the first day of testing. Each mouse was observed in the cage, and picked up and held. A mouse that remained calmly in the hand was scored 1, with progressively greater activity and reaction to handling scored up to 4.

Following the above tests each day, mice were tested in the water maze as described above. Briefly, mice were pretrained in a small pool to climb on a large submerged platform as their only means of escape from the water. They were then given six blocks of four trials each to learn the location of a small platform in a large pool. For analysis, all four trials within each block were averaged. The exception was the first hidden platform block, for which only the last three trials were averaged. The first trial was analyzed separately, because it is the only one for which platform location could not be known, and thus did not relate to spatial learning. It is thus used as a control for non-spatial factors, such as motivation and swimming speed. The performance effects between blocks were analyzed as a repeated measure for the hidden platform task. Standard analysis of variance (ANOVA) calculations were used to assess the significance of the results.

Results in the RAM show that TG performed significantly worse than nTG across all ages (Group effect: p=0.00006). The time to finish was also significantly different between TG and nTG mice (Group effect: p=0.005). The correlation between the time to finish and the number of arms chosen was small (R=−0.15, p=0.245 in each group). This suggests that the consistent impairment in the RAM is not accounted for by the increased time to complete the task taken by TG mice. Results in the Y maze were also significantly different for TG and nTG mice (Group effect: p=0.011). Validation studies performed on non-transgenic mice indicate that the Y maze is a less sensitive measure than the RAM.

Measures of strength (INP) and activity indicate no differences between TG and nTG mice. These are considered very rough measures, with only large differences being detectable. There was, however, a decrease in the activity score for all mice over time (Age effect: p=0.070). There was a difference in body weight, with TG weighing 8% less than controls (Group effect: p=0.0003), primarily in female TG mice. However, this does not seem to have an effect on the results, as shown by the lack of any difference in strength (see above) or swimming speed (see below) between TG and nTG mice.

Results of the hidden platform task, considered here a test of reference memory, show a consistent difference between TG and nTG mice. ANOVA reveals that the effects of transgenic status (Group effect: p=0.00016) and trial blocks (Block effect: p<0.00001) are significant. The effect of transgenic status on performance is accounted for by slower performance by TG mice across all trial blocks and ages. Analysis of Trial 1 reveals an effect of transgenic status (Group effect: p=0.018), suggesting a difference in performance before learning has occurred. However, an analysis of covariance, with trial 1 as the covariate, still yields a significant deficit in TG mice (p=0.00051).

It was also possible that some physical differences between TG and nTG mice, rather than cognitive differences, could have been responsible for some of the performance differences seen in the water maze tasks. However, no significant difference in strength or activity was observed (see above). Another possibility considered was the effect of swimming speed on performance since a slower swimmer with equivalent cognitive ability would take longer to reach the platform. To test this, video tracking was used in the hidden platform task to measure the distance travelled to reach the platform (a measure of the amount of searching done by the mice which is related to cognitive ability), the swimming speed (a measure of physical ability unrelated to cognitive ability), and the amount of time need to find the platform (a measure of the combination of both the distance travelled and the swimming speed). This was done in older and younger mice than reported above, using three trials per block and no pretraining. The time needed to find the platform was significantly different in TG and nTG mice (Group effect: p<0.0005), with the TG mice taking longer. However, the swimming speed was not significantly different between TG and nTG mice (Group effect: p=0.879). Thus, the difference in time needed to find the platform is likely to be due to a cognitive difference between TG and nTG mice. This is confirmed by measures of the distance travelled to find the platform. The TG mice travelled significantly further than the nTG mice before reaching the platform (Group effect: p<0.0005). These results indicate that the differences seen between TG and nTG mice in the time to reach the platform in the water maze tasks are due to differences in cognitive ability.

To test whether nTG mice retain a better memory of the platform location than TG mice, a probe trial was given immediately following hidden platform training in which the platform was removed. Video tracking was used to determine the number of crossings of the former platform location made by the mice relative to crossings of non-platform locations. There was a significant difference seen between the relative crossings of TG and nTG mice (Group effect: p=0.006). This is evidence that the nTG mice remember the former location of the platform better than TG mice.

It was also possible that the difference observed between TG and nTG mice in the time needed to reach the platform could have been influenced by differences in perception of the cues or motivational differences. To test this, TG and nTG mice were subjected to visible platform tasks in the water maze. For these tasks, a platform was placed in the pool so that it was visible above the water. Three different platforms were tested, a dark platform 25 mm above the surface (most visible), a gray platform 25 mm above the surface, and a dark platform 5 mm above the surface (both less visible). The results show no difference in the time to find the most visible platform between TG and nTG mice (Group effect: p=0.403). There was not any greater decrease in performance in TG mice when less visible platforms were used, suggesting that their vision was as good as nTG mice. These results indicate that perceptual and motivational differences do not influence the time to reach the platform in the water maze tasks described above.

Performance differences between TG and nTG mice were shown for RAM, Y maze, and water maze cognitive tasks in mice aged 4 to 8 months (2 to 12 months for the water maze). All of these differences indicate, and are consistent with, cognitive deficits in the transgenic mice as a group. The various tasks combined to test working memory and reference memory, both of which are implicated in cognitive impairment observed in Alzheimer's victims.

EXAMPLE 10

Detection and Measurement of Alzheimer's Disease Markers.

A. Detection and Measurement of GFAP.

Glial fibrillary acidic protein (GFAP), a marker which increases in AD brain tissue, was measured in the following manner. Tissue extracts were prepared from hippocampi of control and PDAPP transgenic mice, as described in Example 6, aged 14 months. Tissue was sonicated in 10 volumes (v/w) of 10 mM Tris, pH 7.5, 1 mM EDTA, 1 mM EGTA, 0.1 mM PMSF, 10 μg/ml leupeptin, 5 μg/ml calpain inhibitor 1. Protein determinations were made on the extract and SDS-PAGE sample buffer added before boiling the samples for 5 minutes. SDS-PAGE was performed using 12.5 μg of protein of each sample loaded onto 10% Tris-glycine gels (Novex). The proteins were transferred to Pro-Blot PVDF membranes by standard methods. GFAP immunoreactive proteins were detected using an anti-GFAP antibody from Sigma (G9269) used at a dilution of 1:2,000. An increase in immunoreactivity in general was observed, and a smaller anti-GFAP reactive species was also found to increase substantially, in the transgenic animals. In non-transgenic animals, this approximately 40 kD fragment gave a mean densitometer signal of 142.47, while in the transgenic animals, it gave a mean densitometer signal of 591.51. This difference was significant, with a P value of 0.0286.

B. Detection of Gliosis.

Gliosis is one of the changes that is associated with the neuropathology of Alzheimer's disease. The isoquinoline carboxamide PK 11195 has been shown to be a preferential marker of the peripheral benzodiazepine sites associated with gliosis. These sites have been shown to be enhanced in several diseases and animal models associated with neuronal damage and activated necroglia including stroke (Stephenson et al., J. Neuroscience 15:5263–5274 (1991)) and Alzheimer's disease (Diorio et al., Neurobiology of Aging 12:255–258 (1991)). In particular Diorio and colleagues have shown an approximate 200% increase in [$^3$H] PK 11195 binding in some brain regions of AD patients, such as the temporal cortex compared with age-matched controls. In this example, the brains from the PDAPP mouse, described in Example 6, were examined for qualitative and quantitative changes in the binding of [$^3$H] PK 11195 in order to correlate with the previously described AD disease pathology. Two different approaches were utilized; radioreceptor binding to homogenates of different brain regions and receptor autoradiography.

1. Methods.

For the homogenate binding studies, PDAPP mice were euthanised by cervical dislocation and the brains rapidly dissected on ice. Homogenates (10 mg/ml wet weight) of cerebral cortex, hippocampus and cerebellum were prepared in 50 mM Tris HCl, pH 7.4. 0.3, 1.0 and 3.0 nM [$^3$H] PK 11195 was incubated with these brain regions for 60 minutes at 23° C. followed by rapid filtration over Whatman GF/B filters using a Brandell cell harvester. Non-specific binding was determined using 1 μM unlabelled PK 11195. Quantitation was performed by liquid scintillation spectrometry.

In the autoradiographic studies, PDAPP mice were euthanised using carbon dioxide, the brains removed and snap frozen in methyl butane/dry ice. The brains were sectioned in the coronal plane through the hippocampus. Twenty micron thick sections were mounted on glass slides and stored at −20° C. Sections were incubated at 1 hour at 23° C. in 170 mM Tris-HCl, pH 7.4 containing 1 nM [$^3$H] PK 11195. Non-specific binding was determined using 1 μM unlabelled PK 11195. Incubations were terminated by rinsing sections twice for 5 minutes in ice-cold incubation buffer followed by a brief wash in ice-cold distilled water. Following rapid drying, sections were exposed to tritium Hyperfilm (Amersham International) for up to 5 weeks.

2. Results.

Four heterozygous transgenic mice 3–4 months of age were evaluated in the homogenate binding studies and compared with litter-mate controls. No significant differences were observed between any of the brain regions of the transgenic animals and their respective controls. [$^3$H] PK 1119 autoradiography was performed to compare binding in a 12-month old heterozygotic transgenic mouse with an aged-matched non-transgenic control. Preliminary results from an autoradiogram exposed for five weeks indicated that several plaque-like structures were labeled in the retrosplenial cortex of the transgenic mouse, a region that invariably contains Aβ deposits. The pattern of labeling corresponded to microglial cell or astrocytic clumps associated with plaques, rather than the more widespread pattern of astrocytosis or microgliosis in the hippocampal and cortical parenchyma. The non-transgenic mouse did not show this labeling pattern.

No changes were observed in the 3–4 month animals but some evidence for an increase in [$^3$H] PK 11195 binding was seen in the 12-month animal.

C. Detection and Measurement of Cholinergic Nerve Terminals.

A population of cholinergic neurones projecting to the forebrain have been shown to be selectively decreased in the postmortem brains of patients diagnosed with Alzheimer's disease. Hemicholinium-3 is a potent inhibitor of high affinity choline uptake and has been shown to be a good marker of cholinergic nerve terminals (Pascual et al., J Neurochem 54:792–800 (1990)). The total number of high affinity choline uptake sites in PDAPP transgenic animals, which are described in Example 6, has been measured using both crude whole-brain preparations and homogenates from selective brain regions using the selective ligand [$^3$H]-Hemicholinium-3 ([$^3$H]HCh-3). [$^3$H]-Hemicholinium-3 binding was determined using a modification of the methods described in Pascual et al. Mice were euthanised by asphyxiation with carbon dioxide and the brains rapidly removed and dissected on ice. The cortex, cerebellum, striatum and hippocampus were homogenized in 5 ml of 10 mM phosphate buffer without NaCl. Samples were spun at 17,000× g for 10 minutes, and the pellets washed twice in 5 ml 10 mM $PO_4$ buffer. The final pellet was resuspended in 5 ml 1× phosphate buffered saline (PBS) to produce a protein concentration of 0.5 mg/ml. Brain regions were assayed in triplicate for high affinity choline uptake sites by the addition of [$^3$H]HCh-3 (3 nM final concentration). Following a 20 minute incubation, assays were terminated by rapid filtration through Whatman GF/B filters using a Brandell cell harvester and washing with PBS. Filters were transferred into scintillation vials, and specific binding estimated by liquid scintillation spectrometry.

D. Detection and Measurement of Sodium-Potassium ATPase.

Ouabain has been shown to bind specifically to high affinity sites in mammalian brain and that these sites correspond to a neuronal form of sodium-potassium ATPase (Na/K-ATPase; Hauger et al., J Neurochem 44:1709–1715 (1985)). These sites have been shown to decrease in animal models of neurodegenerative diseases. Alzheimer's disease is characterized by massive neurodegeneration (DeLacoste and White, Neurobiology of Aging 4(1):1–16 (1993)).

In order to estimate the extent of neurodegeneration in the PDAPP mouse the binding of ouabain was determined in mouse brain homogenates. Methods were adapted from those described by Hauger et al. Brain tissue was homogenized in 100 mM Tris HCl, pH 7.4 containing 200 mM NaCl and 10 mM $MgCl_2$ and resuspended in assay buffer to produce a final concentration of 100 μg protein per assay.

Specific binding was determined with 1 to 200 nM [$^3$H] ouabain in a solution of 5 mM ATP, 100 mM Tris HCl, pH 7.4, 10 mM MgCl$_2$, and 200 mM NaCl, incubated for 30 minutes at 37° C. Non specific binding was determined in the presence of 100 mM ouabain and the absence of ATP. Assays were terminated by rapid filtration over Whatman GF/B filters. Tubes were washed with ice cold 50 mM Tris HCl, pH 7.4, 15 mM KCl, 5 mM MgCl$_2$. Filters were transferred into scintillation vials, and specific binding estimated by liquid scintillation spectrometry.

Measurements of Na/K-ATPase and Mg-ATPase activity in brain tissue of PDAPP transgenic mice of various ages and in non-transgenic control brain tissue. These results show some significant differences in activity between transgenic and non-transgenic samples in older mice. Mouse brain homogenates from 4, 8, and 12 month old PDAPP transgenic (TG) mice, and from non-transgenic (nTG) mice, were prepared and assayed generally as described above. The activity of Mg-ATPase was also determined. The results are shown in Tables 7 and 8.

TABLE 7

Na/K-ATPase Activity in PDAPP Transgenic Mouse Brain.

| | | Na/K-ATPase | |
|---|---|---|---|
| Age | Tissue | rate (pmole Pi/mg protein/min) | % of nTG |
| 4 | TG hippocampus | 2.57 ± 0.62 | 88 ± 14 |
| 4 | nTG hippocampus | 2.53 ± 0.51 | — |
| 4 | TG cortex | 0.57 ± 0.13 | 72 ± 9 |
| 4 | nTG cortex | 0.77 ± 0.17 | — |
| 4 | TG cerebellum | 1.39 ± 0.17 | 85 ± 14 |
| 4 | nTG cerebellum | 2.14 ± 0.53 | — |
| 8 | TG hippocampus | 4.63 ± 1.72 | 153 ± 53 |
| 8 | nTG hippocampus | 2.87 ± 0.41 | — |
| 8 | TG cortex | 1.16 ± 0.08 | 121 ± 23 |
| 8 | nTG cortex | 1.15 ± 0.20 | — |
| 8 | TG cerebellum | 2.74 ± 0.81 | 183 ± 53 |
| 8 | nTG cerebellum | 1.47 ± 0.13 | — |
| 12 | TG hippocampus | 1.66 ± 0.36 | 58 ± 9 |
| 12 | nTG hippocampus | 3.11 ± 0.94 | — |
| 12 | TG cortex | 1.45 ± 0.40 | 109 ± 17 |
| 12 | nTG cortex | 1.60 ± 0.46 | — |
| 12 | TG cerebellum | 1.43 ± 0.32 | 74 ± 7 |
| 12 | nTG cerebellum | 2.04 ± 0.64 | — |

TABLE 8

Mg-ATPase Activity in PDAPP Transgenic Mouse Brain.

| | | Mg-ATPase | |
|---|---|---|---|
| Age | Tissue | rate (pmole Pi/mg protein/min) | % of nTG |
| 4 | TG hippocampus | 2.83 ± 0.38 | 110 ± 14 |
| 4 | nTG hippocampus | 2.44 ± 0.54 | — |
| 4 | TG cortex | 1.74 ± 0.14 | 92 ± 5 |
| 4 | nTG cortex | 1.87 ± 0.18 | — |
| 4 | TG cerebellum | 2.58 ± 0.44 | 100 ± 12 |
| 4 | nTG cerebellum | 2.59 ± 0.35 | — |
| 8 | TG hippocampus | 3.28 ± 0.69 | 99 ± 22 |
| 8 | nTG hippocampus | 3.32 ± 0.39 | — |
| 8 | TG cortex | 1.72 ± 0.11 | 73 ± 6 |
| 8 | nTG cortex | 2.40 ± 0.31 | — |
| 8 | TG cerebellum | 3.19 ± 0.49 | 113 ± 15 |
| 8 | nTG cerebellum | 2.77 ± 0.23 | — |
| 12 | TG hippocampus | 1.48 ± 0.21 | 65 ± 7 |
| 12 | nTG hippocampus | 2.33 ± 0.46 | — |
| 12 | TG cortex | 1.60 ± 0.30 | 76 ± 7 |
| 12 | nTG cortex | 2.06 ± 0.40 | — |
| 12 | TG cerebellum | 1.61 ± 0.26 | 78 ± 8 |
| 12 | nTG cerebellum | 1.93 ± 0.99 | — |

The difference in Na/K-ATPase activity between transgenic and non-transgenic tissue is significant (p<0.05) in the case of 12 month old cerebellum, and is highly significant (p<0.01) in the case of 12 month old hippocampus. The difference in Mg-ATPase activity between transgenic and non-transgenic tissue is significant (p<0.05) in the case of 8 and 12 month old cortex, and is highly significant (p<0.01) in the case of 12 month old hippocampus.

E. In situ Hybridization With Probes to Neurotrophic Factors.

The use of in situ hybridization to detect and localize mRNAs for specific gene products is well documented in the literature (Lewis et al., *Molecular Imaging in Neuroscience: A Practical Approach* (New York, Oxford University Press. 1st ed., 1–21, 1993), Lu and Gillett, *Cell Vision* 1(2) :169–176 (1994), Sirinathsinghji and Dunnett, *Molecular Imaging in Neuroscience: A Practical Approach* (New York, Oxford University Press. 1st., ed. 43–67, 1993), Lawerence and Singer, *Nuc. Acids Res.* 13:1777–1799 (1985), Zeller and Rogers, *Current Protocols in Molecular Biology* (New York, John Wiley and Sons. 14.3.1–14.5.5, 1995)). For illustrative purposes, the specific example described below utilizes $^{35}$S-radiolabeled oligodeoxyribonucleotide probes to detect BDNF mRNA in cryostat sectioned mouse brain from the PDAPP transgenic mouse described in Example 6 and non-transgenic control mice. However, $^{33}$P-labeled radioactive DNA probes, as well as in vitro transcribed complementary RNA probes, could be used as well. Non radioactive probe labeling methods may also be used (Knoll, *Current Protocols in Molecular Biology* (New York, John Wiley and Sons. 14.7.1–14.7.14, 1995)). Additionally, the choice of tissue pre-treatment for hybridization with probe (for example, paraffin embedded sections) and post-hybridization washes depend on the method used, examples of which are described in the references cited above. Known and appropriate precautions against RNase contamination should be employed and are also discussed in the above references.

1. Tissue Preparation.

Freshly dissected whole brains, or sub-regions of interest, from transgenic or control mice at various developmental stages, or post-natal ages, are snap frozen in isopentane pre-equilibrated to −70° C. If desired, the animals may be perfused with PBS to eliminate circulating cells from brain prior to dissection. The brains are removed following 15 to 20 seconds immersion in isopentane, wrapped in aluminum foil, labeled appropriately, and stored at −80° C. for sectioning. It should be noted that although the signal from in situ hybridization to cryostat sectioned tissues is more sensitive than to paraffin embedded sections, it is dependent upon the time from dissection to hybridization. Frozen tissue is preferably analyzed by hybridization with probe within six weeks. RNA integrity in tissues declines beyond this time. Thus, if longer time periods between dissection and analysis are anticipated, the tissue should be fixed (see, for example, Lu and Gillett) before long term storage at −80° C.

Prior to sectioning, Probe-On-Plus glass slides (Fisher Scientific, Pittsburgh, Pa.) can be made RNAase free by overnight soaking in absolute ethanol, air dried briefly in a dust free environment, and baked at 180° C. for a minimum of 4 hours. After cooling to room temperature, the slides are coated with 0.01% poly-lysine (prepared in DEPC treated $H_2O$) for approximately 5 seconds, and air dried in a dust free area. The coated slides can be stored for up to one month before use in a slide box with silica gel or drierite pellets.

For sectioning, the frozen brain stored at −80° C. is transferred to a cryostat at −20° C., mounted onto a sectioning block, embedded in OCT.®, and allowed to equilibrate. The tissue is then cut into 7 to 14 μm thick sections using a sterilized microtome knife (treated with 70% EtOH in DEPC $H_2O$), and thaw mounted onto poly-lysine coated slides. The slides are kept at −20° C. until the sectioning is complete. The sections are fixed and dehydrated by immersing the slides sequentially in the solutions noted below.

1. once in 4% paraformaldehyde, 1X PBS, pH 7.4, at 0° C. for 5 minutes (this solution should be made fresh, and can be stored for up to 1 week at 4° C.);
2. twice in 1X PBS, 2.5 minutes each time;
3. once in 50% EtOH in DEPC $H_2O$ for 5 minutes;
4. once in 70% EtOH in DEPC $H_2O$ for 5 minutes;
5. once in 95% EtOH in DEPC $H_2O$ for 5 minutes;

The fixed sections are stored immersed in the 95% EtOH/DEPC $H_2O$ solution at 4° C. until use. If the sections are not fixed immediately, they may be stored at −80° C. in the presence of drierite until use. In this case the sections are allowed to equilibrate to room temperature prior to the fixation/dehydration steps.

2. Probe Design and Preparation.

The sequence of the mouse BDNF mRNA/cDNA (accession #55573) is available from the Genbank database of Nucleic acid sequences (NCBI, Bethesda, Md.). Antisense oligodeoxynucleotide probes against BDNF were designed using the primer select module of the DNAstar™ software package (Lasergene Inc., Madison, Wis.). Numerous other software packages, such Oligo® (NBI, Plymouth, Minn.), offer similar capabilities, and are also suitable. Candidate probes of 45 to 55 nucleotides length, approximately 50% G+C content, and hybridizing to the pre-cursor or mature peptide encoding regions of the BDNF mRNA were synthesized on an ABI 380B DNA synthesizer. As specificity controls, sense oligonucleotides corresponding to each probe were also synthesized. Using the convention that the first nucleotide in the BDNF coding region is position 1, the BDNF probes synthesized correspond to BDNF nucleotide positions 47 to 94 (probes 2710 & 2711), 158 to 203 (probes 2712 & 2713), 576 to 624 (probes 2714 & 2715), and 644 to 692 (probes 2716 & 2717). The even numbered oligonucleotides are probes for the sense strand, and the odd numbered oligonucleotides are probes for the anti-sense strand.

For radiolabeling, the probes are gel purified on denaturing acrylamide gels and reconstituted in $H_2O$ using standard protocols (Sambrook et al.). The probes (30 to 35 ng, 2 pmoles) are labeled by 3' homopolymeric tailing using terminal deoxynucleotidyl transferase (Promega, Madison Wis.) and $^{35}$S-dATP (1000 Ci/mmol, Amersham Inc.) according to the enzyme manufacturer's recommendation. The radiolabeled probes are purified by column chromatography on size exclusion mini-spin columns (Biospin-6, Biorad Inc., Hercules, Calif.). The specific activity of the probes is quantitated by scintillation counting. Typical specific activities of the probes ranged from $1\times10^9$ to $5\times10^9$ cpm/μg.

3. Tissue Hybridization and Post Hybridization Washes.

In preparation for hybridization, the desired number of slides are removed from storage under alcohol, and allowed to air dry thoroughly in the slide rack (approximately 1 hour). Meanwhile, the probe is heat denatured in a boiling $H_2O$ bath for 2 to 5 minutes, quick chilled in an ice/$H_2O$ bath, and diluted in hybridization buffer (10% dextran sulfate, 50% deionized formamide, 4× SSC, 5× Dehardts, 100 μg/ml sheared salmon sperm DNA, 100 μg/ml polyadenylic acid) to a final concentration of $5\times10^3$ to $10\times10^3$ cpm/μl. DTT is added to a 10 mM final concentration.

For hybridization, 100 μl of diluted probe in hybridization buffer (corresponding to $0.5\times10^6$ to $1.0\times10^6$ cpm probe) is carefully applied to each section being hybridized with probe. The solution is gently spread over the section with a pipet tip to cover the entire section(s) on each slide. The slides containing probe are then placed in humidified hybridization chambers at 42° C. for hybridization overnight with the probe. The hybridization chambers can be covered utility boxes, or acrylic boxes, with raised platforms to accommodate slides. The boxes are lined with filter paper (or paper towels), saturated in 4× SSC, 50% formamide, and humidified by pre-incubating them with closed lids in a 42° C. incubator for 1 to 3 hours before the slides are placed inside them. Although cover slips can be placed on the sections after the hybridization buffer is applied, this is not necessary provided the hybridization chambers are adequately humidified during the procedure. If pre-hybridization is used to obtain a lower background, the sections may be incubated at 42° C. under 50 μl hybridization buffer (minus probe) per section for 1 to 2 hours. After this time, an equal volume of hybridization buffer containing probe at twice the concentration described above is applied to each section, and hybridization is carried out as described above.

For washes, the slides are transferred from the hybridization chamber to a slide holder. The slides can be placed in the slide holder every 4th or 5th slot so as to allow adequate flow of wash solution over the surface of each section. This placement can significantly lowers background on the sections. A moderate flow rate of wash solution over the surface of the sections promotes removal of unhybridized probe, and consequently reduces background. This is best accomplished during the 55° C. wash steps by suspending the slides in the slide holder, above a magnetic stir bar. The stir bar is preferably placed approximately one inch under the slide holder. This can be done by hanging the slide holder(s) from pipets straddling the wash chamber. A large beaker, or a 4 to 6 inch deep Pyrex baking dish makes a suitable wash chamber. The wash chamber is placed on a hot-plate stirrer, the temperature setting of which is precalibrated to maintain the wash solution at 55° C. during the procedure. The changes of wash solution are made using pre-equilibrated solution. Washes and post wash dehydration of the sections are carried out as follows:

1. twice in 1X SSC at room temperature for 5 minutes each time;
2. three times in 1X SSC at 55° C. for 30 minutes each time;
3. once in 1X SSC at room temperature for 1 min.
4. once in 0.1X SSC at room temperature for 15 seconds;
5. once in ultra pure H₂O at room temperature for 15 seconds;
6. once in 50% EtOH for 15 seconds;
7. once in 70% EtOH for 15 seconds;
8. once in 95% EtOH for 15 seconds;

The sections are air dried thoroughly at room temperature for 2 hours, followed by 30 minutes at 55° C. The dried sections on the slides are placed in autoradiographic cassette and exposed to X-ray film (Hyperfilm, β-max, Amersham Inc., Arlington Heights, Ill.) at 4° C. for 2 to 3 days to estimate the exposure time required under emulsion. The X-ray film is developed according to the manufacturers recommendation. The sections are coated with emulsion (Amersham LM-1, #RPN40) by dipping in emulsion at 42° C. under appropriate safelight conditions. The emulsion coated slides are air dried on a cooled surface for approximately 30 minutes, and transferred to a plastic slide box containing a drying agent (drierite pellets). The seams of the box can be sealed with black tape, and the box wrapped in several layers of aluminum foil to ensure a light-tight enclosure. Following 2 to 4 hours at room temperature to finish the drying, the boxes are transferred to 4° C. for autoradiographic exposure for 2 to 6 weeks. Prior to developing the emulsion coated slides, the box is removed from the refrigerator and allowed to equilibrate to room temperature for approximately 1 hour. The slides are then developed according to the manufacturers instructions, air dried for 1 to 2 hours, and if desired, counterstained with the appropriate counterstain.

Modifications and variations of the making and testing of transgenic animal models for testing of Alzheimer's disease will be obvious to those skilled in the art from the foregoing detailed description. Such modifications and variations are intended to come within the scope of the following claims.

We claim:

1. A method of selecting a transgenic mouse as a model of Alzheimer's disease, comprising
   providing a plurality of transgenic mice, each comprising a nucleic acid construct stably incorporated into the genome, wherein the construct comprises a promoter for expression of the construct in a mammalian cell and a region encoding an Au-containing protein, wherein the promoter is operatively linked to the region,
   wherein the region comprises DNA encoding the Aβ-containing protein, wherein the Aβ-containing protein consists of all or a contiguous portion of a protein selected from the group consisting of
   APP770 bearing a mutation in one or more of the amino acids selected from the a group consisting of amino acid 669, 670, 671, 690, 692, and 717, APP751 bearing a mutation in one or more of the amino acids selected from the group consisting of amino acid 669, 670, 671, 690, 692, and 717, and APP695 bearing a mutation in one or more of the amino acids selected from the group consisting of amino acid 669, 670, 671, 690, 692, and 717; a protein consisting of amino acids 672 to 770 of APP; and a protein consisting of amino acids 672 to 714 of APP;
   determining expression levels of APP, APPβ, APPα, and/or Aβ in each of the transgenic mice;
   identifying a transgenic mouse wherein Aβtot is expressed at a level of at least 30 nanograms per gram of brain tissue of the mouse when it is two to four months old, Aβ1–42 is expressed at a level of at least 8.5 nanograms per gram of brain tissue of the mouse when it is two to four months old, APP and APPα combined are expressed at a level of a least 150 picomoles per gram of brain tissue of the mouse when it is two to four months old, APPβ is expressed at a level of at least 40 picomoles per gram of brain tissue of the mouse when it is two to four months old, and/or mRNA encoding the Aβ-containing protein is expressed to a level at least twice that of mRNA encoding the cndogenous APP of the transgenic mouse in brain tissue of the mouse when it is two to four months old;
   using an offspring of the identified transgenic mouse as a model of Alzheimer's disease.

2. The method of claim 1, further comprising administering a compound to be tested to the offspring or cells drived therefrom, and
   detecting or measuring the Alzheimer's disease marker such that any difference between the marker in the transgenic mouse, or by cells derived from the transgenic mouse rodent, and the marker in a transgenic mouse to which the compound has not been administered, or by cells derived from the transgenic mouse to which the compound has not been administered, is observed,
   wherein an observed difference in the marker indicates that the compound has an effect on the marker.

3. The method of claim 2 wherein the Alzheimer's disease marker is a protein and the observed difference is an increase or decrease in the amount of the protein present in the transgemc mouse to which the compound has been administered, or by cells derived from the transgenic mouse to which the compound has been administered.

4. The method of claim 3 wherein the protein is selected from the group consisting of Cat D,B, Neuronal Thread Protein, nicotine receptors, 5-HT$_2$ receptor, NMDA receptor, α2-adrenergic receptor, synaptophysin, p65, glutamine synthetase, glucose transporter, PPI kinase, GAP43, cytochrome oxidase, heme oxygenase, calbindin, adenosine A1 receptors, choline acetyltransferase, acetylcholinesterase, glial fibrillary acidic protein (GFAP), α1-antitrypsin, C-reactive protein, α2-macroglobulin, IL-1α, IL-1β, TNFα, IL-6, HLA-DR, HLA-A, D,C, CR3 receptor, MHC I, MHC II, CD 31, CR4, CD45, CD64, CD4, spectrin, tau, ubiquitin, MAP-2, apolipoprotein E, nerve growth factor (NGF), brain-derived neurotrophic factor (BDNF), advanced glycosylation end products, receptor for advanced glycosylation end products, COX-2, CD18, C3, fibroblast growth factor, CD44, ICAM-1, lactotransferrin, C1q, C3d, C4d, C5b–9, gamma RI, Fc gamma RII, CD8, CD59, vitronectin, vitronectin receptor, beta-3 integrin, Apo J, clusterin, type 2 plasminogen activator inhibitor, midkine, macrophage colony stimulating factor receptor, MRP14, 27E10, interferon-alpha, S100β, cPLA$_2$, c-jun, c-fos, HSP27, HSP70, MAP5, membrane lipid peroxidase, protein carbonyl formation, junB, jund, fosB, fra1, cyclin D1, p53, NGFI-A, NGFI-B, IκB, NFκB, IL-8, MCP-1, MIP-1α, matrix metaloproteinases, 4-hydroxynonenal-protein conjugates, amyloid P component, laminin, and collagen type IV.

5. The method of claim 3 wherein the Alzheimer's disease marker is selected from the group consisting of Aβ$_{tot}$, Aβ$_{1–42}$, Aβ$_{1–40}$, Aβ$_{N3}$(pE), Aβ$_{X-42}$, Aβ$_{X-40}$, Aβ$_{Insoluble}$, Aβ$_{Soluble}$, full length APP, APPα, APPβ, FLAPP+ APPα, the last 100 amino acids of APP, and the last 57 to 60 amino acids of APP.

6. The method of claim 2 wherein the Aizheimer's disease marker is a protein and the observed difference is a reduction or absence of the protein in plaques or neuritic tissue present in the transgenic mouse to which the compound has been administered.

7. The method of claim 6 wherein the protein is selected from the group consisting of Cat D,B, protein kinase C, NADPH, C3d, C1q, C5, C4bp, C5a-C9, tau, ubiquitin, MAP-2, neurofilaments, heparin sulfate, chrondroitin sulphate, apolipoprotein E, nerve growth factor (NGF), brain-derived neurotrophic factor (BDNF), glycosylation end products, amyloid P component, laminin, and collagen type IV.

8. The method of claim 2 wherein the Alzheimer's disease marker is a protein and the observed difference is an increase or decrease in the enzymatic or biochemical activity of the protein in the transgenic mouse to which the compound has been administered, or by cells derived from the transgenic mouse to which the compound has been administered.

9. The method of claim 8 wherein the protein is selected from the group consisting of nicotine receptors, 5-HT$_2$ receptor, NMDA receptor, α2-adrenergic receptor, glutamine synthetase, glucose transporter, PPI kinase, cytochrome oxidase, heme oxygenase, calbindin, adenosine A1 receptors, choline acetyltransferase, acetylcholinesterase, glial fibrillary acidic protein (GFAP), α1-antitrypsin, C-reactive protein, α2-macroglobulin, IL-1, TNFα, IL-6, HLA-DR, HLA-A, D,C, CR3 receptor, MHC I, MHC II, CD 31, CR4, CD45, CD64, CD4, spectrin, ubiquitin, and apolipoprotein E.

10. The method of claim 2 wherein the Alzheimer's disease marker is a nucleic acid encoding a protein and the observed difference is an increase or decrease in the amount of the nucleic acid present in the transgenic mouse to which the compound has been administered, or by cells derived from the transgenic mouse to which the compound has been administered.

11. The method of claim 10 wherein the encoded protein is selected from the group consisting of growth inhibitory factor, Cat D,B, Neuronal Thread Protein, nicotine receptors, 5-$HT_2$ receptor, NMDA receptor, α2-adrenergic receptor, synaptophysin, p65, glutamine synthetase, glucose transporter, PPI kinase, GAP43, cytochrome oxidase, heme oxygenase, calbindin, adenosine A1 receptors, choline acetyltransferase, acetylcholinesterase, glial fibrillary acidic protein (GFAP), α1-antitrypsin, C-reactive protein, α2-macroglobulin, IL-1, TNFα, IL-6, HLA-DR, HLA-A, D,C, CR3 receptor, MHC I, MHC II, CD 31, CR4, CD45, CD64, CD4, spectrin, tau, ubiquitin, MAP-2, apolipoprotein E, nerve growth factor (NGF), brain-derived neurotrophic factor (BDNF), advanced glycosylation end products, receptor for advanced glycosylation end products, COX-2, CD18, C3, fibroblast growth factor, CD44, ICAM-1, lactotransferrin, C1q, C3d, C4d, C5b–9, gamma RI, Fc gamma RII, CD8, CD59, vitronectin, vitronectin receptor, beta-3 integrin, Apo J, clusterin, type 2 plasminogen activator inhibitor, midkine, macrophage colony stimulating factor receptor, MRP14, 27E10, interferon-alpha, S100β, $cPLA_2$, c-jun, c-fos, HSP27, HSP70, MAP5, membrane lipid peroxidase, protein carbonyl formation, junB, junD, fosB, fra1, cyclin D1, p53, NGFI-A, NGFI-B, IκB, NFκB, IL-8, MCP-1, MIP-1α, matrix metaloproteinases, 4-hydroxynonenal-protein conjugates, amyloid P component, laminin, and collagen type IV.

12. The method of claim 2 wherein the Alzheimer's disease marker is a behavior and the observed difference is a change in the behavior observed in the transgenic mouse to which the compound has been administered.

13. The method of claim 12 wherein the behavior is selected from the group consisting of behavior using working memory, behavior using reference memory, locomotor activity, emotional reactivity to a novel environment or to novel objects, and object recognition.

14. The method of claim 2 wherein the Alzheimer's disease marker is a histopathology and the observed difference is a decrease in the extent or severity of the histopathology present in the transgenic mouse to which the compound has been administered.

15. The method of claim 14 wherein the histopathology marker is selected from the group consisting of compacted plaques, neuritic dystrophy, gliosis, Aβ deposits, decreased synaptic density, and neuropil abnormalities.

16. The method of claim 14 wherein the Alzheimer's disease marker is selected from the group consisting of APP695, APP751, and APP770, and wherein the change in histopathology is a reduction in the amount of Alzheimer's disease marker localized in plaques and neuritic tissue.

17. The method of claim 16 wherein the intron is an APP gene intron.

18. The method of claim 2 wherein the Alzheimer's disease marker is cognition and the observed difference is a change in the cognition of the transgenic mouse to which the compound has been administered.

19. The method of claim 2 wherein the marker is detected or measured using RT-PCR, RNase protection, Northern analysis, R-dot analysis, ELISA, antibody staining, laser scarming confocal imaging, and immunoelectron micrography.

20. The method of claim 2 wherein the codon encoding amino acid 717 is mutated to encode an amino acid selected from the group consisting of Ile, Phe, Gly, Tyr, Leu, Ala, Pro, Trp, Met, Ser, Thr, Mn, and Gln.

21. The method of claim 20 wherein the codon encoding amino acid 717 is mutated to encode Phe.

22. The method of claim 2 wherein the codon encoding amino acid 670 is mutated to encode an amino acid selected from the group consisting of Asn and Glu, or the codon encoding amino acid 670 is deleted, and/or
wherein the codon encoding amino acid 671 is mutated to encode an amino acid selected from the group consisting of Ile, Leu, Tyr, Lys, Glu, Val, and Ala, or the codon encoding amino acid 671 is deleted.

23. The method of claim 22 wherein the codon encoding amino acid 670 is mutated to encode Asn, and/or the codon encoding amino acid 671 is mutated to encode Leu or Tyr.

24. The method of claim 2 wherein the promoter mediates expression of the construct such that $Aβ_{tot}$ is expressed at a level of at least 30 nanograms per gram of hippocampal or cortical brain tissue of the mouse when it is two to four months old, Aβ1–42 is expressed at a level of at least 8.5 nanograms per gram of hippocampal or cortical brain tissue of the mouse when it is two to four months old, APP and APPα combined are expressed at a level of at least 150 picomoles per gram of hippocampal or cortical brain tissue of the mouse when it is two to four months old, APPβ is expressed at a level of at least 40 picomoles per gram of hippocampal or cortical brain tissue of the mouse when it is two to four months old, and/or mRNA encoding the Aβ-containing protein is expressed to a level at least twice that of mRNA encoding the endogenous APP of the transgenic mouse in hippocampal or cortical brain tissue of the mouse when it is two to four months old.

25. The method of claim 1, wherein the Aβ-containing protein consists of all or a contiguous portion of a protein selected from the group consisting of
APP770 bearing a mutation in one or more of the amino acids selected from the group consisting of amino acid 669, 670, 671, 690, 692, and 717, APP751 bearing a mutation in one or more of the amino acids selected from the group consisting of amino acid 669, 670, 671, 690, 692, and 717, and APP695 bearing a mutation in one or more of the amino acids selected from the group consisting of amino acid 669, 670, 671, 690, 692, and 717.

26. The method of claim 25 wherein the region of the construct encoding a human amnyloid precursor protein is selected from the group consisting of APP770 cDNA bearing a mutation in the codon encoding amino acid 669, 670, 671, 690, 692, 717, or a combination of these mutations; APP751 cDNA bearing a mutation in the codon encoding amino acid 669, 670, 671, 690, 692, 717, or a combination of these mutations; the APP695 cDNA bearing a mutation in the codon encoding amino acid 669, 670, 671, 690, 692, 717, or a combination of these mutations; APP695, APP751, or APP770 cDNA truncated at amino acid 671 or 685; APP cDNA truncated to encode amino acids 646 to 770 of APP; a combination cDNA/genomic APP gene construct bearing a mutation in the codon encoding amino acid 669, 670, 671, 690, 692, 717, or a combination of these mutations; and a combination cDNA/genomic APP gene construct truncated at amino acid 671 or 685.

27. The method of claim 1 wherein the DNA encoding the Aβ-containing protein is cDNA or a cDNA/genomjc DNA hybrid, wherein the cDNA/genomic DNA hybrid includes at least one APP intron sequence wherein the intron sequence is sufficient for splicing.

28. The method of claim 1 wherein the promoter is the human platelet derived growth factor β chain gene promoter.

29. The method of claim 1 wherein the region further comprises DNA encoding a second protein, wherein the DNA encoding the Aβ-containing protein and the DNA encoding the second protein are operative linked such that the region encodes an Aβ-containing fusion protein comprising a fusion of the Aβ-containing protein and the second protein.

30. The method of claim 29 wherein the second protein is a signal peptide.

31. The method of claim 1 wherein the construct further comprises an effective amount of at least one intron, wherein the effective amount of at least one intron is located in the region of the construct encoding the Aβ-containing protein.

32. The method of claim 1 wherein the Aβ-containing protein consists of all or a contiguous portion of a protein selected from the group consisting APP770 bearing a mutation in one or more of the amino acids selected from the group consisting of amino acid 669, 670, 671, 690, 692, and 717, APP751 bearing a mutation in one or more of the amino acids selected from the group consisting of amino acid 669, 670, 671, 690, 692, and 717, and APP695 bearing a mutation in one or more of the ammo acids selected from the group consisting of amino acid 669, 670, 671, 690, 692, and 717.

33. A method of selecting a transgenic mouse ha a model of Aizheimer's disease, comprising
providing a plurality of transgenic mice, each comprising a nucleic acid construct stably incorporated into the genome, wherein the construct comprises a promoter for expression of the construct in a mammalian cell and a region encoding an Aβ-containing protein, wherein the promoter is operatively linked to the region,
wherein the region comprises DNA encoding the Aβ-containing protein, wherein the Aβ-containing protein consists of all or a contiguous portion of a protein selected from the group consisting of
APP770 bearing a mutation in one or more of the amino acids selected from the group consisting of amino acid 669, 670, 671, 690, 692, and 717, APP751 bearing a mutation in one or more of the amino acids selected from the group consisting of amino acid 669, 670, 671, 690, 692, and 717, and APP695 bearing a mutation in one or more of the amino acids selected from the group consisting of amino acid 669, 670, 671, 690, 692, and 711, a protein consisting of amino acids 672 to 770 of APP; and a protein consisting of amino acids 672 to 714 of APP;
determining expression levels of Aβ and Congo red staining in the brains of each of the transgenic mice;
identifying a transgenic mouse;
wherein Aβ is expressed at a level of at least 50 ng/g brain tissue in the identified transgenic mouse when the transgenic mouse is three months of age; and
using an offspring of the identical transgenic mouse as a model of Alzheimer's Disease.

34. The method of claim 33, further comprising administering a compound to be tested to the offspring or cells derived therefrom, and
detecting or measuring the Alzheimer's disease marker such that any difference between the marker in the transgenic mouse, or by cells derived from the transgenic mouse rodent, and the marker in a transgenic mouse to which the compound has not been administered, or by cells derived from the transgenic mouse to which the compound has not been administered, is observed,
wherein an observed difference in the marker indicates that the compound has an effect on the marker.

35. The method of claim 33 wherein the Alzheimer's disease marker is a protein and the observed difference is an increase or decrease in the amount of the protein present in the transgenic mouse to which the compound has been administered, or in cells derived from the transgenic mouse to which the compound has been administered.

36. The method of claim 35 wherein the protein is selected from the group consisting of Cat D,B, Neuronal Thread Protein (CSF), nicotine receptors, 5-HT$_2$ receptor, NMDA receptor, α2-adrenergic receptor, synaptophysin, p65, glutarnine synthetase, glucose transporter, PPI kinase, GAP43, cytochrome oxidase, calbindin, adenosine A1 receptors, choline acetyltransferase, acetylcholinesterase, glial fibrillary acidic protein (GFAP), α1-antichymotrypsin, α1-antitrypsin, C-reactive protein, α2-macroglobulin, IL-1, TNFα, IL-6, HLA-DR, HLA-A, D,C, CR3 receptor, MHC I, MHC II, CD 31, CR4, CD45, CD64, CD4, spectrin, tau, ubiquitin, MAP-2, apolipoprotein E, glycosylation end products, amyloid P component, laminen, and collagen type IV.

37. The method of claim 33 wherein the Alzheimer's disease marker is a protein and the observed difference is a reduction or absence of the protein in plaques or neuritic tissue present in the transgenic mouse to which the compound has been administered.

38. The method of claim 37 wherein the protein is selected from the group consisting of Cat D,B, protein kinase C, NADPH, C3d, C1q, CS, C4bp, C5a-C9, tau, ubiquitin, MAP-2, neurofilaments, heparin sulfate, chrondroitin sulphate, apolipoprotein E, glycosylation end products, amyloid P component, laminen, and collagen type IV.

39. The method of claim 33 wherein the Alzheimer's disease marker is a protein and the observed difference is an increase or decrease in the enzymatic or biochemical activity of the protein in the fransgenic mouse to which the compound has been administered, or in cells derived from the transgenic mouse to which the compound has been administered.

40. The method of claim 39 wherein the protein is selected from the group consisting of nicotine receptors, 5-HT$_2$ receptor, NMDA receptor, α2-adrenergic receptor, glutamine synthetase, glucose transporter, PPI kinase, cytochrome oxidase, calbindin, adenosine A1 receptors, choline acetyltransferase, acetylcholinesterase, glial fibrillary acidic protein (GFAP), α1-antichymotrypsin, α1-antitrypsin, C-reactive protein, α2-macroglobulin, IL-1, TNFα, IL-6, HLA-DR, HLA-A, D,C, CR3 receptor, MHC I, MHC II, CD 31, CR4, CD45, CD64, CD4, spectrin, ubiquitin, and apolipoprotein E.

41. The method of claim 33 wherein the Alzheimer's disease marker is a nucleic acid encoding a protein and the observed difference is an increase or decrease in the amount of the nucleic acid present in the transgenic mouse to which the compound has been administered, or in cells derived from the transgenic mouse to which the compound has been administered.

42. The method of claim 41 wherein the protein is selected from the group consisting of growth inhibitory factor, Cat D,B, Neuronal Thread Protein (CSF), nicotine receptors, 5-HT$_2$ receptor, NMDA receptor, α2-adrenergic receptor, synaptophysin, p65, glutamine synthetase, glucose transporter, PPI kinase, GAP43, cytochrome oxidase, calbindin, adenosine A1 receptors, choline acetyltransferase, acetylcholinesterase, glial fibrillary acidic protein (GFAP), α1-antichymotrypsin, α1-antitrypsin, C-reactive protein, α2-macroglobulin, IL-1, TNFα, IL-6, HLA-DR, HLA-A, D,C, CR3 receptor, MHC I, MHC II, CD 31, CR4, CD45, CD64, CD4, spectrin, tall, ubiquitin, MAP-2, apolipoprotein E, glycosylation end products, amyloid P component, laminen, and collagen type IV.

43. The method of claim 33 wherein the Alzheimer's disease marker is a behavior and the observed difference is a change in the behavior observed in the transgenic mouse to which the compound has been administered.

44. The method of claim 43 wherein the behavior is selected from the group consisting of behavior using working memory, behavior using reference memory, locomotor activity, emotional reactivity to a novel environment or to novel objects, and object recognition.

45. The method of claim 33 wherein the Alzheimer's disease marker is a histopatbology and the observed difference is a decrease in the extent or severity of the histopathology present in the transgenic mouse to which the compound has been administered.

46. The method of claim 45 wherein the histopathology is selected from the group consisting of compacted plaques, neuritic dystrophy, gliosis, A,β deposits, decreased synaptic and neuropil abnormalities.

47. The method of of claim 45 wherein the Alzheimer's disease marker is selected from the group consisting of APP695, APP751, and APP770, and wherein the change in histopathology is a reduction in the amount of the marker localized in plaques and neuritic tissue.

48. The method of claim 33 wherein the Alzheimer's disease marker is cognition and the observed difference is a change in the cognition of the transgenic mouse to which the compound has been administered.

49. The method of claim 33 wherein the marker is detected or measured using RT-PCR, ELISA, antibody staining, laser scanning confocal imaging, and immunoelectron micrography.

50. The method of claim 33 wherein the codon encoding amino acid 717 is mutated to encode an amino acid selected from the group consisting of Ile, Phe, Gly, Tyr, Leu, Ala, Pro, Tip, Met, Ser, Thr, Asn, and Gin.

51. The method of claim 50 wherein the codon encoding amino acid 717 is mutated to encode Phe.

52. The method of claim 33 wherein the codon encoding amino acid 670 is mutated to encode an amino acid selected from the group consisting of Asn and Glu, or the codon encoding amino acid 670 is deleted, and wherein the codon encoding amino acid 671 is mutated to encode an amino acid selected from the group consisting of Ile, Lys, Glu, Val, and Ala, or the codon encoding amino acid 671 is deleted.

53. The method of claim 52 wherein the codon encoding amino acid 670 is mutated to encode Asn, and the codon encoding amino acid 671 is mutated to encode Leu.

54. The method of claim 33 wherein the Alzheimer's disease marker is selected from the group consisting of $A\beta_{tot}$, $A\beta_{1-42}$, $A\beta_{N3}(pE)$, $A\beta_{x-42}$, and $A\beta_{Insoluble}$.

55. The method of claim 33 wherein the construct further comprises an effective amount of at least one intron, wherein the effective amount of at least one intron is located in the region of the construct encoding a human amyloid precursor protein.

56. The method of claim 55 wherein the intron is an APP gene intron.

* * * * *